(12) United States Patent
Albertson et al.

(10) Patent No.: US 12,168,027 B2
(45) Date of Patent: *Dec. 17, 2024

(54) METHODS ASSOCIATED WITH TUMOR BURDEN FOR ASSESSING RESPONSE TO A CELL THERAPY

(71) Applicant: Juno Therapeutics, Inc., Seattle, WA (US)

(72) Inventors: Tina Albertson, Seattle, WA (US); Jacob Randolph Garcia, Seattle, WA (US); He Li, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,672

(22) Filed: Dec. 16, 2022

(65) Prior Publication Data

US 2023/0172988 A1    Jun. 8, 2023

Related U.S. Application Data

(63) Continuation of application No. 16/760,382, filed as application No. PCT/US2018/058579 on Oct. 31, 2018, now Pat. No. 11,564,946.

(60) Provisional application No. 62/580,417, filed on Nov. 1, 2017.

(51) Int. Cl.
*A61K 35/17* (2015.01)
*A61P 35/00* (2006.01)
*C07K 16/28* (2006.01)
*G01N 33/574* (2006.01)

(52) U.S. Cl.
CPC .............. *A61K 35/17* (2013.01); *A61P 35/00* (2018.01); *C07K 16/2803* (2013.01); *G01N 33/57407* (2013.01)

(58) Field of Classification Search
CPC ............ A61K 35/17; A61K 2039/5156; A61K 2039/5158; A61K 39/0011; A61P 35/00; C07K 16/2803; C07K 14/7051; C07K 2319/03; G01N 33/57407; G01N 33/5014; G01N 33/57426; G01N 2800/52; G01N 2800/56
See application file for complete search history.

(56) References Cited

U.S. PATENT DOCUMENTS

| | | |
|---|---|---|
| 3,799,934 A | 3/1974 | Vater et al. |
| 4,452,773 A | 6/1984 | Molday |
| 4,690,915 A | 9/1987 | Rosenberg |
| 4,795,698 A | 1/1989 | Owen |
| 5,200,084 A | 4/1993 | Liberti |
| 5,219,740 A | 6/1993 | Miller |
| 5,527,814 A | 6/1996 | Louvel |
| 5,591,827 A | 1/1997 | Brankenhoff et al. |
| 6,040,177 A | 3/2000 | Riddell |
| 6,207,453 B1 | 3/2001 | Maass |
| 6,410,319 B1 | 6/2002 | Raubitschek |
| 6,451,995 B1 | 9/2002 | Cheung |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen |
| 7,446,190 B2 | 11/2008 | Sadelain |
| 7,446,191 B2 | 11/2008 | Jensen |
| 7,514,444 B2 | 4/2009 | Honigberg et al. |
| 7,645,755 B2 | 1/2010 | Illig et al. |
| 7,893,075 B2 | 2/2011 | Zhang et al. |
| 8,008,309 B2 | 8/2011 | Honigberg et al. |
| 8,008,450 B2 | 8/2011 | Williams et al. |
| 8,153,765 B2 | 4/2012 | Park et al. |
| 8,247,425 B2 | 8/2012 | Bazhina et al. |
| 8,324,353 B2 | 12/2012 | Jensen |
| 8,339,645 B2 | 12/2012 | Nakawaki et al. |
| 8,389,282 B2 | 3/2013 | Sadelain |

(Continued)

FOREIGN PATENT DOCUMENTS

| | | |
|---|---|---|
| EP | 0452342 | 10/1991 |
| EP | 2277543 | 1/2011 |

(Continued)

OTHER PUBLICATIONS

US 8,252,592 B2, 08/2012, Sadelain (withdrawn)

(Continued)

*Primary Examiner* — Scarlett Y Goon
*Assistant Examiner* — Audrey L Buttice
(74) *Attorney, Agent, or Firm* — MORRISON & FOERSTER LLP

(57) ABSTRACT

Provided herein are methods and articles of manufacture for use with cell therapy for the treatment of diseases or conditions, e.g., cancer, including for predicting and treating a toxicity. In some embodiments, the toxicity is related to cytokine release syndrome (CRS). The methods generally involve assessing a change in a factor indicative of tumor burden in a subject that is associated with and/or correlate to a risk of developing toxicity. In some aspects, the methods can be used to determine if the subject is at risk or likely at risk for developing a toxicity following administration of the cell therapy. Also provided are methods for treating a subject having a disease or condition, in some cases involving administration of the cell therapy, based on assessment of risk of developing a toxicity following administration of the therapy. Also provided herein are reagents and kits for performing the methods.

37 Claims, No Drawings

Specification includes a Sequence Listing.

(56) References Cited

U.S. PATENT DOCUMENTS

| | | | |
|---|---|---|---|
| 8,399,514 | B2 | 3/2013 | Lukashev et al. |
| 8,476,284 | B2 | 7/2013 | Honigberg et al. |
| 8,497,118 | B2 | 7/2013 | Jensen |
| 8,497,277 | B2 | 7/2013 | Lyndersay et al. |
| 8,562,991 | B2 | 10/2013 | Igawa et al. |
| 8,603,477 | B2 | 12/2013 | Afar et al. |
| 8,697,711 | B2 | 4/2014 | Honigberg et al. |
| 8,703,780 | B2 | 4/2014 | Honigberg et al. |
| 8,735,403 | B2 | 5/2014 | Honigberg et al. |
| 8,754,090 | B2 | 6/2014 | Buggy et al. |
| 8,754,091 | B2 | 6/2014 | Honigberg et al. |
| 8,802,374 | B2 | 8/2014 | Jensen |
| 8,822,647 | B2 | 9/2014 | Jensen |
| 8,911,993 | B2 | 12/2014 | June |
| 8,957,079 | B2 | 2/2015 | Honigberg et al. |
| 8,999,999 | B2 | 4/2015 | Buggy et al. |
| 9,125,889 | B2 | 9/2015 | Buggy et al. |
| 9,181,257 | B2 | 11/2015 | Honigberg et al. |
| 9,296,753 | B2 | 3/2016 | Smyth et al. |
| 11,815,514 | B2 | 11/2023 | Li et al. |
| 2002/0131960 | A1 | 9/2002 | Sadelain |
| 2003/0170238 | A1 | 9/2003 | Gruenberg |
| 2007/0116690 | A1 | 5/2007 | Yang et al. |
| 2010/0190755 | A1 | 7/2010 | Abato et al. |
| 2010/0260748 | A1 | 10/2010 | Elkins et al. |
| 2011/0003380 | A1 | 1/2011 | Miltenyi |
| 2011/0044998 | A1 | 2/2011 | Bedian et al. |
| 2012/0189622 | A1 | 7/2012 | Tesar et al. |
| 2013/0149337 | A1 | 6/2013 | Cooper |
| 2013/0287748 | A1 | 10/2013 | June |
| 2014/0065141 | A1 | 3/2014 | Daniel et al. |
| 2014/0271635 | A1 | 9/2014 | Brogdon |
| 2015/0119267 | A1 | 4/2015 | Joyce |
| 2015/0283178 | A1 | 10/2015 | June et al. |
| 2016/0032248 | A1 | 2/2016 | Short et al. |
| 2016/0152723 | A1 | 6/2016 | Chen et al. |
| 2016/0185861 | A1 | 6/2016 | Bedoya et al. |
| 2019/0277858 | A1 | 9/2019 | Li et al. |
| 2020/0078400 | A1 | 3/2020 | Li et al. |
| 2021/0198372 | A1 | 7/2021 | Albertson et al. |
| 2024/0103012 | A1 | 3/2024 | Li et al. |

FOREIGN PATENT DOCUMENTS

| | | |
|---|---|---|
| EP | 2537416 | 12/2012 |
| RU | 2423525 | 7/2011 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1999/018129 | 4/1999 |
| WO | WO 1999/060120 | 11/1999 |
| WO | WO 2000/0014257 | 3/2000 |
| WO | WO 2003/020763 | 3/2003 |
| WO | WO 2004/033685 | 4/2004 |
| WO | WO 2006/000830 | 1/2006 |
| WO | WO 2006/009755 | 1/2006 |
| WO | WO 2006/099875 | 9/2006 |
| WO | WO 2008/063888 | 5/2008 |
| WO | WO 2009/072003 | 6/2009 |
| WO | WO 2009/080829 | 7/2009 |
| WO | WO 2010/033140 | 3/2010 |
| WO | WO 2011/044186 | 4/2011 |
| WO | WO 2011/056983 | 5/2011 |
| WO | WO 2011/119773 | 9/2011 |
| WO | WO 2012/062596 | 5/2012 |
| WO | WO 2012/092612 | 7/2012 |
| WO | WO 2012/129514 | 9/2012 |
| WO | WO 2013/071154 | 5/2013 |
| WO | WO 2013/001802 | 6/2013 |
| WO | WO 2013/123061 | 8/2013 |
| WO | WO 2013/126726 | 8/2013 |
| WO | WO 2013/166321 | 11/2013 |
| WO | WO 2014/011984 | 1/2014 |
| WO | WO 2014/031687 | 2/2014 |
| WO | WO 2014/055668 | 4/2014 |
| WO | WO 2014/210064 | 12/2014 |
| WO | WO 2015/136298 | 9/2015 |
| WO | WO 2016/064929 | 4/2016 |
| WO | WO 2016/090312 | 6/2016 |
| WO | WO 2016/090320 | 6/2016 |
| WO | WO 2016/090327 | 6/2016 |
| WO | WO 2016/090329 | 6/2016 |
| WO | WO 2016/132366 | 8/2016 |
| WO | WO 2017/040930 | 3/2017 |
| WO | WO 2017/096331 | 6/2017 |
| WO | WO 2017/165571 | 9/2017 |
| WO | WO 2018/102787 | 6/2018 |
| WO | WO 2018/223098 | 12/2018 |
| WO | WO 2018/223101 | 12/2018 |
| WO | WO 2019/109053 | 6/2019 |

OTHER PUBLICATIONS

Mount, N.M., et al (2015) Cell-based therapy technology classification and translational challenges Phil. Trans. R. Soc. B. 370; 1-16 (Year: 2015).*

Tang, J., et al (2018) The global landscape of cancer cell therapy Nature Reviews | Drug Discovery 17; 465-467 (Year: 2018).*

Sheth, V., and J. Gauthier (2021) Taming the Beast: CRS and ICANs after CAR T-cell therapy for ALL Bone Marrow Transplant 56(3); 552-566 (Year: 2021).*

Yan, Z., et al (2021) Characteristics and risk factors of cytokine release syndrome in chimeric antigen receptor T cell treatment Frontiers in Immunology 12(611366); 1-8 (Year: 2021).*

Aagaard et al., "RNAi therapeutics: principles, prospects and challenges," Adv Drug Deliv Rev. (2007) 59(2-3):75-86.

Abramson et al., "High durable CR rates in relapsed/refractry (R/R) aggressive B-NHL treated with the CD19-directed CAR T cell product JCAR017 (Transcend NHL 001): Defined composition allows for dose-finding and definition of pivotal cohort," Blood (2017) 130 (suppl. 1):581.

Abramson et al., "High durable CR rates in R/R aggressive B-NHL treated with JCAR017 (lisocabtagene maraleuce; liso-cel) (Transcend NHL 001): Defined composition CD19-directed CAR T cel product allows for dose-finding and definition of pivotal cohort," oral presentation at ASH 2017 Dec. 9-12, 2017.

Al-Lazikani et al., "Standard conformations for the canonical structures of immunoglobulins," J Mol Biol (1997) 273(4):927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Ansell, Stephen M., et al. "CD4+ T-cell immune response to large B-cell non-Hodgkin's lymphoma predicts patient outcome." *Journal of Clinical Oncology* 19.3 (2001): 720-726.

Barrett et al., "Interleukin 6 Is Not Made By Chimeric Antigen Receptor T Cells and Does Not Impact Their Function," Abstract 654. Presented at ASH 58th Annual Meeting San Diego, CA (Dec. 3-6, 2016).

Barrett et al., "Chimeric antigen receptor therapy for cancer," Annu Rev Med. (2014); 65: 333-347.

Batlevi et al., "Novel immunotherapies in lymphoid malignancies," Nat Rev Clin Oncol. Jan. 2016;13(1):25-40.

Benson et al., "CS1-Directed monoclonal antibody therapy for multiple myeloma," J Clin Oncol (2012) 30(16):2012-2015.

Bonifant et al., "Toxicity and management in CAR T-cell therapy," Molecular Therapy—Oncolytics (2016) 3:16011.

Boris-Lawrie et al., "Recent advances in retrovirus vector technology," Cur. Opin. Genet. Develop. (1993) 3:102-109.

Bork et al., "Powers and pitfalls in sequence analysis: the 70% hurdle," Genome Res. (2000) 10(4):398-400.

Bowie et al., "Deciphering the message in protein sequences: tolerance to amino acid substitutions," Science. (1990) 247(4948): 1306-10.

Brandl et al., "The effect of dexamethasone on polyclonal T cell activation and redirected target cell lysis as induced by a CD19/

(56) References Cited

OTHER PUBLICATIONS

CD3-bispecific single-chain antibody construct," Cancer Immunology Immunotherapy (2007) 56:1551-1563.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brown et al., "Tolerance of single, but not multiple, amino acid replacements in antibody VH CDR 2: a means of minimizing B cell wastage from somatic hypermutation?" J Immunol. (1996) 156(9):3285-91.
Brudno et al., "Toxicities of chimeric antigen receptor T cells: recognition and management," Blood (2016) 127(26):3321-3330.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. (1990) 111(5 Pt 1):2129-38.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Butovsky et al., "Targeting miR-155 restores abnormal microglia and attenuates disease in SOD1 mice," Ann Neurol (2015) 77(1): 75-99.
Carceller et al., "Response assessment in paediatric phase I trials according to RECIST guidelines: survival outcomes, patterns of progression and relevance of changes in tumour measurements," Pediatr Blood Cancer (2016) 63(8):1400-06.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Cavalieri et al., "Human T lymphocytes transduced by lentiviral vectors in the absence of TCR activation maintain an intact immune competence," Blood (2003) 102(2): 497-505.
Cavaletti et al., "Chemotherapy-induced peripheral neurotoxicity," Nat Rev Neurol (2010) 6(12):657-666.
Cheadle et al., "Chimeric antigen receptors for T-cell based therapy," Methods Mol Biol. (2012) 907: 645-66.
Chervin et al., "Engineering higher affinity T cell receptors using a T cell display system," J Immunol Methods. (2008) 339(2): 175-84.
Chicaybam et al., "An efficient low cost method for gene transfer to T lymphocytes," PLoS One (2013) 8(3): e60298.
Cho et al., "Human mammalian cell sorting using a highly integrated micro-fabricated fluorescence-activated cell sorter (microFACS)," Lab Chip (2010) 10: 1567-1573.
Chothia et al.,. "The outline structure of the T-cell alpha beta receptor," EMBO J. (1988) 7(12): 3745-55.
Christiansen et al., "Elevate serum levels of soluble ICAM-1 in non-Hodgkins lymphomas correlate with tumour burden, disease activity and other prognostic markers," Br J Haematology (1996) pp. 639-646.
Chu et al., "CS1-specific chimeric antigen receptor (CAR)-engineered natural killer cells enhance in vitro and in vivo antitumor activity against human multiple myeloma," Leukemia (2014) 28(4):917-927.
Clark et al., "Discovery and development of Janus kinase (JAK) inhibitors for inflammatory diseases," J Med Chem. (2014) 57(12):5023-38.
Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.
Clackson et al., "Making antibody fragments using phage display libraries," Nature (1991) 252(6336):624-628.
Clinical Trial Identifier NCT01865617, "Laboratory treated T cells in treating patients with relapsed or refractory chronic lymphocytic leukemia, non-Hodgkin lymphoma, or acute lymphoblastic leukemia," Retrieved from https://clinicaltrials.gov/ct2/show/NCT01865617 on May 31, 2018; first published May 31, 2013.
Conway et al., "Inhibition of colony-stimulating-factor-1 signaling in vivo with the orally bioavailable cFMS kinase inhibitor GW2580," Proc Natl Acad Sci U.S.A (2005) 102(44):16078-16083.
Cooper et al., "T-cell clones can be rendered specific for CD19: toward the selective augmentation of the graft-versus-B-lineage leukemia effect," Blood. (2003) 101:1637-1644.
Crump et al., "Outcomes in refractory diffuse large B-cell lymphoma: results from the international SCHOLAR-1 study," Blood (2017) 130(16):1800-8.
Dagher et al., "Colony-stimulating factor 1 receptor inhibition prevents microglial plaque association and improves cognition in 3xTg-AD mice," J Neuroinflammation (2015) 12; 139.
Davila et al., "CD19 CAR-targeted T cells induce long-term remission and B Cell Aplasia in an immunocompetent mouse model of B cell acute lymphoblastic leukemia," PLoS One (2013) 8(4): e61338.
Davila et al., "Efficacy and toxicity management of 19-28z CAR T cell therapy in B cell acute lymphoblastic leukemia," Science Translational Medicine (2014) 6(224):224ra25.
Davila et al., "CD19-Targeted T Cells for Hematologic Malignancies: Clinical Experience to Date," Cancer J (2015) 21(6):470-474.
De Felipe et al., "Targeting of proteins derived from self-processing polyproteins containing multiple signal sequences," Trafic (2004) 5(8):616-626.
De Felipe, "Skipping the co-expression problem: the new 2A "CHYSEL" technology," Genetics Vaccines and Therapy (2004) 2:13.
Dick et al., "Use of LDH and autoimmune side effects to predict response to ipilimumab treatment," Immunotherapy (2016) 8(9):1033-1044.
Dobber et al., "The in vivo effects of neutralizing antibodies against IFN-gamma, IL-4, or IL-10 on the humoral immune response in young and aged mice," Cell Immunol (1995) 160(2): 185-192.
Dupont et al., "Validation and comparison of luminex multiplex cytokine analysis kits with ELISA: determinations of a panel of nine cytokines in clinical sample culture supernatants," J Reprod Immunol. (2005) 66(2):175-191.
Eisenhauer et al., "New response evaluation criteria in solid tumors: Revised RECIST guilines (version 1.1)," Eur J Cancer (2009) 45(2):228-47.
Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172.
Feng, Zipei, et al. "Utilizing quantitative immunohistochemistry for relationship analysis of tumor microenvironment of head and neck cancer patients." *Journal for Immuno Therapy of Cancer* 2.3 (2014): P258 (3pgs).
Fleischmann et al., "Safety of extended treatment with anakinra in patients with rheumatoid arthritis," Ann Rheum Dis (2006) 65(8):1006-1012.
Frey et al., "Cytokine release syndrome with novel therapeutics for acute lymphoblastic leukemia," Hematology Am Soc Hematol Educ Program (2016) 2016(1):567-572.
Garfall et al., "Posterior Reversible Encephalopathy Syndrome (PRES) after Infusion of Anti-Bcma CAR T cells (CART-BCMA) for Multiple Myeloma: Successful Treatment with Cyclophosphamide," Blood (2016) Dec; 128(22):5702.
Garfall et al., "Immunotherapy with chimeric antigen receptors for multiple myeloma," Discov Med. (2014) 17(91): 37-46.
Godin et al., "Microfluidics and photonics for Bio-System-on-a-Chip: a review of advancements in technology towards a microfluidic flow cytometry chip," J Biophoton. (2008) 1(5): 355-376.
Gong et al., "An Antagonist of Monocyte Chemoattractant Protein 1 (MCP-1) Inhibits Arthritis in the MRL-lpr Mouse Model," J Exp Med (1997) 186(1): 131-137.
Grupp et al., "Chimeric Antigen Receptor-Modified T Cells for Acute Lymphoid Leukemia," N Engl J Med (2013) 368:1509-1518.
Grupp et al., "CD19-Redirected Chimeric Antigen Receptor T (CART19) Cells Induce a Cytokine Release Syndrome (CRS) and

(56) References Cited

OTHER PUBLICATIONS

Induction of Treatable Macrophage Activation Syndrome (MAS) That Can Be Managed by the IL-6 Antagonist Tocilizumab (toc).," Blood. (2012) 120 (21): 2604.
Guido et al., "Virtual screening and its integration with modern drug design technologies," Curr Med Chem. (2008) 15(1):37-46.
Gust et al., "Endothelial activation and blood brain barrier disruption in neurotoxicity after adoptive immunotherapy with CD19 CAR-T cells," Cancer Discov (2017) 7(12):1404-19.
Haegel et al., "TG3003, an immunomodulatory anti-CD115 mAb targeting m2-macrophage polarization in the tumor microenvironment," Cancer Res AACR (2015) Abstract 288.
Hannum et al., "Interleukin-1 receptor antagonist activity of a human interleukin-1 inhibitor," Nature (1990) 343: 336-340.
Hay et al., "Kinetics and biomarkers of severe cytokine release syndrome after CD19 chimeric antigen receptor-modified T-cell therapy," Blood (2017) 130(21):2295-306.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Hill et al., "Infectious complications of CD19-targeted chimeric antigen receptor-modified T-cell immunotherapy," Blood (2018) 131(1):121-30.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Hoing et al., "Discovery of inhibitors of microglial neurotoxicity acting through multiple mechanisms using a stem-cell-based phenotypic assay," Cell Stem Cell (2012) 11(5): 620-632.
Honegger et al., "Yet another numbering scheme for immunoglobulin variable domains: an automatic modeling and analysis tool," J Mol Biol (2001) 309(3):657-670.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hunter et al., "Neutralizing anti-IL-10 antibody blocks the protective effect of tapeworm infection in a murine model of chemically induced colitis," J Immunol (2005) 174(11): 7368-7375.
Janeway et al., Immunobiology: The Immune System in Health and Disease, 3rd ED., Current Biology Publications (1997), p. 4:33.
Johnson et al., "Imaging for Staging and Response Assessment in Lymphoma," Radiology (Aug. 2015) 276(2):323-338.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kindt et al., "Antigens and Antibodies," in Chapter 4 of Kuby Immunology, 6th ed., W.H. Freeman and Co., N.Y, (2007) pp. 91, 14 pages.
Kivisakk et al., "Natalizumab treatment is associated with peripheral sequestration of proinflammatory T cells," Neurology (2009) 72(22):1922-1930.
Klaver et al., "Adoptive T-cell therapy: A need for standard immune monitoring," Immunotherapy (2015) 7(5):513-533.
Klebanoff et al., "Sorting through subsets: which T-cell populations mediate highly effective adoptive immunotherapy?," J Immunother. (2012) 35(9): 651-660.
Kochenderfer et al., "Treating B-cell cancer with T cells expressing anti-CD19 chimeric antigen receptors," Nature Reviews Clinical Oncology (2013) 10:267-276.
Kochenderfer et al., "Construction and preclinical evaluation of an anti-CD19 chimeric antigen receptor," J. Immunotherapy (2009) 32(7): 689-702.
Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kurucz et al., "A bacterially expressed single-chain Fv construct from the 2B4 T-cell receptor," Proc Natl Acad Sci U S A. (1993) 90(9): 3830-3834.
Lazar et al., "Transforming growth factor alpha: mutation of aspartic acid 47 and leucine 48 results in different biological activities," Mol Cell Biol. (1988) 8(3):1247-52.
Lee et al., "Current concepts in the diagnosis and management of cytokine release syndrome," Blood (2014) 124(2):188-95.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display", Nat Biotechnol. (2005) 23(3): 349-354.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (2016) 34(4):430-434.
Liu et al., "Overall survival of cancer patients with serum lactate dehydrogenase greater than 1000 IU/L," Tumor Biology (2016) 37:14083-14088.
Lupton et al., "Dominant positive and negative selection using a hygromycin phosphotransferase-thymidine kinase fusion gene," Mol. and Cell Biol. (1991) 11(6): 3374-3378.
Maccallum et al., "Antibody-antigen interactions: contact analysis and binding site topography," J Mol Biol (1996) 262(5):732-745.
Maloney et al., "Preliminary safety profile of the CD19-directed defined composition CAR T cell product JCAR017 in relapsed/refractory aggressive B-NHL patients: Potential for outpatient administration," Blood (2017) 131 (suppl. 1):1552.
Maloney et a., "Safety profile of the CD19-directed defined composition CAR T cell product JCAR017 (lisocabtagene maraleucel; liso-cel) in relapsed/refractory aggressive B-NHL patients: Potential for outpatient administration," poster presented at ASH 2017 Dec. 9-12, 2017.
Manthey et al., "JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia," Mol Cancer Ther (2009) 8(11): 3151-3161.
Manuri et al., "piggyBac transposon/transposase system to generate CD19-specific T cells for the treatment of B-lineage malignancies," Hum Gene Ther (2010) 21(4): 427-437.
Maude et al., "Managing Cytokine Release Syndrome Associated With Novel T Cell-Engaging Therapies," Cancer J (2014) 20(2): 119-122.
Maude et al., "Chimeric antige receptor T cells for sustained remissions in leukemia," N Eng J Med (2014) 371(16):1507-1517.
Martin et al., "Modeling antibody hypervariable loops: a combined algorithm," PNAS (1989) 86(23):9268-9272.
Mesa et al., "Ruxolitinib," Nature Reviews Drug Disovery (2012) 11(2):103-104.
Miller et al., "Improved retroviral vectors for gene transfer and expression," BioTechniques (1989) 7:980-990.
Miller et al., "Retrovirus packaging cells," Human Gene Therapy (1990) 1:5-14.
Monsky et al., "Semi-automated volumetric quantification of tumor necrosis in soft tissue sarcoma using contrast enhanced MRI," Anticancer Res (2012) 32(11):4951-61.
Mount et al., "Cell-based therapy technology classifications and translational challenges," Philos Trans R Soc Lond B Biol Sci. (2015) 370(1680): 20150017.

(56) References Cited

OTHER PUBLICATIONS

Mozley et al., "Measurement of tumor volumes improves RECIST-based response assessments in advanced lung cancer," Transl Oncol (2012) 5(1):19-25.
Muller et al., "Amino-substituted thalidomide analogs: Potent inhibitors of TNF-a production," Bioorganic & Medicinal Chemistry Letters (1999) 9(11): 1625-1630.
Nedergaard, B. S., et al. "Low density of CD3+, CD4+ and CD8+ cells is associated with increased risk of relapse in squamous cell cervical cancer." British journal of cancer 97.8 (2007): 1135-1138.
Neeplau et al ., "Chimeric antigen receptor T-cell therapy—assessment and management of toxicities," Nat Rev Clin Oncol. (2018) 15(1):47-62.
Ohno et al., "A c-fms tyrosine kinase inhibitor, Ki20227, suppresses osteoclast differentiation and osteolytic bone destruction in a bone metastasis model," Mol Cancer Ther (2006) 5(11): 2634-2643.
Park et al., "Treating cancer with genetically engineered T cells," Trends Biotechnol (2011) 29(11):550-557.
Ponomarev et al., "MicroRNA-124 promotes microglia quiescence and suppresses EAE by deactivating macrophages via the C/EBP-α-PU.1 pathway," Nat Med (2011) 17(1):64-70.
Portolano et al., "Lack of promiscuity in autoantigen-specific H and L chain combinations as revealed by human H and L chain "roulette"," J Immunol (1993) 150(3):880-887.
Porz et al., "Fully Automated Enhanced Tumor Compartmentalization: Man vs. Machine Reloaded," PLoS One. (2016) 11(11): e0165302.
Pryer et al., "Abstract #DDT02-2: MCS110: a monoclonal antibody with potent neutralizing activity against macrophage colony-stimulating factor for the treatment of tumor-induced osteolysis," AACR Annual Meeting Apr. 18-22, 2009. 69(9):DDT02-2.
Pyonteck et al., "CSF-1R inhibition alters macrophage polarization and blocks glioma progression," Nat Med (2013) 19(10):1264-1272.
Ramirez et al., "Prevention of Alzheimer's disease pathology by cannabinoids: neuroprotection mediated by blockade of microglial activation," J Neurosci (2005) 25(8):1904-1913.
Ramsborg et al., "JCAR017 is a defined composition CAR T cell product with product and process controls that deliver precise doses of CD4 and CD8 CAR T cell to patients with NHL," Blood (2017) 130(suppl. 1):4471.
Ramsborg et al., "JCAR017 (licocabtagene maraleucel; liso-cel) is a defined composition CAR T cell product with product and process controls that deliver precise doses of CD4 and CD8 CAR T cell to patients with NHL," poster presentation at ASH 2017 Dec. 9-12, 2017.
Riddell et al., "T-cell mediated rejection of gene-modified HIV-specific cytotoxic T lymphocytes in HIV-infected patients," Nature Med (1996) 2:216-223.
Ries et al., "Targeting tumor-associated macrophages with anti-CSF-1R antibody reveals a strategy for cancer therapy," Cancer Cell (2014) 25(6):846-859.
Rosenberg, "Cell transfer immunotherapy for metastatic solid cancer—what clinicians need to know," Nat Rev Clin Oncol (2011) 8(10):577-585.
Rossi, J.F., How to increase the efficiency of effector cells in cancer immunotherapy? Immunologiya Gemopoeza [in Russian], 2015, vol. 13, No. 2, p. 6-29 (English translation included).
Rovida et al., "Colony-Stimulating Factor-1 Receptor in the Polarization of Macrophages: A Target for Turning Bad to Good Ones?" J Clin Cell Immunol (2015) 6:6.
Ruella et al., "Kinase inhibitor ibrutinib prevents cytokine-Release syndrome after Anti-CD19 chimeric antigen receptor T Cells (CART) for B Cell Neoplasms," Blood (2016) 128:2159.
Ruella et al., "Kinase inhibitor ibrutinib to prevent cytokine-release syndrome after anti-CD19 chimeric antigen receptor T cells for B-cell neoplasms," Leukemia (Sep. 2016) 31(1): 246-248.
Sadelain et al., "The basic principles of chimeric antigen receptor (CAR) design," Cancer Discov (2013) 3(4):388-398.

Sanz et al., "Nimodipine inhibits IL-1β release stimulated by amyloid β from microglia," Br J Pharmacol (2012) 167(8):1702-1711.
Scarpa et al., "Characterization of recombinant helper retroviruses from moloney-based vectors in ecotropic and amphotropic packaging cell lines," Virology (1991) 180(2):849-852.
Schlueter et al., "Specificity and Binding Properties of a Single-chain T Cell Receptor," J Mol Biol (1996) 859-869.
Schuler et al., SYFPEITHI, Database for Searching and T-Cell Epitope Prediction. in Immunoinformatics Methods in Molecular Biology, (2007) 409(1): 75-93.
Shahrara et al., "Inhibition of Monocyte Chemoattractant Protein-1 Ameliorates Rat Adjuvant-Induced Arthritis," J Immunol (2008) 180(5):3447-3456.
Shank et al., "Chimeric Antigen Receptor T Cells in Hematologic Malignancies," Pharmacotherapy (2017) 37(3):334-345.
Sharma et al., "Efficient sleeping beauty DNA transposition from DNA minicircles," Molec Ther Nucl Acids (2013) 2, e74.
Shevchenko E.K. et al., Prospects for increasing the effectiveness of gene and cell therapy for cardiovascular diseases: genetically modified cells, Cell transplantology and tissue engineering [in Russian], 2010, vol. 5, No. 2, pp. 19-28.
Shimabukuro-Vornhagen et al., "Cytokine release syndrome," J Immunother Cancer. (2018) 6(1):56.
Siddiqi et al., "Patient characteristics and pre-infusion biomarkers of inflammation correlate with clinical outcomes after treatment with the defined composition, CD19-targeted CAR T cell product, JCAR017," Blood (2017) 130(suppl. 1):193.
Siddiqi et al., "Patient characteristics and pre-infusion biomarkers of inflammation correlate with clinical outcomes after treatment with the defined composition, CD19-targeted CAR T cell product, JCAR017 (lisocabtagene maraleucel; liso-cel)," oral presentation at ASH 2017 Dec. 9-12, 2017.
Siebert et al., "Monitoring cytokine profiles during immunotherapy," Immunotherapy. (2010) 2(6):799-816.
Singh et al., "ProPred: prediction of HLA-DR binding sites," Bioinformatics. (2001) 17(12): 1236-1237.
Smith et al., "The highly specific CSF1R inhibitor DCC-3014 exhibits immunomodulatory and anti-invasiv activities in cancer models," AACR 107th Annual Meeting 2016. Apr. 16-20, 2016. Abstract 4889.
Sommermeyer et al., "Fully human CD19-specific chimeric antigen receptors for T-cell therapy," Leukemia (2017) 31(10):2191-9.
Soo Hoo et al., "Characterization of a single-chain T-cell receptor expressed in Escherichia coli," Proc Natl Acad Sci U S A. (1992) 89(10): 4759-4763.
Swerdlow et al., "The 2016 revision of the World Health Organization classification of lymphoid neoplasms," Blood (2016) 127(20):2375-90.
Tai et al., "Antibody-Based Therapies in Multiple Myeloma," Bone Marrow Research (2010) vol. 2011. Article ID 924058.
Tateishi et al., "Prognostic significance of metabolic tumor burden by positron emission tomography/computed tomography in patients with relapsed/refractory diffuse large B-cell lymphoma," Cancer Sci. (2015) 106(2):186-93.
Teachey et al., "Biomarkers Accurately Predict Cytokine Release Syndrome (CRS) after Chimeric Antigen Receptor (CAR) T Cell Therapy for Acute Lymphoblastic Leukemia (ALL)," Blood (2015) 126(23):1334.
Teachey et al., "Identification of predictive biomarkers for cytokine release syndrome after chimeric antigen receptor T-cell therapy for acute lymphoblastic leukemia," Cancer Discovery (2016) 6(6):664-679.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tirkes et al., "Response criteria in oncologic imaging: review of traditional and new criteria," Radiographics. (2013) 33(5): 1323-41.

(56) References Cited

OTHER PUBLICATIONS

Tsukahara et al., "CD19 target-engineered T-cells accumulate at tumor lesions in human B-cell lymphoma xenograft mouse models," Biochem Biophys Res Commun (2013) 438(1): 84-89.

Turtle et al., "Addition of Fludarabine to Cyclophosphamide Lymphodepletion Improves In Vivo Expansion of CD19 Chimeric Antigen Receptor-Modified T Cells and Clinical Outcome in Adults with B Cell Acute Lymphoblastic Leukemia," Blood (2015) 126(23): 3773.

Turtle et al., "Engineered T cells for anti-cancer therapy," Curr. Opin. Immunol. (2012) 24(5): 633-39.

Turtle et al., "CD19 CAR-T cells of defined CD4+:CD8+ composition in adult B cell ALL patients," J Clin Invest (2016) 126(6):2123-38.

Turtle et al., "Durable molecular remissions in chronic lymphocytic leukemia treated with CD19-specific chimeric antigen receptor-modified T cells after failure of irbutinib," J Clin Oncol (2017) 35(26):3010-20.

Turtle et al., "Endothelial activation and blood-brain barrier disruption in neurotoxicity after CD19 CAR-T cell immunotherapy," Blood (2017) 130(suppl. 1):805.

Turtle et al., "Endothelial activation and blood-brain barrier disruption in neurotoxicity after CD19 CAR-T cell immunotherapy," oral presentation at ASH 2017 Dec. 9-12, 2017.

Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.

Vajdos et al., "Comprehensive functional maps of the antigen-binding site of an anti-ErbB2 antibody obtained with shotgun scanning mutagenesis," J Mol Biol. (2002) 320(2):415-28.

Valera et al., "Lenalidomide reduces microglial activation and behavioral deficits in a transgenic model of parkinson's disease," J Neuroinflammation (2015) 12:93.

Van den Neste et al., "Outcome of patients with relapsed diffuse large B-cell lymphoma who fail second-line salvage regimens in the International CORAL study," Bone Marrow Transplant (2016) 51(1):51-7.

Van Tendeloo et al., "High-level transgene expression in primary human T lymphocytes and adult bone marrow CD34+ cells via electroporation-mediated gene delivery," Gene Therapy (2000) 7(16): 1431-1437).

Verhoeyen et al., "Lentiviral vector gene transfer into human T cells," Methods Mol Biol. (2009) 506: 97-114.

Von Tresckow et al., "An open-lael, multicenter, phase I/II study of JNJ-40346527, a CDF-1R Inhibitor, in patients with relapsed or refractory hodgkin lymphoma," Clin Cancer Res (2015) 21(8):1843-1850.

Wallimann et al., "Steroids in Molecular Recognition," Chem Rev. (1997) Aug. 5;97(5):1567-1608. (42 pgs).

Wang et al., "Phenotypic and functional attributes of lentivirus-modified CD19-specific human CD8+ central memory T cells manufactured at clinical scale," J Immunother. (2012) 35(9):689-701.

Wang et al., "Effective response and delayed toxicities of refractory advanced diffuse large B-cell lymphoma treated by CD20-directed chimeric antigen receptor-modified T cells," Clin Immunol. (2014) 155(2):160-75.

Warzocha et al., "Antisense strategy: biological utility and prospects in the treatment of hematological malignancies," Leuk Lymphoma. (1997) 24(3-4):267-81.

Winter et al., "Dos-dependent inhibition of demyelination and microglia activation by IVIG," Ann Clin Transl Neurol (2016) 1-16.

Wu et al., "Adoptive T-cell therapy using autologous tumor-infiltrating lymphocytes for metastatic melanoma: current status and future outlook," Cancer (2012) 18(2): 160-175.

Wulfing et al., "Correctly folded T-cell receptor fragments in the periplasm of *Escherichia coli*. Influence of folding catalysts," J Mol Biol. (1994) 242(5): 655-669.

Xu et al., "Cytokine release syndrome in cancer immunotherapy with chimeric antigen receptor engineered T cells," Cancer Letters (2014) 343(2):172-178.

Younger et al., "Fibromyalgia symptoms are reduced by low-dose naltrexone: A pilot study," Pain Med (2009) 10(4):663-672.

Yrjanheikki et al., "Tetracyclines inhibit microglial activations and are neuroprotective in global brain ischemia," Proc Natl Acad Sci USA (1998) 95:15769-15774.

Yu et al., "Serum lactate dehydrogenase predicts prognosis and correlates with systemic inflammatory response in patients with advanced pancreatic cancer after gemcitabine-based chemotherapy," Scientific Reports (2017) 7(1):45194.

Lee et al., "T cells expressing CD19 chimeric antigen receptors for acute lymphoblastic leukaemia in children and young adults: a phase 1 dose escalation trial," The Lancet (Feb. 2015) 385(9967): 517-528.

Wang "Effective response and delayed toxicities of refractory advanced diffuse large B-cell lymphoma treated by CD20-directed chimeric antigen receptor-modified T cells," Appendix Supplementary Data (2014), 3 pages.

* cited by examiner

METHODS ASSOCIATED WITH TUMOR BURDEN FOR ASSESSING RESPONSE TO A CELL THERAPY

CROSS-REFERENCE TO RELATED APPLICATIONS

This application is a continuation of U.S. patent application Ser. No. 16/760,382, filed Apr. 29, 2020, entitled "METHODS ASSOCIATED WITH TUMOR BURDEN FOR ASSESSING RESPONSE TO A CELL THERAPY," which is a National Stage application under 35 U.S.C. § 371 of International Application No. PCT/US2018/058579, filed on Oct. 31, 2018 which claims priority from U.S. provisional patent application 62/580,417, filed Nov. 1, 2017, entitled "METHODS ASSOCIATED WITH TUMOR BURDEN FOR ASSESSING RESPONSE TO A CELL THERAPY," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042013001SeqList.xml, created: Dec. 16, 2022, which is 77,943 bytes in size. The content of the electronic Sequence Listing is herein incorporated by reference in its entirety.

FIELD

The present disclosure provides methods and articles of manufacture for use with cell therapy for the treatment of diseases or conditions, e.g., cancer, including for predicting and treating a toxicity. In some embodiments, the toxicity is related to cytokine release syndrome (CRS). The methods generally involve assessing a change in a factor indicative of tumor burden in a subject, which is associated with and/or correlates to a risk of developing toxicity following administration of the cell therapy. In some aspects, the methods can be used to determine if the subject is at risk or likely at risk for developing a toxicity following administration of the cell therapy. The present disclosure also provides methods for treating a subject having a disease or condition according to a particular treatment regimen, in some cases involving administration of the cell therapy, based on assessment of risk of developing a toxicity following administration of the therapy. Also provided herein are reagents and kits for performing the methods.

BACKGROUND

Various methods are available for adoptive cell therapy using engineered cells expressing recombinant receptors, such as chimeric antigen receptor (CARs). Improved methods are needed, for example, to increase safety and/or reduce the risk of toxicity in a subject to the administered cells. Provided are methods, kits and articles of manufacture that meet such needs.

SUMMARY

Provided herein is a method of assessing a risk of a toxicity or a toxicity-related outcome, following administration of a cell therapy, the method including assessing a factor indicative of disease burden at two time points prior to receiving a cell therapy from a subject that is a candidate for receiving a cell therapy for treatment of a disease or condition; and determining a fold change in the factor indicative of disease burden between the two time points, wherein the fold change indicates the risk or likely risk of the subject developing a toxicity following administration of the therapy to the subject. In some embodiments, the factor indicative of disease burden is a volumetric measure of a tumor or is an inflammatory marker in a sample from a subject. In some cases, the factor indicative of disease burden is a volumetric measure and the volumetric measure is a sum of the products of diameters (SPD), longest tumor diameters (LD), sum of longest tumor diameters (SLD), tumor volume, necrosis volume, necrosis-tumor ratio (NTR), peritumoral edema (PTE), and edema-tumor ratio (ETR). In some aspects, the volumetric measure is measured using computed tomography (CT), positron emission tomography (PET), and/or magnetic resonance imaging (MRI) of the subject.

In some aspects, the factor indicative of disease burden is an inflammatory marker and the inflammatory marker is C-reactive protein (CRP), erythrocyte sedimentation rate (ESR), albumin, ferritin, β2 microglobulin (β2-M), or lactate dehydrogenase (LDH). In some embodiments, the sample is or contains a blood sample, plasma sample, or serum sample. In some cases, the inflammatory marker is assessed using a colorimetric assay or an immunoassay. In some examples, the inflammatory marker is assessed using an immunoassay and the immunoassay is selected from enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

In some of any such embodiments, the subject is a human.

In some of any such embodiments, the two time points includes a first time point and a second time point, and wherein the fold change is a ratio of the factor indicative of disease burden at the first time point and the second time point. In some aspects, the two time points are both no more than one month or two months prior to receiving the cell therapy. In some cases, the two time points are not less than one week, two weeks, three weeks, four weeks, or five weeks apart. In some embodiments, the two time points are not less than three weeks apart. In some embodiments, the two time points are not more than four weeks apart, five weeks, or six weeks apart. In some instances, the second time point is more than 1, 2, 3, 4, 5, 6, or 7 days before administration of the cell therapy.

In some of any such embodiments, the cell therapy contains cells engineered to express a recombinant receptor. In some embodiments, the toxicity is neurotoxicity and/or cytokine release syndrome (CRS). In some aspects, the toxicity is early toxicity that develops within 7 days of administration of the cell therapy. In some examples, the toxicity develops within 3, 4, 5, 6, or 7 days of administration of the cell therapy. In some instances, the toxicity is a first sign of a fever or is a sustained fever following administration of the cell therapy.

In some embodiments, the subject is or is likely at risk of developing toxicity if the fold change is at or above a threshold value; or the subject is not or is likely not at risk of developing toxicity if the fold change is below a threshold value. In some aspects, the threshold value is a value that: i) is within 25%, within 20%, within 15%, within 10%, or within 5% above the average fold change of the factor indicative of disease burden and/or is within a standard deviation above the average fold change of the factor indicative of disease burden in a plurality of control subjects; ii) is above the highest fold change of the factor indicative of disease burden, optionally within 50%, within 25%, within 20%, within 15%, within 10%, or within 5% above such highest fold change, measured in at least one subject from among a plurality of control subjects; and/or iii) is above the highest fold change as measured among more than 75%, 80%, 85%, 90%, or 95%, or 98% of subjects from a plurality of control subjects.

In some embodiments, the plurality of control subjects are a group of subjects prior to receiving a cell therapy for treating a disease or condition, said cell therapy containing cells genetically engineered to express a recombinant receptor, wherein each of the subjects of the group went on to develop toxicity, optionally early toxicity, optionally a fever or a sustained fever, within 7 days after receiving the cell therapy for treating the same disease or condition.

In some embodiments, if the subject is indicated as likely to develop toxicity, selecting the subject for administration of a therapeutic regimen, the therapeutic regimen comprising administering to the subject: i. an agent or other treatment capable of treating, preventing, delaying, reducing or attenuating the development or risk of development of a toxicity and the cell therapy, wherein administration of the agent is to be administered (i) prior to, (ii) within one, two, or three days of, (iii) concurrently with and/or (iv) at first fever following, the initiation of administration of the cell therapy to the subject; ii. the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or iii. the cell therapy in an in-patient setting and/or with admission to the hospital for one or more days, optionally wherein the cell therapy is otherwise to be administered to subjects on an outpatient basis or without admission to the hospital for one or more days; or iv. an alternative therapeutic treatment other than the cell therapy.

In some embodiments, if subject is indicated as likely not at risk of developing toxicity, selecting the subject for administration of a therapeutic regimen, the therapeutic regimen comprising administering to the subject: i. the cell therapy, optionally at a non-reduced dose, optionally on an outpatient basis or without admission to the hospital for one or more days; ii. the cell therapy, wherein administration of the cell therapy does not include administering, prior to or concurrently with administering the cell therapy and/or prior to the development of a sign or symptom of toxicity other than fever, an agent or treatment capable of treating, preventing, delaying, or attenuating the development of the toxicity; or iii. the cell therapy in an outpatient setting and/or without admission of the subject to the hospital overnight or for one or more consecutive days and/or is without admission of the subject to the hospital for one or more days.

In some embodiments, if the subject is indicated as likely to develop toxicity following administration of the cell therapy, the cell therapy is not administered to the subject.

In some embodiments, the method further includes administering the therapeutic regimen to the selected subject.

Provided herein is a method of treatment including administering a therapeutic regimen to a subject that is a candidate for receiving a cell therapy for treatment of a disease or condition, wherein the administration is carried out following or based on the results of assessing the subject for a fold change in a factor indicative of disease burden between two time points prior to receiving a cell therapy. In some aspects, the factor indicative of disease burden is a volumetric measure of a tumor or is an inflammatory marker in a sample from a subject. In some examples, the factor indicative of disease burden is a volumetric measure and the volumetric measure is a sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR). In some cases, the volumetric measure is measured using computed tomography (CT), positron emission tomography (PET), and/or magnetic resonance imaging (MRI) of the subject.

In some embodiments, the factor indicative of disease burden is an inflammatory marker and the inflammatory marker is C-reactive protein (CRP), erythrocyte sedimentation rate (ESR), albumin, ferritin, $\beta$2 microglobulin ($\beta$2-M), or lactate dehydrogenase (LDH). In some aspects, the sample is or contains a blood sample, plasma sample, or serum sample. In some cases, the inflammatory marker is assessed using a colorimetric assay or an immunoassay. In some examples, the inflammatory marker is assessed using an immunoassay and the immunoassay is selected from enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

In some of any such embodiments, the subject is a human.

In some of any such embodiments, the two time points includes a first time point and a second time point, and wherein the fold change is a ratio of the factor indicative of disease burden at the first time point and the second time point. In some embodiments, the two time points are both no more than one month or two months prior to receiving the cell therapy. In some cases, the two time points are not less than one week, two weeks, three weeks, four weeks, or five weeks apart. In some instances, the two time points are not less than three weeks apart. In some cases, the two time points are not more than four weeks apart, five weeks, or six weeks apart. In some instances, the second time point is more than 1, 2, 3, 4, 5, 6, or 7 days before administration of the cell therapy.

In some of any such embodiments, the cell therapy contains cells engineered to express a recombinant receptor. In some embodiments, the fold change in the factor indicative of disease burden is associated with a risk of developing toxicity following administration of the cell therapy.

In some of any such embodiments, the toxicity is neurotoxicity and/or cytokine release syndrome (CRS). In some cases, the toxicity is early toxicity that develops within 7 days of administration of the cell therapy. In some aspects, the toxicity develops within 3, 4, 5, 6, or 7 days of administration of the cell therapy. In some instances, the toxicity is a first sign of a fever or is a sustained fever following administration of the cell therapy.

In some of any such embodiments, the assessing of the fold change in a factor indicative of disease burden between two time points includes a comparison to a threshold value, wherein the comparison indicates the risk or likely risk of the subject developing toxicity following administration of the cell therapy to the subject. In some of any such embodiments, the fold change in the factor indicative of disease burden correlates to a risk that the subject is or is likely to develop toxicity following administration of the cell therapy when it is administered. In some of any such embodiments, the subject is or is likely at risk of developing toxicity if the fold change is at or above a threshold value; or the subject is not or is likely not at risk of developing toxicity if the fold change is below a threshold value. In some examples, the threshold value is a value that: i) is within 25%, within 20%, within 15%, within 10%, or within 5% above the average fold change of the factor indicative of disease burden and/or is within a standard deviation above the average fold change of the factor indicative of disease burden in a plurality of control subjects; ii) is above the highest fold change of the factor indicative of disease burden, optionally within 50%, within 25%, within 20%, within 15%, within 10%, or within 5% above such highest fold change, measured in at least one subject from among a plurality of control subjects; and/or iii) is above the highest fold change as measured among more than 75%, 80%, 85%, 90%, or 95%, or 98% of subjects from a plurality of control subjects.

In some cases, the plurality of control subjects are a group of subjects prior to receiving a cell therapy for treating a disease or condition, said cell therapy containing cells genetically engineered to express a recombinant receptor, wherein each of the subjects of the group went on to develop toxicity, optionally early toxicity, optionally a fever or a sustained fever, within 7 days after receiving the cell therapy for treating the same disease or condition.

In some of any such embodiments, if the assessing indicates the subject is or is likely to develop toxicity following administration of the cell therapy, the therapeutic regimen includes administering to the subject: i. an agent or other treatment capable of treating, preventing, delaying, reducing or attenuating the development or risk of development of a toxicity and the cell therapy, wherein administration of the agent is to be administered (i) prior to, (ii) within one, two, or three days of, (iii) concurrently with and/or (iv) at first fever following, the initiation of administration of the cell therapy to the subject; ii. the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or iii. the cell therapy in an in-patient setting and/or with admission to the hospital for one or more days, optionally wherein the cell therapy is otherwise to be administered to subjects on an outpatient basis or without admission to the hospital for one or more days; or iv. an alternative therapeutic treatment other than the cell therapy.

In some of any such embodiments, if the assessing indicates the subject is not or is likely not to develop toxicity following administration of the cell therapy, the therapeutic regimen includes administering to the subject: i. the cell therapy, optionally at a non-reduced dose, optionally on an outpatient basis or without admission to the hospital for one or more days; ii. the cell therapy, wherein administration of the cell therapy does not include administering, prior to or concurrently with administering the cell therapy and/or prior to the development of a sign or symptom of toxicity other than fever, an agent or treatment capable of treating, preventing, delaying, or attenuating the development of the toxicity; or iii. the cell therapy in an outpatient setting and/or without admission of the subject to the hospital overnight or for one or more consecutive days and/or is without admission of the subject to the hospital for one or more days.

In some of any such embodiments, if the assessing indicates the subject is or is likely to develop toxicity following administration of the cell therapy, the cell therapy is not administered to the subject.

In some of any such embodiments, the disease or condition is a cancer. In some examples, the cancer is a myeloma, lymphoma or leukemia. In some cases, the disease or condition is a B cell malignancy. In some instances, the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

In some of any such embodiments, greater than or greater than about 30%, 35%, 40%, or 50% of the subjects treated according to the method do not exhibit any grade of cytokine release syndrome (CRS) or neurotoxicity; and/or at least at or about 45, 50, 60, 65, 70, 75, 80, 85, 90, 95% or about 100% of subjects treated according to the method do not exhibit severe CRS, optionally grade 3 or higher, prolonged grade 3 or higher or grade 4 or 5 CRS; and/or at least at or about 45, 50, 60, 65, 70, 75, 80, 85, 90, 95% or about 100% of subjects treated according to the method do not exhibit severe neurotoxicity, optionally grade 3 or higher, prolonged grade 3 or higher or grade 4 or 5 neurotoxicity; and/or at least at or about 45, 50, 60, 65, 70, 75, 80, 85, 90, 95% or about 100% of subjects treated according to the method do not exhibit cerebral edema.

In some of any such embodiments, prior to initiation of administration of the dose of cells, the subject has not been administered an agent or treatment capable of treating, preventing, delaying, reducing or attenuating the development or risk of development of a toxicity; and/or the subject is not administered an agent or treatment for the treatment or prevention or reduction or attenuation of a neurotoxicity and/or a cytokine release syndrome or risk thereof, within a period of time following administration of the dose, which period of time is optionally at or about 1, 2, 3, 4, 5 days or is optionally at or about 6, 7, 8, 9, 10, 11 days or is optionally 1 or 2 or 3 or 4 weeks; and/or the subject is not administered an agent or treatment for the treatment or prevention or reduction or attenuation of a neurotoxicity and/or a cytokine release syndrome or risk thereof, following administration of the dose, prior to or unless the subject exhibits a sign or symptom of the toxicity and/or prior to or unless the subject exhibits a sign or symptom of the toxicity other than a fever, optionally wherein the fever is not a sustained fever or the fever is or has been reduced or reduced by more than 1° C. after treatment with an antipyretic; and/or the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

In some of any such embodiments, prior to initiation of administration of the dose of cells, the subject has not been administered an anti-IL-6 or anti-IL-6R antibody, optionally tocilizumab or siltuximab, and/or has not been administered a steroid, optionally dexamethasone, the subject is not administered an anti-IL-6 or anti-IL-6R antibody, optionally tocilizumab or siltuximab, and/or has not been administered a steroid, optionally dexamethasone, within a period of time following administration of the dose, which period of time is optionally at or about 1, 2, 3, 4, 5 days or is optionally at or about 6, 7, 8, 9, 10, 11 days or is optionally 1 or 2 or 3 or 4 weeks; and/or the subject is not administered an anti-IL-6 or anti-IL-6R antibody, optionally tocilizumab or siltuximab, and/or has not been administered a steroid, optionally dexamethasone, following administration of the cell dose, prior to, or unless, the subject exhibits a sign or symptom of a toxicity, optionally a neurotoxicity or CRS, and/or prior to, or unless, the subject exhibits a sign or symptom of a toxicity, optionally a neurotoxicity or CRS, other than a fever, optionally wherein the fever is not a sustained fever or the fever is or has been reduced or reduced by more than 1° C. after treatment with an antipyretic; and/or the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

In some of any such embodiments, the administration is carried out on an outpatient basis and/or without requiring admission to or an overnight stay at a hospital; and if the subject exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

In some of any such embodiments, the cell therapy is or contains tumor infiltrating lymphocytic (TIL) therapy. In some of any such embodiments, the cell therapy contains cells engineered to express a recombinant receptor that specifically binds to an antigen associated with a disease or condition and/or expressed in cells associated with the disease or condition. In some of any such embodiments, the cell therapy is an adoptive cell therapy. In some cases, the cells contain immune cells. In some examples, the immune cells are or contains T cells or NK cells. In some aspects, the immune cells are or contains T cells and the T cells contain CD4+ and/or CD8+ T cells.

In some of any such embodiments, the cell therapy is a T cell therapy comprising genetically engineered cells expressing a recombinant receptor. In some cases, the recombinant receptor is a T cell receptor or a functional non-T cell receptor. In some examples, the recombinant receptor specifically binds to an antigen associated with a disease or condition and/or expressed in cells associated with the disease or condition. In some examples, the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

In some embodiments, the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the CAR contains an extracellular antigen-recognition domain that specifically binds to the antigen and an intracellular signaling domain comprising an ITAM, wherein optionally, the intracellular signaling domain contains an intracellular domain of a CD3-zeta (CD35) chain; and/or wherein the CAR further contains a costimulatory signaling region, which optionally contains a signaling domain of CD28 or 4-1BB. In some aspects, the genetically engineered cells contain T cells or NK cells. In some of any such embodiments, the genetically engineered cells contain T cells, and the T cells contain CD4+ and/or CD8+ T cells. In some cases, the T cells are primary T cells obtained from a subject. In some of any such embodiments, the cells of the cell therapy are autologous to the subject. In some of any such embodiments, the cells are allogeneic to the subject. In some of any such embodiments, the threshold fold change for SPD is about 5 fold, 6 fold, 7 fold, 8 fold, or 9 fold. In some of any such embodiments, the threshold value is a threshold value for fold change of a volumetric measure of disease burden that is SPD, wherein the fold change is at least about or is about or is 5 fold, 6 fold, 7 fold, 8 fold, or 9 fold.

In some of any such embodiments, the cell therapy includes the administration of from or from about $1 \times 10^5$ to $1 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive. In some of any such embodiments, the cell therapy includes the administration of no more than $1 \times 10^8$ total recombinant receptor-expressing cells, total T cells, or total peripheral blood mononuclear cells (PBMCs), no more than $1 \times 10^7$ total recombinant receptor-expressing cells, total T cells, or total peripheral blood mononuclear cells (PBMCs), no more than $0.5 \times 10^7$ total recombinant receptor-expressing cells, total T cells, or total peripheral blood mononuclear cells (PBMCs), no more than $1 \times 10^6$ total recombinant receptor-expressing cells, total T cells, or total peripheral blood mononuclear cells (PBMCs), no more than $0.5 \times 10^6$ total recombinant receptor-expressing cells, total T cells, or total peripheral blood mononuclear cells (PBMCs).

Provided is a kit containing a cell therapy, said cell therapy comprising cells genetically engineered to express a recombinant receptor; and instructions for administering the cell therapy to a subject, wherein the instructions specify: (1) assessing one or more factors indicative of tumor burden in a subject that is a candidate for treatment with the cell therapy, wherein the assessing is performed at two time points prior to the subject receiving the cell therapy, and the factor indicative of tumor burden is a volumetric measure of the tumor or is an inflammatory marker in a sample from a subject; and (2) administering the cell therapy to the subject based on the fold change in the factor indicative of disease burden between the two time points, wherein the fold change indicates the risk or likely risk of the subject developing toxicity following administration of the cell therapy to the subject.

Also provided is a kit containing a cell therapy, said cell therapy comprising cells genetically engineered to express a recombinant receptor; and instructions for administering the cell therapy to a subject having or suspected of having a tumor, wherein the instructions specify: (1) assessing, at two different time points, one or more factors indicative of disease burden in a subject that is a candidate for treatment with the cell therapy, wherein, at each of the two time points, the subject has not yet been administered the cell therapy and the factors indicative of disease burden comprises a volumetric measure of the tumor or a level or amount of an inflammatory marker in a sample from the subject, wherein the fold change in the factor assessed at the two different time points indicates the degree of risk or likely risk of the subject developing toxicity following administration of the cell therapy to the subject; and (2) (i) if the fold change is at or below a threshold value, administering the cell therapy to the subject, or (ii) administering the cell therapy to the subject, or (iii) administering the cell therapy to the subject at an amount, dose, setting, time or frequency that is based on the fold change. In some embodiments, the kit further comprises instructions for assessing the presence, level or amount of at least one of the inflammatory marker in two or more samples obtained at two or more time points from a subject that is a candidate for treatment with the cell therapy and determining a fold-change in the level or amount of the marker assessed at two of the two or more time points, wherein the fold change indicates the degree of risk or likely risk of the subject developing toxicity following administration of the cell therapy to the subject. In some embodiments, the kit further comprises instructions for (i) administering a therapeutic regimen comprising the cell therapy to the subject if the fold change is at or below a threshold value, (ii) administering the cell therapy to the subject, or (iii) administering the therapeutic regimen to the subject at an amount, dose, setting, time or frequency based on the fold change of the at least one inflammatory marker.

Also provided is a kit containing a cell therapy, said cell therapy comprising cells genetically engineered to express a recombinant receptor; and one or more reagents for assaying one or more factor indicative of disease burden, wherein the factor indicative of disease burden is an inflammatory marker selected from C-reactive protein (CRP), erythrocyte sedimentation rate (ESR), albumin, ferritin, β2 microglobulin (β2-M), or lactate dehydrogenase (LDH). In some embodiments, the kit further includes instructions for assessing the presence, level or amount of at least one of the inflammatory marker in two or more samples obtained at two time points from a subject that is a candidate for treatment with the cell therapy and determining the fold-change in the factor between the two time points, wherein the fold change indicates the risk or likely risk of the subject developing toxicity following administration of the cell therapy to the subject. In some cases, the kit further contains instructions for administering a therapeutic regimen comprising the cell therapy to the subject following or based on the fold change of the at least one inflammatory marker.

Provided is a kit containing a cell therapy, said cell therapy comprising cells genetically engineered to express a recombinant receptor; and instructions for administering a therapeutic regimen comprising the cell therapy following or based on the results of assessing the subject for a fold change in a factor indicative of disease burden between two time points prior to receiving a cell therapy, wherein the subject is a candidate for treatment with the cell therapy. Also provided is a kit containing a cell therapy, said cell therapy comprising cells genetically engineered to express a recombinant receptor; and (b) instructions for administering a therapeutic regimen comprising the cell therapy based on the results of assessing the subject for a fold change in a factor indicative of disease burden between two time points prior to receiving a cell therapy, wherein the instructions specify (i) administering the cell therapy to the subject if the fold change is at or below a threshold value, (ii) administering the cell therapy to the subject, or (iii) administering the therapeutic regimen to the subject at an amount, dose, setting, time or frequency based on the fold change, and wherein the subject is a candidate for treatment with the cell therapy. In some aspects, the factor indicative of disease burden is a volumetric measure of a tumor or is an inflammatory marker in a sample from a subject. In some embodiments, the factor indicative of disease burden is a volumetric measure and the volumetric measure is a sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR). In some cases, the volumetric measure is measured using computed tomography (CT), positron emission tomography (PET), and/or magnetic resonance imaging (MRI) of the subject.

In some embodiments, the kit contains reagents for detecting C-reactive protein (CRP), erythrocyte sedimentation rate (ESR), albumin, ferritin, 2 microglobulin (β2-M), or lactate dehydrogenase (LDH). In some aspects, the inflammatory marker is assessed using a colorimetric assay or an immunoassay. In some examples, the inflammatory marker is assessed using an immunoassay and the immunoassay is selected from enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

In some of any such embodiments, the sample is or contains a blood sample, plasma sample, or serum sample. In some of any such embodiments, the subject is a human.

In some of any such embodiments, the two time points includes a first time point and a second time point, and wherein the fold change is a ratio of the factor indicative of disease burden at the a first time point and a second time point. In some of any such embodiments, the two time points comprises a first time point and a second time point, and wherein the fold change is a ratio of the factor indicative of disease burden at the first time point and the factor indicative of disease burden at the second time point. In some cases, if the cell therapy is to be administered to the subject, the two time points are both no more than one month or two months prior to the subject receiving the cell therapy. In some cases, the two time points are both no more than one month or two months prior to receiving the cell therapy. In some aspects, the two time points are not less than one week, two weeks, three weeks, four weeks, or five weeks apart. In some examples, the two time points are not less than three weeks apart. In some examples, the two time points are not more than four weeks apart, five weeks, or six weeks apart. In some cases, the second time point is more than 1, 2, 3, 4, 5, 6, or 7 days before administration of the cell therapy. In some cases, if the cell therapy is to be administered to the subject, the second time point is more than 1, 2, 3, 4, 5, 6, or 7 days before administration of the cell therapy.

In some of any such embodiments, the instructions specify that the fold change in the factor indicative of disease burden indicates the subject is or is likely at risk of developing toxicity if the fold change is at or above a threshold value; or the instructions specify that the fold change in the factor indicative of disease burden indicates the subject is not or is likely not at risk of developing toxicity if the fold change is below a threshold value.

In some embodiments, the threshold value is a value that i) is within 25%, within 20%, within 15%, within 10%, or within 5% above the average fold change of the factor indicative of disease burden and/or is within a standard deviation above the average fold change of the factor indicative of disease burden in a plurality of control subjects; ii) is above the highest fold change of the factor indicative of disease burden, optionally within 50%, within 25%, within 20%, within 15%, within 10%, or within 5% above such highest fold change, measured in at least one subject from among a plurality of control subjects; and/or iii) is above the highest fold change as measured among more than 75%, 80%, 85%, 90%, or 95%, or 98% of subjects from a plurality of control subjects. In some cases, the plurality of control subjects are a group of subjects prior to receiving a cell therapy for treating a disease or condition, said cell therapy containing cells genetically engineered to express a recombinant receptor, wherein each of the subjects of the group went on to develop toxicity, optionally early toxicity, optionally a fever or a sustained fever, within 7 days after receiving the cell therapy for treating the same disease or condition. In some cases, the plurality of control subjects is a group of subjects having been administered a cell therapy for treating a disease or condition and having had the fold change of the factor indicative of disease burden assessed, wherein each of the subjects of the group went on to develop toxicity, optionally early toxicity, optionally a fever or a sustained fever, within 7 days after receiving the cell therapy for treating the same disease or condition.

In some of any such embodiments, the instructions specify if the fold change indicates the subject is or is likely to develop toxicity, selecting the subject for administration of a therapeutic regimen, the therapeutic regimen comprising administering to the subject: i. an agent or other treatment capable of treating, preventing, delaying, reducing or attenuating the development or risk of development of a toxicity and the cell therapy, wherein administration of the agent is to be administered (i) prior to, (ii) within one, two, or three days of, (iii) concurrently with and/or (iv) at first fever following, the initiation of administration of the cell therapy to the subject, ii. the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or iii. the cell therapy in an in-patient setting and/or with admission to the hospital for one or more days, optionally wherein the cell therapy is otherwise to be administered to subjects on an outpatient basis or without admission to the hospital for one or more days; or iv. an alternative therapeutic treatment other than the cell therapy.

In some of any such embodiments, the instructions specify if the fold change indicates the subject is not or is likely not at risk of developing toxicity, selecting the subject for administration of a therapeutic regimen, the therapeutic regimen comprising administering to the subject: i. the cell therapy, optionally at a non-reduced dose, optionally on an outpatient basis or without admission to the hospital for one or more days; ii. the cell therapy, wherein administration of the cell therapy does not include administering, prior to or concurrently with administering the cell therapy and/or prior to the development of a sign or symptom of toxicity other than fever, an agent or treatment capable of treating, preventing, delaying, or attenuating the development of the toxicity; or iii. the cell therapy in an outpatient setting and/or without admission of the subject to the hospital overnight or for one or more consecutive days and/or is without admission of the subject to the hospital for one or more days.

In some of any such embodiments, the instructions specify if the fold change indicates the subject is or is likely to develop toxicity, the therapeutic regimen is not administered to the subject.

In some cases, the instructions specify the administration is carried out on an outpatient basis and/or without requiring admission to or an overnight stay at a hospital; and if the subject exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

In some of any such embodiments, the toxicity is neurotoxicity and/or cytokine release syndrome (CRS). In some cases, the toxicity is early toxicity, and in some aspects is early toxicity that develops within a certain number of days, such as within 7 days, of administration of the cell therapy. In some examples, the toxicity develops within 3, 4, 5, 6, or 7 days of administration of the cell therapy. In some instances, the toxicity is a first sign of a fever or is a sustained fever following administration of the cell therapy.

In some of any such embodiments, the cell therapy is or includes tumor infiltrating lymphocytic (TIL) therapy. In some of any such embodiments, the cell therapy contains cells engineered to express a recombinant receptor that specifically binds to an antigen associated with a disease or condition and/or expressed in cells associated with the disease or condition. In some cases, the cell therapy is an adoptive cell therapy. In some aspects, the cells contain immune cells. In some instances, the immune cells are or contain T cells or NK cells. In some examples, the immune cells are or contain T cells and the T cells contain CD4+ and/or CD8+ T cells. In some instances, the cell therapy is a T cell therapy comprising genetically engineered cells expressing a recombinant receptor.

In some embodiments, the disease or condition is a cancer. In some instances, the cancer is a myeloma, leukemia or lymphoma. In some aspects, the disease or condition is a B cell malignancy. In some examples, the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

In some embodiments, the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

In some embodiments, the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some of any such embodiments, the recombinant receptor is a T cell receptor or a functional non-T cell receptor. In some embodiments, the recombinant receptor is a chimeric antigen receptor (CAR). In some cases, the CAR contains an extracellular antigen-recognition domain that specifically binds to the antigen and an intracellular signaling domain comprising an ITAM, wherein optionally, the intracellular signaling domain contains an intracellular domain of a CD3-zeta (CD3ζ) chain; and/or wherein the CAR further contains a costimulatory signaling region, which optionally contains a signaling domain of CD28 or 4-1BB.

In some of any such embodiments, the kit further contains an agent or other treatment capable of treating, preventing, delaying, reducing or attenuating the development or risk of development of a toxicity. In some embodiments, the agent or other treatment is or includes one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function. In some examples, the antagonist or inhibitor is or includes an agent selected from among an antibody or antigen-binding fragment, a small molecule, a protein or peptide and a nucleic acid. In some cases, the agent or other treatment is an anti-IL-6 antibody or an anti-IL6 receptor antibody. In some examples, the agent or other treatment is or includes an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. In some instances, the agent or other treatment is or includes tocilizumab. In some cases, the agent or other treatment is or includes siltuximab. In some of any such embodiments, the steroid is or includes dexamethasone.

In some of any such embodiments, the genetically engineered cells include T cells, and the T cells contain CD4+ and/or CD8+ T cells. In some cases, the T cells are primary T cells obtained from a subject. In some embodiments, the cells of the cell therapy are autologous to the subject. In some of any such embodiments, the cells are allogeneic to the subject. In some embodiments, the threshold value for SPD is about 5 fold, 6 fold, 7 fold, 8 fold, or 9 fold. In some embodiments, the threshold value is a threshold value for fold change of a volumetric measure of disease burden that is SPD, wherein the fold change is at least about or is about or is 5 fold, 6 fold, 7 fold, 8 fold, or 9 fold.

DETAILED DESCRIPTION

Provided herein are methods of determining, assessing, and/or measuring a risk, probability, and/or likelihood of toxicity following administration of a therapy, e.g., a cell therapy, that include one or more steps for measuring, assessing, determining, and/or quantifying a fold change in one or more factors indicative of disease burden at two time points prior to treatment with the therapy, wherein the fold change indicates the risk, probability, or likelihood of the subject developing a toxicity following administration of and/or associated with the therapy. Also provided herein are methods of treatment that include one or more steps of administering to a subject a dose of a therapy, e.g. a cell therapy, for treatment of a disease or condition following and/or based on the results of assessing the fold change in the factor indicative of disease burden, wherein the fold change, when compared to a threshold value, indicates the risk, probability, or likelihood of the subject developing a toxicity following administration of and/or associated with the therapy, e.g. cell therapy.

In particular embodiments, the fold change in the factor indicative of disease burden is associated with and/or correlated to a risk, probability, and/or likelihood of developing and/or experiencing toxicity following administration of and/or associated with the therapy. In some embodiments, the factor indicative of disease burden is assessed in subject that is a candidate for receiving the therapy at two time points prior to administration of the therapy, e.g., cell therapy.

Immunotherapies, such as adoptive cell therapies (including those involving the administration of cells expressing chimeric receptors specific for a disease or disorder of interest, such as chimeric antigen receptors (CARs) and/or other recombinant antigen receptors), can be effective in treating cancer and other diseases and disorders. In certain contexts, available approaches to adoptive cell therapy may not always be entirely satisfactory. In some aspects, the provided embodiments are based on observations that the efficacy of adoptive cell therapy may be limited in some context by the development of, or risk of developing, toxicity or one or more toxic outcomes in the subject. In some cases, such toxicities can be severe. For example, in some cases, administering a dose of cells expressing a recombinant receptor, e.g. a CAR, can result in toxicity or risk thereof, such as CRS or neurotoxicity.

Predicting the risks of adverse outcomes or toxicity associated with the administration of a therapy, e.g., a cell therapy, in individual subjects is useful for evaluating, monitoring, and/or tailoring current or potential therapies for individual subjects, particularly in the context of minimizing potential life-threatening side effects (e.g., cytokine release syndrome). In some aspects, the methods provided herein may be used to minimize, mitigate, and/or avoid the risk of toxicity and other such undesirable outcomes of a therapy, e.g., a cell therapy or CAR-T cell therapy.

The provided methods are based on observations that a fold change in a factor indicative of disease burden, such as measure of tumor volume or levels or amounts of one or more inflammatory marker, in a subject prior to receiving a therapy, such as a cell therapy (e.g. CAR-T cell therapy) is associated with and/or correlates with a risk of developing toxicity following administration of the therapy. In some embodiments, the methods provided herein include one or more steps of determining a fold change in a factor indicative of disease burden, by assessing one or more factors indicative of disease burden, such as measure of tumor volume or levels or amounts of one or more inflammatory marker, at two or more different time points prior to administration of the therapy. In some aspects, the methods can be used to predict or assess the risk that a subject is at risk for developing toxicity following administration of a therapy in subjects. In some embodiments, the fold change in the factor indicative of disease burden over two time points is useful for predicting likelihood of a toxicity developing, for example CRS. In some embodiments, the fold change in the factor indicative of disease burden over two time points is useful for predicting likelihood of an early toxicity developing, for example early CRS that develops within 3, 4, 5, 6, or 7 days of administration of the therapy. In particular embodiments, the therapy is a cell therapy, such as a CAR-T cell therapy.

In certain embodiments, the one or more factors indicative of disease burden is a volumetric measure of the tumor(s). Examples of a volumetric measure of tumor(s)

includes a sum of the products of diameters (SPD), longest tumor diameters (LD), sum of longest tumor diameters (SLD), tumor volume, necrosis volume, necrosis-tumor ratio (NTR), peritumoral edema (PTE), and edema-tumor ratio (ETR). In some embodiments, the one or more factors indicative of disease burden is an inflammatory marker. Examples of inflammatory markers include, but are not limited to, C-reactive protein (CRP), erythrocyte sedimentation rate (ESR), albumin, ferritin, β2 microgulbulin (β2-M), or lactate dehydrogenase (LDH).

In some embodiments, the factor indicative of tumor burden is assessed at two time points, a fold change of the factor indicative of disease burden between two time points is determined, and the fold change is compared to a threshold fold change value. In some cases, the fold change is used to evaluate risk of developing a toxicity following administration of a therapy based on whether the fold change is above or below a threshold fold change value for the specific factor indicative of disease burden. In some embodiments, the two time points comprises a first time point and a second time point, and wherein the fold change is a ratio of the factor indicative of disease burden at the first time point and the factor indicative of disease burden at the second time point. In some cases, if the cell therapy is to be administered to the subject, the two time points are both no more than one month or two months prior to the subject receiving the cell therapy.

In some embodiments, an advantage of the methods provided herein is that a subject at risk for toxicity may be identified before the therapy is administered, so that the subject may be assigned close monitoring during and following treatment of the therapy, receive treatment of the therapy in a hospital setting, and/or in some embodiments may receive an intervention that prevents, treats, and/or ameliorates toxicity prior to receiving the therapy or before any symptoms of a toxicity are present. In certain embodiments, the at-risk subject may be selected to receive a low dose of the therapy, or in some cases, to receive an alternative therapy.

In certain embodiments, the risk, probability, and/or likelihood of toxicity following administration of or associated with the therapy is assessed in a subject with minimal invasiveness by utilizing imaging or by testing samples, such as serum samples, that are performed or collected at a screening session, such as a routine assessment or blood draw to confirm and/or identify the condition or disease in the subject. For example, in some embodiments, the imaging is performed or the sample is collected at an initial screening, such as when a treatment regimen is still being planned or considered. Thus, in some embodiments, the methods provided herein allow for the risk of toxicity following administration of a therapy to be assessed in a subject without the need for additional procedures, e.g., additional biopsies, beyond the normal procedures leading up to the therapy.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Methods of Assessing Risk of Toxicity or Toxicity-Related Outcomes

Provided herein are methods to assess, predict, infer, and/or estimate a risk of toxicity, for example to a therapy such as a cell therapy, e.g. CAR-T cell therapy. In some embodiments, the subject is administered, will be administered, or is a candidate to be administered a therapy, e.g., an immunotherapy and/or a cell therapy. In some embodiments, the toxicity is a toxicity following administration of the therapeutic treatment. In certain embodiments, the toxicity is caused by and/or associated with the therapy. In particular embodiments, methods for the assessment, prediction, inference, and/or estimate of the risk or probability include one or more steps for measuring or assessing one or more factors indicative of disease burden at two or more time points prior to administration of the therapy. In some embodiments, the method of assessing a risk of toxicity or toxicity-related outcome includes determining a fold change in the factor indicative of disease burden between the two time points. In certain embodiments, the fold change in the factor indicative of disease burden is predictive of, correlated with, and/or associated with a risk of toxicity following administration of therapy, e.g., the cell therapy. In certain embodiments, the factor indicative of disease burden is a volumetric measure of a tumor. In some embodiments, the factor indicative of disease burden is an inflammatory marker. In some aspects, the inflammatory marker is measured in a sample, e.g., a sample taken, collected, and/or obtained from the subject.

In some embodiments, the fold change in the factor indicative of disease burden, e.g., volumetric measure of the tumor or inflammatory marker, is predictive of, correlated with, and/or associated with a risk of toxicity, e.g., toxicity following administration of or associated with a therapy. In certain embodiments the toxicity is to and/or associated with a cell therapy. In certain embodiments, the fold change in the factor indicative of disease burden is indicative of risk of the subject developing an early toxicity or toxicity-related outcome, e.g., toxicity that develops within 3, 4, 5, 6, 7, or 8 days after administration of the cells therapy. In some embodiments, the toxicity is one or more outcomes associated with or related to cytokine release syndrome (CRS), including risk of developing severe CRS or grade 3 or higher CRS. In some embodiments, the toxicity is one or more outcomes that may be early indicators of development of neurotoxicity, such as risk of developing severe neurotoxicity or grade 3 or higher neurotoxicity.

In particular embodiments, the methods to assess or predict a risk of toxicity or a toxicity-related outcome, for example, to a therapy such as a cell therapy, include assessing a factor indicative of disease burden at two or more time points prior to receiving a cell therapy in a subject. In some cases, the subject receives a lymphodepleting agent prior to receiving the cell therapy, such as described in Section II, subsection E. In some embodiments, the factor is assessed at two different time points prior to when the therapy, e.g., cell therapy, is administered. In some cases, both time points are prior to administration of the lymphodepleting agent. In some embodiments, the two time points are both no more than one month or two months prior to when the therapy is administered. In some embodiments, the two time points are not less than one week, two weeks, three weeks, four weeks, or five weeks apart. In some cases, the two time points are not more than four weeks apart, five weeks, or six weeks apart. In some embodiments, the assessment of the factor indicative of tumor burden at the first time point is at a screening session, such as a routine assessment or blood draw to confirm and/or identify the condition or disease in the subject. For example, in some cases, the first time point is 3 weeks prior to the administration of the cell therapy. In some particular embodiments, the second time point is more than 1, 2, 3, 4, 5, 6, or 7 days prior to administration of the cell therapy. In some particular embodiments, if the cell therapy is to be administered to the subject, the second time point is more than 1, 2, 3, 4, 5, 6, or 7 days before administration of the cell therapy. In some embodiments, the second time point is prior to the administration of the lymphodepleting agent. In some cases, for example, the first time point is about three weeks prior to when the therapy is administered and the second time point is about 3 days prior to when the therapy is administered. In some embodiments, the method includes determining a fold change in the factor indicative of disease burden between the two time points.

In particular embodiments, provided herein are factors indicative of tumor burden correlated to and/or associated with a risk of developing a toxicity following administration of a therapy, e.g., a cell therapy. For example, in some embodiments, the factor indicative of tumor burden is a volumetric measure of the tumor(s). Examples of a volumetric measure of tumor(s) include a sum of the products of diameters (SPD), longest tumor diameters (LD), sum of longest tumor diameters (SLD), tumor volume, necrosis volume, necrosis-tumor ratio (NTR), peritumoral edema (PTE), and edema-tumor ratio (ETR). In some embodiments, the methods to assess, predict, infer, and/or estimate a risk of toxicity, include one or more steps for using a procedure such as imaging to determine tumor or tumor-related size or volume. In some cases, the factor indicative of tumor burden is an inflammatory marker, such as C-reactive protein (CRP), erythrocyte sedimentation rate (ESR), albumin, ferritin, $\beta2$ microglobulin ($\beta2$-M), or lactate dehydrogenase (LDH). In particular embodiments, the methods to assess, predict, infer, and/or estimate a risk of toxicity, include one or more steps for taking, collecting, and/or obtaining a sample from a subject; detecting, measuring, and/or obtaining a presence or level of the factor in the sample. In some cases, one or more of the methods to assess a factor indicative of disease burden can be used.

In some embodiments, the method for assaying toxicity or toxicity related outcome includes one or more steps including comparing the fold change in the factor indicative of tumor burden to a threshold fold change value for the factor. In certain embodiments, comparing the fold change in the factor indicative of tumor burden between the two time points with the threshold fold change value indicates the risk, probability, and/or likelihood that a subject will experience a toxicity following administration of the therapy if the fold change is above or below the threshold fold change value. In provided embodiments, the subject is or is likely at risk of developing toxicity if the fold change is at or above the threshold value. In provided embodiments, the subject is not or is likely not at risk of developing toxicity if the fold change is below the threshold value. In some embodiments, the sample is obtained from a subject that is administered, will be administered, or is a candidate to be administered a therapy, e.g., an immunotherapy and/or a cell therapy.

In some examples, the threshold value is a value that is within 25%, within 20%, within 15%, within 10%, or within 5% above the average fold change of the factor indicative of disease burden and/or is within a standard deviation above the average fold change of the factor indicative of disease burden in a plurality of control subjects. In some examples, the threshold value is above the highest fold change of the factor indicative of disease burden, such as within 50%, within 25%, within 20%, within 15%, within 10%, or within 5% above such highest fold change, measured in at least one subject from among a plurality of control subjects. In some examples, the threshold value is above the highest fold change as measured among more than 75%, 80%, 85%, 90%, or 95%, or 98% of subjects from a plurality of control subjects. In some cases, the plurality of control subjects are a group of subjects prior to receiving a cell therapy for treating a disease or condition, said cell therapy containing cells genetically engineered to express a recombinant receptor, wherein each of the subjects of the group went on to develop toxicity. In some cases, the plurality of control subjects is a group of subjects having been administered a cell therapy for treating a disease or condition and having had the fold change of the factor indicative of disease burden assessed, wherein each of the subjects of the group went on to develop toxicity, optionally early toxicity, optionally a fever or a sustained fever, within 7 days after receiving the cell therapy for treating the same disease or condition. In some cases, the plurality of control subjects went on to develop a toxicity that was detected or observed early or relatively early following administration of a cell therapy, such as by a fever or a sustained fever, within 7 days after receiving the cell therapy for treating the same disease or condition. In some aspects, the results of the assessing can inform or determine, such as in some cases alter, the treatment regimen the subject is to receive in connection with administration of the cell therapy.

In some cases, if the assessing indicates the subject is or is likely to develop toxicity following administration of the cell therapy, the subject may receive a therapeutic regimen that includes an agent or other treatment capable of treating, preventing, delaying, reducing or attenuating the development or risk of development of a toxicity and the cell therapy. In some embodiments, such an agent or other treatment can be administered (i) prior to, (ii) within one, two, or three days of, (iii) concurrently with and/or (iv) at first fever following, the initiation of administration of the cell therapy to the subject. In some aspects, if the assessing indicates the subject is or is likely to develop toxicity following administration of the cell therapy, the cell therapy is administered at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy. In such examples, the reduced dose or dose that is not associated with the risk of toxicity can be empirically determined, such as based on clinical studies of similarly situated patients. In some embodiments, if the assessing indicates the subject is or is likely to develop a toxicity following administration of the cell therapy, the cell therapy can be administered in an in-patient setting and/or with admission to the hospital for one or more days. In such examples, the cell therapy may be one that otherwise is typically to be administered to subjects on an outpatient basis or without admission to the hospital for one or more days. In some cases, if the assessing indicates the subject is or is likely to develop a toxicity following administration of the cell therapy, the subject may receive an alternative therapeutic treatment other than the cell therapy. In some of any such embodiments, if the assessing indicates the subject is or is likely to develop toxicity following administration of the cell therapy, the cell therapy is not administered to the subject. It is within the level of a skilled practitioner or physician to determine the appropriate regimen depending, for example, on the age or other patient specific factors of the subject being treated, the state, course or severity of the disease, the degree of likelihood the subject may or likely may develop toxicity, or the likelihood or suspected likelihood of one or more other adverse side effects of a therapy or regimen.

In some of any such embodiments, if the assessing indicates the subject is not or is likely not to develop toxicity following administration of the cell therapy, subject may receive the cell therapy, such as at its standard dose as determined for treatment of the disease or condition. In some cases, the dose is a non-reduced dose compared to the dose administered to a plurality of similarly situated subjects that have not gone on to develop a toxicity following administration of the same or similar cell therapy. In some cases, the dose is given to the subject on an outpatient basis or without admission to the hospital for one or more days. In some examples, if the assessing indicates the subject is not or is likely not to develop toxicity following administration of the cell therapy, the subject may receive the cell therapy without administering, prior to or concurrently with administering the cell therapy and/or prior to the development of a sign or symptom of toxicity other than fever, an agent or treatment capable of treating, preventing, delaying, or attenuating the development of the toxicity. In some cases, if the assessing indicates the subject is not or is likely not to develop toxicity following administration of the cell therapy, the subject may receive administration of the cell therapy in an outpatient setting and/or without admission of the subject to the hospital overnight or for one or more days, such as one or more consecutive days. It is within the level of a skilled practitioner or physician to determine the appropriate regimen depending, for example, on the age or other patient specific factors of the subject being treated, the state, course or severity of the disease, the degree of likelihood the subject may or likely may develop toxicity, or the likelihood or suspected likelihood of one or more other adverse side effects of a therapy or regimen.

A. Factors Indicative of Tumor Burden

1. Volumetric Measures of Tumor

Provided herein are methods for detecting and assessing a factor indicative of tumor burden at two time points and determining a fold change in the factor indicative of tumor burden between the two time points. In some embodiments, the factor indicative of tumor burden is a volumetric measure of tumor. In some embodiments, instructions are provided for assessing tumor or tumor related volume or size in a subject that is a candidate for treatment, optionally with a cell therapy, said cell therapy optionally including a dose or composition of genetically engineered cells expressing a recombinant receptor. Also provided is an article of manufacture containing a cell therapy containing a dose or composition of genetically engineered cells expressing a recombinant receptor, and instructions for administering the cell therapy following or based on the results of a volumetric assessment of tumor burden in the subject at two time points. In some embodiments, the volumetric measurement of the tumor in the subject is at two time points prior to administering the cell therapy. In some embodiments, the inflammatory marker is a sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR).

Also provided are methods for selecting a subject for treatment including assessing a volumetric measure of tumor in the subject. In some embodiments, the fold change in volumetric measure of tumor(s) between the two points is determined and compared to a threshold fold change value to assess risk of developing a toxicity or a toxicity-related outcome after administering the cell therapy. In some embodiments, the threshold fold change for SPD is about 5 fold, 6 fold, 7 fold, 8 fold, or 9 fold. In some embodiments, the threshold value is a threshold value for fold change of a volumetric measure of disease burden that is SPD, wherein the fold change is at least about or is about or is 5 fold, 6 fold, 7 fold, 8 fold, or 9 fold.

a. Methods for Measuring

Provided are methods of detecting and assessing one or more factors indicative of tumor burden. In some embodiments, the factor indicative of tumor burden is a volumetric measure of tumor(s). In some embodiments, the volumetric measure is a measure of the lesion(s), such as the tumor size, tumor diameter, tumor volume, tumor mass, tumor load or bulk, tumor-related edema, tumor-related necrosis, and/or number or extent of metastases. In some embodiments, the volumetric measure of tumor is a bidimensional measure. For example, in some embodiments, the area of lesion(s) are calculated as the product of the longest diameter and the longest perpendicular diameter of all measurable tumors. In some cases, the volumetric measure of tumor is a unidimensional measure. In some cases, the size of measurable lesions is assessed as the longest diameter. In some embodiments, the sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR) is measured.

In some embodiments, instructions are also provided for assessing and/or making volumetric measures of tumor in a subject that is a candidate for treatment, optionally with a cell therapy, said cell therapy optionally including a dose or composition of genetically engineered cells expressing a recombinant receptor. For methods for measuring and assessing tumor burden, see Carceller et al., Pediatr Blood Cancer. (2016) 63 (8): 1400-1406 and Eisenhauer et al., Eur J Cancer. (2009) 45 (2): 228-247. In some embodiments, the volumetric is a sum of the products of diameters (SPD) measured by determining the sum of the products of the largest perpendicular diameters of all measurable tumors. In some aspects, the tumor or lesion are measured in one dimension with the longest diameter (LD) and/or by determining the sum of longest tumor diameters (SLD) of all measurable lesions. In some embodiments, the volumetric measure of tumor is a volumetric quantification of tumor necrosis, such as necrosis volume and/or necrosis-tumor ratio (NTR), see Monsky et al., Anticancer Res. (2012) 32 (11): 4951-4961. In some aspects, the volumetric measure of tumor is a volumetric quantification of tumor-related edema, such as peritumoral edema (PTE) and/or edema-tumor ratio (ETR). In some embodiments, measuring can be performed using imaging techniques such as computed tomography (CT), positron emission tomography (PET), and/or magnetic resonance imaging (MRI) of the subject.

In some embodiments, the volumetric measure of tumor is determined at two time points prior to the administration of the therapy, e.g., cell therapy. In some embodiments, the volumetric measure of tumor is determined at a screening session, such as a routine assessment or blood draw to confirm and/or identify the condition or disease in the subject.

b. Subject

In certain embodiments, volumetric measurement of tumor is obtained from the subject at two or more time points to determine a fold change in the factor indicative of disease burden. In particular embodiments, the subject has a disease or condition and/or is suspected of having a disease or condition. In some embodiments, subject has received, will receive, or is a candidate to receive a therapy. In some embodiments, the therapy is an administration of a cell therapy. In particular embodiments, the therapy is an immunotherapy, e.g., cell therapy. In certain embodiments, the cell therapy treats and/or is capable of treating the disease or condition. In some embodiments, the therapy is a cell therapy that contains one or more engineered cells. In some embodiments, the engineered cells express a recombinant receptor. In particular embodiments, the recombinant receptor is a CAR. In particular embodiments, the sample is taken, collected, and/or obtained from a subject who has been, who will be, or is a candidate to be administered a therapy. In particular embodiments, the sample is taken, collected, and/or obtained prior to treatment or administration with the therapy, e.g., the cell therapy.

In particular embodiments, the volumetric measurement of the tumor(s) is determined a subject who has been, who will be, or is a candidate to be administered a therapy. In particular embodiments, the measurement is determined prior to treatment or administration with the therapy, e.g., the cell therapy. In accord with methods, kits and articles of manufacture described herein, the volumetric measure of tumor is associated with and/or correlate to toxicity or risk of toxicity. Exemplary volumetric measures associated with and/or correlated with a risk of developing toxicity that may be detected in a sample collected or obtained from a subject prior to receiving an immunotherapy include sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR). Thus, in some aspects, the provided methods relate to identifying subjects, prior to receiving an immunotherapy, such as a cell therapy (e.g. CAR-T cells), who may be at risk of developing a toxicity, e.g. CRS. As described elsewhere herein, the methods can be used to determine if the subject should be closely monitored following the administration of the immunotherapy, is a candidate for outpatient therapy or should receive treatment of the therapy in a hospital setting and/or is a candidate for receiving an intervention of preventing, treating or ameliorating a risk of a toxicity.

In some embodiments, the volumetric measure of a tumor is determined in a subject that has or is suspected of having a condition or disease. In some embodiments, the subject has or is suspected of having a cancer or proliferative disease. In particular embodiments, the subject has a disease or condition, or is suspected of having a disease or condition, that is associated with an antigen and/or is associated with diseased cells that express the antigen. In some embodiments, the disease or condition, e.g., a cancer or proliferative disorder, is associated with αvβ6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), Her2/neu (receptor tyrosine kinase erbB2), Her3 (erb-B3), Her4 (erb-B4), erbB dimers, human high molecular weight-melanoma-associated antigen (HMW-MAA), hepatitis B surface antigen, Human leukocyte antigen A1 (HLA-A1), human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms tumor 1 (WT-1), and/or a pathogen-specific antigen. In certain embodiments, the subject has a disease or condition, or is suspected of having a disease or condition, that is associated with CD19 and/or is associated with diseased cells that express CD19.

In some embodiments, the disease or condition, e.g., a cancer or proliferative disorder, is associated with αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the volumetric measure of tumor is determined in a subject that has or is suspected of having a cancer or proliferative disease that is a B cell malignancy or hematological malignancy. In some embodiments, the cancer or proliferative disease is a myeloma, e.g., a multiple myeloma (MM), a lymphoma or a leukemia, lymphoblastic leukemia (ALL), non-Hodgkin's lymphoma (NHL), chronic lymphocytic leukemia (CLL), a diffuse large B-cell lymphoma (DLBCL), and/or acute myeloid leukemia (AML). In some embodiments, the cancer or proliferative disorder is ALL. In some embodiments, the subject has, or is suspected of having ALL. In some embodiments, the ALL is adult ALL. In particular embodiments, the ALL is pediatric ALL.

In particular embodiments, the volumetric measure of tumor(s) in the subject is determined at two or more time points prior to administration of the therapy. In some embodiments, the volumetric measure of tumor of the subject is determined at a screening session, such as a routine assessment to confirm and/or identify the condition or disease in the subject.

2. Inflammatory Markers

Provided herein are methods for detecting and assessing a factor indicative of tumor burden at two time points and determining a fold change in the factor indicative of tumor burden between the two time points. In some embodiments, the factor indicative of tumor burden is an inflammatory marker. Also provided are articles of manufacture containing a reagent capable of detecting or that is specific for an inflammatory marker. In some embodiments, instructions are provided for assessing a biological sample for the inflammatory marker from a subject that is a candidate for treatment, optionally with a cell therapy, said cell therapy optionally including a dose or composition of genetically engineered cells expressing a recombinant receptor. Also provided are instructions for using the reagents to detect the inflammatory marker and assess the one or more inflammatory marker in a sample obtained from a subject that is a candidate for treatment, optionally with a cell therapy.

Also provided is an article of manufacture containing a cell therapy containing a dose or composition of genetically engineered cells expressing a recombinant receptor, and instructions for administering the cell therapy following or based on the results of an assessment, in a biological sample of the presence or level of inflammatory marker. In some embodiments, the biological sample is obtained from the subject prior to administering the cell therapy. In some embodiments, the inflammatory marker is C-reactive protein (CRP), erythrocyte sedimentation rate (ESR), albumin, ferritin, β2 microglobulin (β2-M), or lactate dehydrogenase (LDH). Also provided are methods for selecting a subject for treatment including contacting a biological sample (e.g. blood or serum sample) with the reagent capable of detecting or that is specific for an inflammatory marker. In some cases, the reagent is capable of detecting C-reactive protein (CRP), erythrocyte sedimentation rate (ESR), albumin, ferritin, β2 microglobulin (β2-M), or lactate dehydrogenase (LDH).

In some embodiments, the fold change in inflammatory marker(s) between the two points is determined and compared to a threshold fold change value to assess risk of developing a toxicity or a toxicity-related outcome after administering the cell therapy.

a. Reagents for Measuring

Provided herein are articles of manufacture and containing a reagent capable of detecting or that is specific for an inflammatory marker and methods for using the articles of manufacture. In some embodiments, instructions are also provided for using the reagent to assay a biological sample from a subject that is a candidate for treatment, optionally with a cell therapy, said cell therapy optionally including a dose or composition of genetically engineered cells expressing a recombinant receptor. In some embodiments of using the articles of manufacture, the level or presence of C-reactive protein (CRP), erythrocyte sedimentation rate (ESR), albumin, ferritin, β2 microglobulin (β2-M), or lactate dehydrogenase (LDH) is detected and assessed. Also provided are methods of detecting and assessing one or more inflammatory markers indicative of tumor burden.

In some embodiments, the inflammatory marker is assessed using an immune assay. For example, an enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR) can be used to detect the inflammatory marker. In some embodiments, using the articles of manufacture include detecting an inflammatory marker indicative of tumor burden. In some cases, the assaying or assessing of an inflammatory marker is using flow cytometry. In some cases, the reagent is a soluble protein that binds the inflammatory marker. In some example, the reagent is a protein that binds C-reactive protein (CRP), erythrocyte sedimentation rate (ESR), albumin, ferritin, β2 microglobulin (β2-M), or lactate dehydrogenase (LDH).

In some embodiments, C-reactive protein (CRP) is assessed using an in vitro enzyme-linked immunosorbent assay to obtain a quantitative measurement of human CRP from a sample such as serum, plasma, or blood. In some examples, CRP is detected using a human Enzyme-Linked Immunosorbent Assay (ELISA). In some embodiments, erythrocyte sedimentation rate (ESR) is assessed by measuring the distance (in millimeters per hour) that red cells have fallen after separating from the plasma in a vertical pipette or tube. In some aspects, albumin is assessed using a colorimetric test or an in vitro enzyme-linked immunosorbent assay. In some examples, albumin is detected using a human Enzyme-Linked Immunosorbent Assay (ELISA). In some embodiments, ferritin or β2 microglobulin is assessed using an immunoassay or detected using an ELISA. In some aspects, lactate dehydrogenase (LDH) is assessed using a colorimetric test or an in vitro enzyme-linked immunosorbent assay.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January;27 (1): 55-77 ("IMGT" numbering scheme); Honegger A and Plückthun A, "Yet another numbering scheme for immunoglobulin variable domains: an automatic modeling and analysis tool," J Mol Biol, 2001 Jun. 8;309 (3): 657-70, ("Aho" numbering scheme); and Martin et al., "Modeling antibody hypervariable loops: a combined algorithm," PNAS, 1989, 86 (23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1A, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1A

Boundaries of CDRs according to various numbering schemes.

| CDR | Kabat | Chothia | AbM | Contact |
| --- | --- | --- | --- | --- |
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32.34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes, although it is understood that a provided antibody can include CDRs as described according to any of the other aforementioned numbering schemes or other numbering schemes known to a skilled artisan.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the antibodies included in the provided CARs are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the Vu region; and multispecific antibodies formed from antibody fragments. In some embodiments, the antigen-binding domain in the provided CARs is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

Also provided are antibody immunoconjugates comprising an antibody against the marker expressed on a population of myeloid cells attached to a label, which can generate a detectable signal, indirectly or directly. These antibody immunoconjugates can be used for research or diagnostic applications. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}$Tc or $^{123}$I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron.

Zirconium-89 may be complexed to various metal chelating agents and conjugated to antibodies, e.g., for PET imaging (WO 2011/056983).

In some embodiments, the antibody immunoconjugate is detectable indirectly. For example, a secondary antibody that is specific for the antibody against the marker expressed on a population of myeloid cells immunoconjugate and contains a detectable label can be used to detect the antibody immunoconjugate.

In some embodiments, antibodies capable of detecting or that is specific the inflammatory markers provided herein may be identified, screened for, or characterized for their physical/chemical properties and/or biological activities by various known assays. In one aspect, the antibody is tested for its antigen binding activity, e.g., by known methods such as an immunoassay, ELISA, Western blotting, and/or flow cytometric assays, including cell-based binding assays.

b. Samples

In certain embodiments, one or more inflammatory are measured, assessed, and/or determined in one or more samples obtained at two or more time points to determine a fold change in the factor indicative of disease burden. In particular embodiments, the sample is a biological sample that is taken, collected, and/or obtained from a subject. In certain embodiments, the subject has a disease or condition and/or is suspected of having a disease or condition. In some embodiments, subject has received, will receive, or is a candidate to receive a therapy. In some embodiments, the therapy is an administration of a cell therapy. In particular embodiments, the therapy is an immunotherapy. In certain embodiments, the cell therapy treats and/or is capable of treating the disease or condition. In some embodiments, the therapy is a cell therapy that contains one or more engineered cells. In some embodiments, the engineered cells express a recombinant receptor. In particular embodiments, the recombinant receptor is a CAR. In particular embodiments, the sample is taken, collected, and/or obtained from a subject who has been, who will be, or is a candidate to be administered a therapy. In particular embodiments, the sample is taken, collected, and/or obtained prior to treatment or administration with the therapy, e.g., the cell therapy.

In particular embodiments, the sample is taken, collected, and/or obtained from a subject who has been, who will be, or is a candidate to be administered a therapy. In particular embodiments, the sample is taken, collected, and/or obtained prior to treatment or administration with the therapy, e.g., the cell therapy. In accord with methods, kits and articles of manufacture described herein, the sample can be assessed for one or more inflammatory markers that is associated with and/or correlate to toxicity or risk of toxicity. Exemplary inflammatory markers associated with and/or correlated with a risk of developing toxicity that may be detected in a sample collected or obtained from a subject prior to receiving an immunotherapy include C-reactive protein (CRP), erythrocyte sedimentation rate (ESR), albumin, ferritin, β2 microglobulin (β2-M), or lactate dehydrogenase (LDH). Thus, in some aspects, the provided methods relate to identifying subjects, prior to receiving an immunotherapy, such as a cell therapy (e.g. CAR-T cells), who may be at risk of developing a toxicity, e.g. CRS. As described elsewhere herein, the methods can be used to determine if the subject should be closely monitored following the administration of the immunotherapy, is a candidate for outpatient therapy or should receive treatment of the therapy in a hospital setting and/or is a candidate for receiving an intervention of preventing, treating or ameliorating a risk of a toxicity.

In some embodiments, the sample is taken, collected, and/or obtained from a subject that has or is suspected of having a condition or disease. In some embodiments, the subject has or is suspected of having a cancer or proliferative disease. In particular embodiments, the subject has a disease or condition, or is suspected of having a disease or condition, that is associated with an antigen and/or is associated with diseased cells that express the antigen. In some embodiments, the disease or condition, e.g., a cancer or proliferative disorder, is associated with αvβ6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), Her2/neu (receptor tyrosine kinase erbB2), Her3 (erb-B3), Her4 (erb-B4), erbB dimers, human high molecular weight-melanoma-associated antigen (HMW-MAA), hepatitis B surface antigen, Human leukocyte antigen A1 (HLA-A1), human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms tumor 1 (WT-1), and/or a pathogen-specific antigen. In certain embodiments, the subject has a disease or condition, or is suspected of having a disease or condition, that is associated with CD19 and/or is associated with diseased cells that express CD19.

In some embodiments, the disease or condition, e.g., a cancer or proliferative disorder, is associated with αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the sample is taken, collected, and/or obtained from a subject that has or is suspected of having a cancer or proliferative disease that is a B cell malignancy or hematological malignancy. In some embodiments, the cancer or proliferative disease is a myeloma, e.g., a multiple myeloma (MM), a lymphoma or a leukemia, lymphoblastic leukemia (ALL), non-Hodgkin's lymphoma (NHL), chronic lymphocytic leukemia (CLL), a diffuse large B-cell lymphoma (DLBCL), and/or acute myeloid leukemia (AML). In some embodiments, the cancer or proliferative disorder is ALL. In some embodiments, the subject has, or is suspected of having ALL. In some embodiments, the ALL is adult ALL. In particular embodiments, the ALL is pediatric ALL.

In particular embodiments, two or more samples are obtained, collected, or taken from the subject prior to administration of the therapy. In certain embodiments, the sample is a biological sample. In certain embodiments, the sample is a blood sample, plasma sample, or serum sample. In certain embodiments, the sample is a tissue sample. In some embodiments, the sample is a biopsy. In some embodiments, the sample is obtained from the subject at a screening session, such as a routine assessment or blood draw to confirm and/or identify the condition or disease in the subject.

II. Cell Therapy and Engineering Cells

In some embodiments, the cells for use in or administered in connection with the provided methods contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients, in accord with the provided methods, and/or with the provided articles of manufacture or compositions.

In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

A. Chimeric Antigen Receptors (CARs)

In some embodiments of the provided methods and uses, chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3 (4): 388-398; Davila et al. (2013) PLoS ONE 8 (4): e61338; Turtle et al., Curr. Opin. Immunol., 2012 October; 24 (5): 633-39; Wu et al., Cancer, 2012 Mar. 18 (2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35 (9): 689-701; and Brentjens et al., Sci Transl Med. 2013 5 (177). See also WO2014031687, U.S. Pat. Nos. 8,339,645, 7,446,179, US 2013/0149337, U.S. Pat. Nos. 7,446,190, and 8,389,282.

The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen or antigen binding domain is CD19. In some embodiments, the scFv contains a VH and a VL derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). Leucocyte typing III. 302). The FMC63 antibody comprises CDRH1 and H2 set forth in SEQ ID NOS: 38, 39 respectively, and CDRH3 set forth in SEQ ID NOS: 40 or 54 and CDRL1 set forth in SEQ ID NOS: 35 and CDR L2 36 or 55 and CDR L3 sequences 37 or 34. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the svFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region set forth in SEQ ID NO:41 and a variable light chain region set forth in SEQ ID NO:42. In some embodiments, the variable heavy and variable light chain are connected by a linker. In some embodiments, the linker is set forth in SEQ ID NO:56. In some embodiments, the scFv comprises, in order, a $V_H$, a linker, and a $V_L$. In some embodiments, the scFv comprises, in order, a $V_L$, a linker, and a $V_H$. In some embodiments, the svFc is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO: 43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). Leucocyte typing III. 302). The SJ25C1 antibody comprises CDRH1, H2 and H3 set forth in SEQ ID NOS: 47-49, respectively, and CDRL1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing the CDRL1 sequence of SEQ ID NO:44, a CDRL2 sequence of SEQ ID NO: 45, and a CDRL3 sequence of SEQ ID NO: 46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region set forth in SEQ ID NO:50 and a variable light chain region set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the antigen or antigen binding domain is BCMA. In some embodiments, the scFv contains a VH and a VL derived from an antibody or an antibody fragment specific to BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

In some embodiments, the antigen or antigen binding domain is GPRC5D. In some embodiments, the scFv contains a VH and a VL derived from an antibody or an antibody fragment specific to GPRC5D. In some embodiments, the antibody or antibody fragment that binds GPRC5D is or contains a VH and a VL from an antibody or antibody fragment set forth in International Patent Applications, Publication Number WO 2016/090329 and WO 2016/090312.

In some embodiments, the antigen is CD20. In some embodiments, the scFv contains a VH and a VL derived from an antibody or an antibody fragment specific to CD20. In some embodiments, the antibody or antibody fragment that binds CD20 is an antibody that is or is derived from Rituximab, such as is Rituximab scFv.

In some embodiments, the antigen is CD22. In some embodiments, the scFv contains a VH and a VL derived from an antibody or an antibody fragment specific to CD22. In some embodiments, the antibody or antibody fragment that binds CD22 is an antibody that is or is derived from m971, such as is m971 scFv.

In some embodiments, the antigen or antigen binding domain is BCMA. In some embodiments, the scFv contains a VH and a VL derived from an antibody or an antibody fragment specific to BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

In some embodiments, the antigen or antigen binding domain is GPRC5D. In some embodiments, the scFv contains a VH and a VL derived from an antibody or an antibody fragment specific to GPRC5D. In some embodiments, the antibody or antibody fragment that binds GPRC5D is or contains a VH and a VL from an antibody or antibody fragment set forth in International Patent Applications, Publication Number WO 2016/090329 and WO 2016/090312.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include, but are not limited to, those described in Hudecek et al. (2013) *Clin. Cancer Res.,* 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5. In some embodiments, the spacer has the sequence set forth in SEQ ID NOS: 27-33. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 27-33, 58, 59.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD3 transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-5) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5 (215) (December 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. An exemplary T2A linker sequence comprises the sequence of amino acids set forth in SEQ ID NO: 6 or 17 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

For example, in some embodiments, the CAR contains an antibody, e.g., an antibody fragment, such as an scFv, specific to an antigen including any as described, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, such as an scFv, specific to an antigen including any as described, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD34 (Accession No.: P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a surrogate marker (e.g., tEGFR sequence), e.g., downstream of the sequence encoding the CAR. In some embodiments, the sequence encodes a T2A ribosomal skip element set forth in SEQ ID NO: 6 or 17, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (EGFR, exemplary tEGFR sequence set forth in 7 or 16) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered to express the tEGFR construct and an encoded exogenous protein, and/or to eliminate or separate cells expressing the encoded exogenous protein. See U.S. Pat. No. 8,802,374 and Liu et al., Nature Biotech. 2016 April; 34 (4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from E. coli, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687.

In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an EGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

B. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or $C_\alpha$, typically positions 117 to 259 of the chain based on Kabat numbering or β chain constant domain or $C_\beta$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ξ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17 (12): 1236-1237, and SYFPEITHI (see Schuler et al. (2007) Immunoinformatics Methods in Molecular Biology, 409 (1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17 (12): 1236-1237 2001), and SYFPEITHI (see Schuler et al. SYFPEITHI, Database for Searching and T-Cell Epitope Prediction. in Immunoinformatics Methods in Molecular Biology, vol 409 (1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector. Genetically Engineered Cells and Methods of Producing Cells In some embodiments, the provided methods involve administering to a subject having a disease or condition cells expressing a recombinant antigen receptor. Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

C. Vectors and Methods for Genetic Engineering

Also provided are one or more polynucleotides (e.g., nucleic acid molecules) encoding recombinant receptors, vectors for genetically engineering cells to express the receptors and methods for producing the engineered cells. In some aspects, the recombinant receptor is or contains a chimeric antigen receptor (CAR). In some aspects, the recombinant receptor is or contains a T cell receptor (TCR), e.g., a transgenic TCR.

In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide set forth in SEQ ID NO: 26 and encoded by the nucleotide sequence set forth in SEQ ID NO: 25, the CD8 alpha signal peptide set forth in SEQ ID NO: 24, or the CD33 signal peptide set forth in SEQ ID NO:60.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28 (10): 1137-46; Alonso-Camino et al. (2013) Mol Ther Nucl Acids 2, e93; Park et al., Trends Biotechnol. 2011 Nov. 29 (11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35 (9): 689-701; Cooper et al. (2003) Blood. 101: 1637-1644; Verhoeyen et al. (2009) Methods Mol Biol. 506:97-114; and Cavalieri et al. (2003) Blood. 102 (2): 497-505.

In some embodiments, recombinant nucleic acids are transferred into T cells via electroporation (see, e.g., Chicaybam et al, (2013) PLoS ONE 8 (3): e60298 and Van Tedeloo et al. (2000) Gene Therapy 7 (16): 1431-1437). In some embodiments, recombinant nucleic acids are transferred into T cells via transposition (see, e.g., Manuri et al. (2010) Hum Gene Ther 21 (4): 427-437; Sharma et al. (2013) Molec Ther Nucl Acids 2, e74; and Huang et al.

(2009) Methods Mol Biol 506:115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346:776-777 (1990)); and strontium phosphate DNA co-precipitation (Brash et al., Mol. Cell Biol., 7:2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65:333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

D. Cells and Preparation of Cells for Genetic Engineering

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, CD62L+, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35 (9): 689-701. In some embodiments, combining $T_{CM}$-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L$^-$CD8$^+$ and/or CD62L$^+$CD8$^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8$^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naïve CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

E. Administration of Cell Therapy

Provided herein are methods to assess, predict, infer, and/or estimate a risk of toxicity, for example following administration of a therapy such as a cell therapy. In some embodiments, the subject is administered, will be administered, or is a candidate to be administered a therapy, e.g., an immunotherapy and/or a cell therapy. Further provided herein are methods of administering a cell therapy, such as methods of selecting a subject and administering a dose of cell therapy, wherein the subject is selected based on the risk, probability, and/or likelihood of toxicity.

In certain embodiments, the methods include steps to assess, determine, measure, and/or quantify a risk, probability, and/or likelihood that a subject will experience and/or develop a toxicity following administration of or associated with a cell therapy. In some embodiments, the subject's risk, probability, and/or likelihood of experiencing or developing the toxicity is assessed, determined, measured and/or quantified by a method of assessing a factor indicative of tumor burden, such as described herein. In particular embodiments, the subject is determined to have a low, reduced, and/or decreased risk, probability and/or likelihood of toxicity, and the subject is administered a standard dose of a cell therapy. In certain embodiments, the subject is determined to have a high, elevated, or increased risk of toxicity, and the subject is administered a dose of a cell therapy that is less than a standard dose of the cell therapy. In particular embodiments, the subject is determined to have a high, elevated, or increased risk of toxicity, and the subject is administered a standard dose of a cell therapy and an intervention, such as any as described herein. In certain embodiments, the subject is determined to have a high, elevated, or increased risk of toxicity, and the subject is administered a dose of a cell therapy that is lower than the standard dose of the cell therapy and an intervention, such as any as described herein.

1. Methods of Treatment

In certain embodiments of the methods provided herein, the subject is administered a standard dose of a therapy, e.g., an immunotherapy or a cell therapy. In certain embodiments, the risk, probability, and/or likelihood that the subject will experience and/or develop a toxicity following administration of or associated with the cell therapy is determined by one or more methods of assessing a factor indicative of tumor burden, such as provided herein, e.g. in Section I. In certain embodiments, the subject is determined to be unlikely, or to have a low risk, probability, and/or likelihood, of developing a toxicity, e.g., CRS or neurotoxicity, by performing one or more methods as described, such as provided in Section I, and the subject is administered a standard dose of the cell therapy. In particular embodiments, the subject is administered a reduced dose of the therapeutic cell composition. In some embodiments, the subject is determined to have a high, elevated, and/or an increased risk, probability, and/or likelihood of developing a toxicity, e.g., a neurotoxicity, and the subject is administered a reduced dose of the therapeutic cell composition. In some embodiments, the cell therapy is a T cell therapy. In some embodiments, the T cell therapy contains cells that express a recombinant receptor. In some embodiments, the recombinant receptor is a CAR.

The disease or condition that is treated in some aspects can be any in which expression of an antigen is associated with, specific to, and/or expressed on a cell or tissue of a disease, disorder or condition and/or involved in the etiology of a disease, condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the immunomodulatory polypeptide and/or recombinant receptor, e.g., the chimeric antigen receptor or TCR, specifically binds to an antigen associated with the disease or condition. In some embodiments, the subject has a disease, disorder or condition, optionally a cancer, a tumor, an autoimmune disease, disorder or condition, or an infectious disease.

In some embodiments, the disease, disorder or condition includes tumors associated with various cancers. The cancer can in some embodiments be any cancer located in the body of a subject, such as, but not limited to, cancers located at the head and neck, breast, liver, colon, ovary, prostate, pancreas, brain, cervix, bone, skin, eye, bladder, stomach, esophagus, peritoneum, or lung. For example, the anti-cancer agent can be used for the treatment of colon cancer, cervical cancer, cancer of the central nervous system, breast cancer, bladder cancer, anal carcinoma, head and neck cancer, ovarian cancer, endometrial cancer, small cell lung cancer, non-small cell lung carcinoma, neuroendocrine cancer, soft tissue carcinoma, penile cancer, prostate cancer, pancreatic cancer, gastric cancer, gall bladder cancer or espohageal cancer. In some cases, the cancer can be a cancer of the blood. In some embodiments, the disease, disorder or condition is a tumor, such as a solid tumor, lymphoma, leukemia, blood tumor, metastatic tumor, or other cancer or tumor type. In some embodiments, the disease, disorder or condition is selected from among cancers of the colon, lung, liver, breast, prostate, ovarian, skin, melanoma, bone, brain cancer, ovarian cancer, epithelial cancers, renal cell carcinoma, pancreatic adenocarcinoma, cervical carcinoma, colorectal cancer, glioblastoma, neuroblastoma, Ewing sarcoma, medulloblastoma, osteosarcoma, synovial sarcoma, and/or mesothelioma.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM), a B cell malignancy is selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), ephrine receptor A2 (EPHa2), Her2/neu (receptor tyrosine kinase erb-B2), Her3 (erb-B3), Her4 (erb-B4), erbB dimers, type III epidermal growth factor receptor mutation (EGFR VIII), folate binding protein (FBP), FCRL5, Fc receptor like 5 (FCRL5; also known as Fc receptor homolog 5 or FCRH5), fetal acetylcholine receptor, ganglioside GD2, ganglioside GD3, G Protein Coupled Receptor 5D (GPCR5D), HMW-MAA, IL-22R-alpha, IL-13R-alpha2, kinase insert domain receptor (kdr), kappa light chain, Leucine Rich Repeat Containing 8 Family Member A (LRRC8A), Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, Human leukocyte antigen A1 (HLA-A1), MAGE A1, HLA-A2, NY-ESO-1, PSCA, folate receptor-a, CD44v6, CD44v7/8, αvβ6 integrin (avb6 integrin), 8H9, NCAM, VEGF receptors, 5T4, Foetal AchR, natural killer group 2 member D (NKG2D) ligands, CD44v6, dual antigen, a cancer-testes antigen, mesothelin, murine CMV, mucin 1 (MUC1), MUC16, prostate stem cell antigen (PSCA), NKG2D, a cancer-testis antigen cancer/testis antigen 1B (CTAG, also known as NY-ESO-1 and LAGE-2), MART-1, glycoprotein 100 (gp100), oncofetal antigen, ROR1, Trophoblast glycoprotein (TPBG also known as 5T4), TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, C—C Motif Chemokine Ligand 1 (CCL-1), CD138, a pathogen-specific antigen and an antigen associated with a universal tag, and/or biotinylated molecules, and/or molecules expressed by HIV, HCV, HBV or other pathogens.

In some embodiments, the disease or condition is a B cell malignancy. In some embodiments, the B cell malignancy is a leukemia or a lymphoma. In some aspects, the disease or condition is acute lymphoblastic leukemia (ALL), adult ALL, chronic lymphoblastic leukemia (CLL), non-Hodgkin lymphoma (NHL), or Diffuse Large B-Cell Lymphoma (DLBCL). In some cases, the disease or condition is an NHL, such as or including an NHL that is an aggressive NHL, diffuse large B cell lymphoma (DLBCL), NOS (de novo and transformed from indolent), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL), optionally, follicular lymphoma Grade 3B (FL3B). In some aspects, the recombinant receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30, or combinations thereof.

In some embodiments, the disease or condition is a myeloma, such as a multiple myeloma. In some aspects, the recombinant receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma. In some aspects, the antigen, e.g., the second or additional antigen, such as the disease-specific antigen and/or related antigen, is expressed on multiple myeloma, such as B cell maturation antigen (BCMA), G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the antigen is a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al., (2013) Nat Biotechnol. 31(10): 928-933; Tsukahara et al., (2013) Biochem Biophys Res Commun 438(1): 84-9; Davila et al., (2013) PLoS ONE 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In certain embodiments, if the risk, probability, and/or likelihood that the subject will experience and/or develop a toxicity following administration of or associated with the cell therapy is determined to be high, increased, or elevated by one or more methods as described herein, then the subject is administered the cell therapy in an in-patient setting and/or with admission to the hospital for one or more days, optionally wherein the cell therapy is otherwise to be administered to subjects on an outpatient basis or without admission to the hospital for one or more days if the risk, probability, and/or likelihood of is determined to be low, reduced, or decreased according to the results of a method as described herein. In particular embodiments, a cell therapy, optionally at a non-reduced dose, optionally on an outpatient basis or without admission to the hospital for one or more days, is administered to the subject that is determined to have a low, decreased, and/or reduced risk of toxicity according to the results of a method provided herein, such as described in Section I.

In certain embodiments, if the risk, probability, and/or likelihood that the subject will experience and/or develop a toxicity following administration of or associated with the cell therapy is determined to be high, increased, or elevated by one or more methods provided in Section I, then the subject is administered a standard dose of the cell therapy in an in-patient setting and/or with admission to the hospital for one or more days. In particular embodiments, if the risk, probability, and/or likelihood that the subject will experience and/or develop a toxicity following administration of or associated with the cell therapy is determined to be high, increased, or elevated by one or more methods as described herein, then the subject is administered a reduced dose of the cell therapy in an in-patient setting and/or with admission to the hospital for one or more days. In certain embodiments, if the risk, probability, and/or likelihood that the subject will experience and/or develop a toxicity following administration of or associated with the cell therapy is determined to be low, decreased, or reduced by one or more methods as described herein, then the subject is administered a standard dose of the cell therapy on an outpatient basis or without admission to the hospital for one or more days.

In certain embodiments, if the risk, probability, and/or likelihood that the subject will experience and/or develop a toxicity following administration of and/or associated with the cell is determined to be high, increased, or elevated by one or more methods as described herein, then the subject is not administered the cell therapy. In such embodiments, the subject may be administered an alternative therapy, such as a different cell therapy, or an immunotherapy.

In some embodiments, subjects with low, decreased, and/or reduced risk, probability, and/or likelihood to experience and/or develop a toxicity as determined by one or more methods as described herein, are administered a standard dose of the cell therapy. In some embodiments, subjects with high, increased, or elevated risk, probability, and/or likelihood to experience and/or develop a toxicity as determined by one or more methods as described herein, are administered a reduced dose of the cell therapy. In some embodiments, subjects with high, increased, or elevated risk, probability, and/or likelihood to experience and/or develop a toxicity as determined by one or more methods as described herein, are administered a standard dose of the cell therapy and an intervention to prevent or reduce toxicity as described herein. In particular embodiments, subjects with high, increased, or elevated risk, probability, and/or likelihood to experience and/or develop a toxicity as determined by one or more methods as described herein, are administered a reduced dose of the cell therapy and an intervention to prevent or reduce toxicity as described herein.

In some embodiments, more than 30%, more than 35%, more than 40%, more than 45%, more than 50%, more than 55%, more than 60%, more than 65%, more than 70%, more than 85%, more than 90%, more than 97%, more than 99%, or about 100% of the subjects do not develop or experience severe toxicity. In some embodiments, the severe toxicity is severe CRS of grade 3 or higher, grade 4 or higher, or grade 5. In some embodiments, the severe toxicity is severe neurotoxicity of grade 3 or higher, extended grade 3 or higher, grade 4 or higher, or grade 5.

In some embodiments, at least 30%, at least 35%, at least 40%, at least 45%, at least 50%, at least 55%, at least 60%, at least 65%, at least 70%, at least 85%, at least 90%, at least 97%, at least 99%, or about 100% of the subjects treated according to the provided methods do not develop or experience early toxicity. In some embodiments, early toxicity is a toxicity developed in the subject by less than eight, seven, six, five, four or three days after initiation of the administration of the cell therapy. In some instances, CRS, such as severe CRS, typically occurs 6-20 days after infusion of cells that express a CAR. See Xu et al., Cancer Letters 343 (2014) 172-78. In some cases, the onset of CRS occurs less than or by 4 days after administration of the cell therapy.

In certain embodiments, a reduced dose of a therapeutic cell composition contains less than or equal to 90%, less than or equal to 80%, less than or equal to 70%, less than or equal to 60%, less than or equal to 50%, less than or equal to 40%, less than or equal to 30%, less than or equal to 20%, or less than or equal to 10%, or less than or equal to 1%, less than or equal to 0.1%, or less than or equal to 0.01% of the total amount of cells, CAR+ cells, CAR+CD4+ cells, and/or CD8+CAR+ cells of a standard dose of the therapeutic cell composition. In some embodiments, a reduced dose of a therapeutic cell composition contains less than or equal to 90%, less than or equal to 80%, less than or equal to 70%, less than or equal to 60%, less than or equal to 50%, less than or equal to 40%, less than or equal to 30%, less than or equal to 20%, or less than or equal to 10%, or less than or equal to 1%, less than or equal to 0.1%, or less than or equal to 0.01% of the amount of CAR+ cells of a standard dose of the therapeutic cell composition total amount of cells per kg of subject body weight, CAR+ cells per kg of subject body weight, CAR+CD4+ cells per kg of subject body weight, and/or CD8+CAR+ cells per kg of subject body weight.

In some embodiments, the methods include administration of the engineered cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell-based therapy is or comprises administration of cells, such as T cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m2 and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

In some embodiments, the provided methods include one or more steps of administering to a subject cells therapeutic cell composition, such as a composition of cells described herein, e.g. in Section II. In certain embodiments, the cells of the therapeutic cell composition include engineered CD4$^+$ T cells and engineered CD8$^+$ T cells. In some embodiments, the engineered CD4+ and CD8$^+$ T cells express a T cell receptor (TCR) or other antigen-binding receptor. In some embodiments, the immune cells express a recombinant receptor, such as a transgenic TCR or a chimeric antigen receptor (CAR). In some embodiments, the cells of the therapeutic cell composition are autologous to the subject. In some embodiments, the cells are allogeneic to the subject.

In certain embodiments, the CD4$^+$ T cells and CD8$^+$ T cells of the therapeutic cell composition are administered to the subject in the same composition, dose, or mixture. Thus, in some embodiments, the recombinant receptor expressing CD4$^+$ T cells and recombinant receptor expressing CD8$^+$ T cells, e.g., CAR+CD4+ and CAR+CD8+ are administered to the subject in the same composition, dose, or mixture.

2. Dosing

In certain embodiments, if the risk, probability, and/or likelihood that the subject will experience and/or develop a toxicity following administration of or associated with the cell therapy is determined to be high, increased, or elevated by one or more of the methods provided, e.g. as described in Section I, then the subject is administered a reduced dose of the cell therapy. In certain embodiments, if the risk, probability, and/or likelihood that the subject will experience and/or develop a toxicity following administration of or associated with the cell therapy is determined to be low, reduced, or decreased by one or more of the methods provided, e.g. as described in Section I, then the subject is administered a standard dose of the cell therapy.

In some embodiments, a reduced dose is less than or equal to 90%, 85%, 80%, 75%, 70%, 65%, 60%, 55%, 50%, 45%, 40%, 35%, 30%, 25%, 20%, 15%, 10%, 5%, 3%, 1%, 0.5%, 0.1%, 0.05%, 0.01%, 0.001%, or 0.0001% of a standard dose.

In certain embodiments, a reduced dose of a therapeutic cell composition contains less than or equal to 90%, less than or equal to 80%, less than or equal to 70%, less than or equal to 60%, less than or equal to 50%, less than or equal to 40%, less than or equal to 30%, less than or equal to 20%, or less than or equal to 10%, or less than or equal to 1%, less than or equal to 0.1%, or less than or equal to 0.01% of the total amount of cells, CAR+ cells, CAR+CD4+ cells, and/or CD8+CAR+ cells of a standard dose of the therapeutic cell composition. In some embodiments, a reduced dose of a therapeutic cell composition contains less than or equal to 90%, less than or equal to 80%, less than or equal to 70%, less than or equal to 60%, less than or equal to 50%, less than or equal to 40%, less than or equal to 30%, less than or equal to 20%, or less than or equal to 10%, or less than or equal to 1%, less than or equal to 0.1%, or less than or equal to 0.01% of the amount of CAR+ cells of a standard dose of the therapeutic cell composition total amount of cells per kg of subject body weight, CAR+ cells per kg of subject body weight, CAR+CD4+ cells per kg of subject body weight, and/or CD8+CAR+ cells per kg of subject body weight.

In some embodiments, the standard dose of cells comprises between at or about $2 \times 10^5$ of the cells/kg and at or about $2 \times 10^6$ of the cells/kg, such as between at or about $4 \times 10^5$ of the cells/kg and at or about $1 \times 10^6$ of the cells/kg or between at or about $6 \times 10^5$ of the cells/kg and at or about $8 \times 10^5$ of the cells/kg. In some embodiments, the standard dose of cells comprises no more than $2 \times 10^5$ of the cells (e.g. antigen-expressing, such as CAR-expressing cells) per kilogram body weight of the subject (cells/kg), such as no more than at or about $3 \times 10^5$ cells/kg, no more than at or about $4 \times 10^5$ cells/kg, no more than at or about $5 \times 10^5$ cells/kg, no more than at or about $6 \times 10^5$ cells/kg, no more than at or about $7 \times 10^5$ cells/kg, no more than at or about $8 \times 10^5$ cells/kg, no more than at or about $9 \times 10^5$ cells/kg, no more than at or about $1 \times 10^6$ cells/kg, or no more than at or about $2 \times 10^6$ cells/kg. In some embodiments, the standard dose of cells comprises at least or at least about or at or about $2 \times 10^5$ of the cells (e.g. antigen-expressing, such as CAR-expressing cells) per kilogram body weight of the subject (cells/kg), such as at least or at least about or at or about $3 \times 10^5$ cells/kg, at least or at least about or at or about $4 \times 10^5$ cells/kg, at least or at least about or at or about $5 \times 10^5$ cells/kg, at least or at least about or at or about $6 \times 10^5$ cells/kg, at least or at least about or at or about $7 \times 10^5$ cells/kg, at least or at least about or at or about $8 \times 10^5$ cells/kg, at least or at least about or at or about $9 \times 10^5$ cells/kg, at least or at least about or at or about $1 \times 10^6$ cells/kg, or at least or at least about or at or about $2 \times 10^6$ cells/kg.

In certain embodiments, the cells are administered to the subject at a standard dose. In particular embodiments, the standard dose is or contains a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $5 \times 10^8$ total recombinant receptor (e.g., CAR)-expressing cells, T cells, or peripheral blood mononuclear cells (PBMCs). In some embodiments, for example, where the subject is a human, the standard dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values.

In some embodiments, the dose of genetically engineered cells comprises from or from about $1 \times 10^5$ to $5 \times 10^8$ total CAR-expressing T cells, $1 \times 10^5$ to $2.5 \times 10^8$ total CAR-expressing T cells, $1 \times 10^5$ to $1 \times 10^8$ total CAR-expressing T cells, $1 \times 10^5$ to $5 \times 10^7$ total CAR-expressing T cells, $1 \times 10^5$ to $2.5 \times 10^7$ total CAR-expressing T cells, $1 \times 10^5$ to $1 \times 10^7$ total CAR-expressing T cells, $1 \times 10^5$ to $5 \times 10^6$ total CAR-expressing T cells, $1 \times 10^5$ to $2.5 \times 10^6$ total CAR-expressing T cells, $1 \times 10^5$ to $1 \times 10^6$ total CAR-expressing T cells, $1 \times 10^6$ to $5 \times 10^8$ total CAR-expressing T cells, $1 \times 10^6$ to $2.5 \times 10^8$ total CAR-expressing T cells, $1 \times 10^6$ to $1 \times 10^8$ total CAR-expressing T cells, $1 \times 10^6$ to $5 \times 10^7$ total CAR-expressing T cells, $1 \times 10^6$ to $2.5 \times 10^7$ total CAR-expressing T cells, $1 \times 10^6$ to $1 \times 10^7$ total CAR-expressing T cells, $1 \times 10^6$ to $5 \times 10^6$ total CAR-expressing T cells, $1 \times 10^6$ to $2.5 \times 10^6$ total CAR-expressing T cells, $2.5 \times 10^6$ to $5 \times 10^8$ total CAR-expressing T cells, $2.5 \times 10^6$ to $2.5 \times 10^8$ total CAR-expressing T cells, $2.5 \times 10^6$ to $1 \times 10^8$ total CAR-expressing T cells, $2.5 \times 10^6$ to $5 \times 10^7$ total CAR-expressing T cells, $2.5 \times 10^6$ to $2.5 \times 10^7$ total CAR-expressing T cells, $2.5 \times 10^6$ to $1 \times 10^7$ total CAR-expressing T cells, $2.5 \times 10^6$ to $5 \times 10^6$ total CAR-expressing T cells, $5 \times 10^6$ to $5 \times 10^8$ total CAR-expressing T cells, $5 \times 10^6$ to $2.5 \times 10^8$ total CAR-expressing T cells, $5 \times 10^6$ to $1 \times 10^8$ total CAR-expressing T cells, $5 \times 10^6$ to $5 \times 10^7$ total CAR-expressing T cells, $5 \times 10^6$ to $2.5 \times 10^7$ total CAR-expressing T cells, $5 \times 10^6$ to $1 \times 10^7$ total CAR-expressing T cells, $1 \times 10^7$ to $5 \times 10^8$ total CAR-expressing T cells, $1 \times 10^7$ to $2.5 \times 10^8$ total CAR-expressing T cells, $1 \times 10^7$ to $1 \times 10^8$ total CAR-expressing T cells, $1 \times 10^7$ to $5 \times 10^7$ total CAR-expressing T cells, $1 \times 10^7$ to $2.5 \times 10^7$ total CAR-expressing T cells, $2.5 \times 10^7$ to $5 \times 10^8$ total CAR-expressing T cells, $2.5 \times 10^7$ to $2.5 \times 10^8$ total CAR-expressing T cells, $2.5 \times 10^7$ to $1 \times 10^8$ total CAR-expressing T cells, $2.5 \times 10^7$ to $5 \times 10^7$ total CAR-expressing T cells, $5 \times 10^7$ to $5 \times 10^8$ total CAR-expressing T cells, $5 \times 10^7$ to $2.5 \times 10^8$ total CAR-expressing T cells, $5 \times 10^7$ to $1 \times 10^8$ total CAR-expressing T cells, $1 \times 10^8$ to $5 \times 10^8$ total CAR-expressing T cells, $1 \times 10^8$ to $2.5 \times 10^8$ total CAR-expressing T cells, or $2.5 \times 10^8$ to $5 \times 10^8$ total CAR-expressing T cells.

In some embodiments, the dose of genetically engineered cells comprises at least or at least about $1 \times 10^5$ CAR-expressing cells, at least or at least about $2.5 \times 10^5$ CAR-expressing cells, at least or at least about $5 \times 10^5$ CAR-expressing cells, at least or at least about $1 \times 10^6$ CAR-expressing cells, at least or at least about $2.5 \times 10^6$ CAR-expressing cells, at least or at least about $5 \times 10^6$ CAR-expressing cells, at least or at least about $1 \times 10^7$ CAR-expressing cells, at least or at least about $2.5 \times 10^7$ CAR-expressing cells, at least or at least about $5 \times 10^7$ CAR-expressing cells, at least or at least about $1 \times 10^8$ CAR-expressing cells, at least or at least about $2.5 \times 10^8$ CAR-expressing cells, or at least or at least about $5 \times 10^8$ CAR-expressing cells.

In some embodiments, the cell therapy comprises administration of a dose comprising a number of cell from or from about $1 \times 10^5$ to $5 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1 \times 10^5$ total recombinant receptor-expressing cells, total T cells, or total peripheral blood mononuclear cells (PBMCs), such at least or at least $1 \times 10^6$, at least or at least about $1 \times 10^7$, at least or at least about $1 \times 10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1 \times 10^5$ to $5 \times 10^8$ CD3+ or CD8+ total T cells or CD3+ or CD8+ recombinant receptor-expressing cells, from or from about $5 \times 10^5$ to $1 \times 10^7$ CD3+ or CD8+ total T cells or CD3+ or CD8+ recombinant receptor-expressing cells, or from or from about $1 \times 10^6$ to $1 \times 10^7$ CD3+ or CD8+ total T cells or CD3+ or CD8+ recombinant receptor-expressing cells, each inclusive. In some embodiments, the cell therapy comprises administration of a dose comprising a number of cell from or from about $1 \times 10^5$ to $5 \times 10^8$ total CD3+/CAR+ or CD8+/CAR+ cells, from or from about $5 \times 10^5$ to $1 \times 10^7$ total CD3+/CAR+ or CD8+/CAR+ cells, or from or from about $1 \times 10^6$ to $1 \times 10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1 \times 10^6$ and $5 \times 10^8$ total recombinant receptor (e.g., CAR)-expressing CD8+ cells, e.g., in the range of about $5 \times 10^6$ to $1 \times 10^8$ such cells, such cells $1 \times 10^7$, $2.5 \times 10^7$, $5 \times 10^7$, $7.5 \times 10^7$, $1 \times 10^8$, or $5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to $0.75 \times 10^8$ total recombinant receptor-expressing CD8+ T cells, $1 \times 10^7$ to $2.5 \times 10^7$ total recombinant receptor-expressing CD8+ T cells, from or from about $1 \times 10^7$ to $0.75 \times 10^8$ total recombinant receptor-expressing CD8+ T cells, each inclusive. In some embodiments, the dose of cells comprises the administration of or about $1 \times 10^7$, $2.5 \times 10^7$, $5 \times 10^7$ $7.5 \times 10^7$, $1 \times 10^8$, or $5 \times 10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some aspects, the pharmaceutical compositions and formulations are provided as unit dose form compositions including the number of cells for administration in a given dose or fraction thereof. In some embodiments, the provided methods produce cells in a predictable timeline to dosing as compared to other methods of incubating (e.g., stimulating) cells. In some cases, the dose of cells for administration is determined based on the number of naïve-like cells in the input cell composition. In some embodiments, the unit dose is a standard dose.

In some aspects, the size of a dose, e.g., standard dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent standard dose is inversely correlated with disease burden. In some aspects, as in the context of a large disease burden, the subject is administered a low number of cells. In other embodiments, as in the context of a lower disease burden, the subject is administered a larger number of cells.

In some aspects, the size of the standard dose is determined by the subject's risk for toxicity, e.g., as assessed by the fold change in a factor indicative of disease burden. In some aspects, the number of cells administered in the dose is determined based on the fold change in a factor indicative of disease burden between a first time point and a second time point prior to administration of the therapy. In some embodiments, the size of the first and/or subsequent dose is inversely correlated with the risk for toxicity. In some aspects, as in the context of a likelihood and/or elevated risk or probability of toxicity, the subject is administered a low number of cells. In other embodiments, as in the context of a lower risk or probability, the subject is administered a larger number of cells.

In some aspects, the size of the standard dose is determined by the activity of the cells of the cell therapy, e.g., as determined by measuring one or more parameters of the cell therapy. In some aspects, the number of cells administered in the dose is determined based on the activity of the cells of the cell therapy. In some embodiments, the size of the first and/or subsequent dose is inversely correlated with the amount or level of activity in the cells. In particular embodiments, the number of cells administered in the dose is determined by the activity of the cells of the cell therapy and the risk of the subject for a toxicity. In certain embodiments, the subject is administered a standard dose of the cell therapy if the cells have a low or moderate activity as determined by measuring the one or more parameters, regardless of the risk assessment provided by the fold change in a factor indicative of disease burden in the subject.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include $CD8^+$ and $CD4^+$ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+ CD4+:CAR+ CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or anti-tumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the cells are administered as part of a further combination treatment, such as simultaneously with or sequentially with, in any order, another therapeutic intervention, such as an antibody or engineered cell or receptor or agent, such as a cytotoxic or therapeutic agent. For example, in some embodiments, an anti-cancer agent or immunomodulatory agent can be used in combination therapy with adoptive cell therapy with engineered cell expressing a recombinant receptor, e.g. a CAR. In some contexts, the cells are co-administered with another therapy sufficiently close in time such that the cell populations enhance the effect of the P one or more additional therapeutic agents, or vice versa. In some embodiments, the cells are administered prior to the one or more additional therapeutic agents. In some embodiments, the cells are administered after the one or more additional therapeutic agents.

In some embodiments, the one or more additional therapeutic agents include a cytokine, such as IL-2, for example, to enhance persistence. In some embodiments, the methods comprise administration of a chemotherapeutic agent. In some embodiments, the one or more additional therapeutic agents include one or more lymphodepleting therapies, such as prior to or simultaneous with initiation of administration of the engineered cells. In some embodiments, the lymphodepleting therapy comprises administration of a phosphamide, such as cyclophosphamide. In some embodiments, the lymphodepleting therapy can include administration of fludarabine. In some embodiments, fludarabine is excluded in the lymphodepleting therapy. In some embodiments, a lymphodepleting therapy is not administered.

In some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m2, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m2, such as between or between about 10 mg/m$^2$ and 75 mg/m$^2$, 15 mg/m$^2$ and 50 mg/m$^2$, 20 mg/m2 and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

The cells can be administered by any suitable means. The cells are administered in a dosing regimen to achieve a therapeutic effect, such as a reduction in tumor burden. Dosing and administration may depend in part on the schedule of administration of the immunomodulatory compound, which can be administered prior to, subsequent to and/or simultaneously with initiation of administration of the T cell therapy. Various dosing schedules of the T cell therapy include but are not limited to single or multiple administrations over various time-points, bolus administration, and pulse infusion. In certain embodiments, the engineered T cells express a recombinant receptor. In certain embodiments, the engineered T cells express a CAR.

In particular embodiments, the ratio of the CD4+ T cells to CD8+ T cells that are administered to the subject in the same composition, dose, or mixture is between 5:1 to 0.2:1, between 4:1 to 0.25:1, between 3:1 to 0.33:1, between 2:1 to 0.5:1, between 1.5:1 to 0.66:1, or between 1.25:1 to 0.8:1. In some embodiments, the ratio of CD4+ T cells to CD8+ T cells administered to the subject in the same composition, dose, or mixture is or is about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1.

In particular embodiments, the ratio of recombinant receptor expressing CD4+ T cells to recombinant receptor expressing CD8+ T cells that are administered to the subject in the same composition, dose, or mixture is between 5:1 to 0.2:1, between 4:1 to 0.25:1, between 3:1 to 0.33:1, between 2:1 to 0.5:1, between 1.5:1 to 0.66:1, or between 1.25:1 to 0.8:1. In certain embodiments, the ratio of recombinant receptor expressing CD4+ T cells to recombinant receptor expressing CD8+ T cells that are administered to the subject in the same composition, dose, or mixture is or is about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1. In particular embodiments, ratio of the administered recombinant receptor expressing CD4+ T cells to recombinant receptor expressing CD8+ T cells is or is about 1:1. In some embodiments, the recombinant receptor is a TCR or a CAR. In particular embodiments, the recombinant receptor is a CAR.

In some embodiments, the ratio of engineered CD4+ T cells to engineered CD8+ T cells of the dose, composition, or mixture that is administered to the subject is within a certain tolerated difference or range of error of such a defined, desired, or fixed ratio. In some embodiments, the tolerated difference is within of or of about 1%, 2%, 3%, 4%, 5%, 10%, 15%, 20%, 25%, 30%, 35%, 40%, 45%, or 50%, of the target, defined, preferred, and/or fixed ratio.

In some embodiments, a composition of cells produced by the methods provided herein, e.g., an output composition, having a ratio of engineered CD4+ T cells to engineered CD8+ T cells of between 2:1 and 0.5:1 is administered to a subject in a single composition, dose, or mixture. In certain embodiments, the composition contains a ratio of engineered CD4+ T cells to engineered CD8+ T cells of or of about 1:1. In some embodiments, a cell composition produced from an input cell composition, e.g., an input cell composition described in Section I-A1, has a ratio of engineered CD4+ T cells to engineered CD8+ T cells of between 2:1 and 0.5:1 and is administered to a subject in a single composition, dose, or mixture. In particular embodiments, the cell composition produced from an input cell composition has a ratio of engineered CD4+ T cells to engineered CD8+ T cells of 1:1 with a tolerated difference of 50%, 25%, 10%, or less.

III. Toxicity and Interventions or Agents that Treat or Ameliorate Symptoms of Toxicity In some aspects, the provided embodiments are based on observations that the certain pre-treatment factors can be used to assess and monitor a risk of a subject developing a toxicity to a therapy, such as a cell therapy, e.g. CAR-T cells. In some aspects, the methods can improve efficacy of a therapy, e.g., a cell therapy, which otherwise may be limited by the development of toxicity, in some cases severe toxicity, in the subject to whom such cells are administered. For example, in some cases, administering a dose of cells expressing a recombinant receptor, e.g. a CAR, can result in toxicity or risk thereof, such as CRS or neurotoxicity. In some cases, while a higher dose of such cells can increase the efficacy of the treatment, for example, by increasing exposure to the cells such as by promoting expansion and/or persistence, they may also result in an even greater risk of developing a toxicity or a more severe toxicity. The provided methods provide embodiments to mitigate risks of toxicity, and thereby improving efficacy of the therapy.

In some embodiments, the provided embodiments are designed to or include features that result in a lower degree of risk of toxicity, a toxic outcome or symptom, toxicity-promoting profile, factor or property, such as a symptom or outcome associated with or indicative of cytokine release syndrome (CRS) or neurotoxicity. In some aspects, the lower degree of such risks is compared to other methods in which the subject and/or a biological sample from the subject has not been assessed for a factor indicative of tumor burden as described and/or in which the therapy has not been administered to a subject in accord with an assessment of any preexisting risk of the subject to toxicity following administration of the therapeutic cell composition, such as based on based on such factors indicative of tumor burden.

A. Toxicity

In some aspects, the toxic outcome of a therapy, such as a cell therapy, is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS, such as severe CRS, typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

CRS criteria that appear to correlate with the onset of CRS to predict which patients are more likely to be at risk for developing sCRS have been developed (see Davila et al. Science translational medicine. 2014;6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 1B below.

TABLE 1B

Exemplary Grading Criteria for CRS

| Grade | Description of Symptoms |
| --- | --- |
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention:<br>Oxygen requirement <40%, or<br>Hypotension responsive to fluids or low dose of a single vasopressor, or<br>Grade 2 organ toxicity (by CTCAE v4.0) |
| 3<br>Severe | Require and respond to aggressive intervention:<br>Oxygen requirement ≥40%, or<br>Hypotension requiring high dose of a single vasopressor (e.g., norepinephrine ≥20 µg/kg/min, dopamine ≥10 µg/kg/min, phenylephrine ≥200 µg/kg/min, or epinephrine ≥10 µg/kg/min), or<br>Hypotension requiring multiple vasopressors (e.g., vasopressin + one of the above agents, or combination vasopressors equivalent to ≥20 µg/kg/min norepinephrine), or<br>Grade 3 organ toxicity or Grade 4 transaminitis (by CTCAE v4.0) |
| 4<br>Life-threatening | Life-threatening:<br>Requirement for ventilator support, or<br>Grade 4 organ toxicity (excluding transaminitis) |
| 5<br>Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater, such as set forth in Table 1B.

In some embodiments, outcomes associated with severe CRS or grade 3 CRS or greater, such as grade 4 or greater, such as set forth in Table 1B. In some embodiments, these include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures). In some embodiments, severe CRS includes CRS that requires management or care in the intensive care unit (ICU).

In some embodiments, severe CRS encompasses a combination of (1) persistent fever (fever of at least 38 degrees Celsius for at least three days) and (2) a serum level of CRP of at least at or about 20 mg/dL. In some embodiments, severe CRS encompasses hypotension requiring the use of two or more vasopressors or respiratory failure requiring mechanical ventilation. In some embodiments, the dosage of vasopressors is increased in a second or subsequent administration.

In some embodiments, the toxicity is evident by the presence of a fever in the subject following administration of a therapy, such as cell therapy (e.g. CAR-T cells). In some embodiments, the fever in the subject is characterized as a body temperature of the subject that is (or is measured at) at or above a certain threshold temperature or level. In some aspects, the threshold temperature is that associated with at least a low-grade fever, with at least a moderate fever, and/or with at least a high-grade fever. In some embodiments, the threshold temperature is a particular temperature or range. For example, the threshold temperature may be at or about 38, 39, 40, 41, or 42 degrees Celsius, and/or may be a range of at or about 38 degrees Celsius to at or about 39 degrees Celsius, a range of at or about 39 degrees Celsius to at or about 40 degrees Celsius, a range of at or about 40 degrees Celsius to at or about 41 degrees, or a range of at or about 41 degrees Celsius to at or about 42 degrees Celsius.

In some embodiments, the toxicity is associated with a sustained fever, following administration of the therapy, such as cell therapy, e.g. CAR-T cell therapy. In some embodiments, the subject has, and/or is determined to or considered to have, a sustained fever if he or she exhibits a fever at or above the relevant threshold temperature, and where the fever or body temperature of the subject does not fluctuate by about, or by more than about, 1° C., and generally does not fluctuate by about, or by more than about, 0.5° C., 0.4° C., 0.3° C., or 0.2° C. Such absence of fluctuation above or at a certain amount generally is measured over a given period of time (such as over a 24-hour, 12-hour, 8-hour, 6-hour, 3-hour, or 1-hour period of time, which may be measured from the first sign of fever or the first temperature above the indicated threshold). For example, in some embodiments, a subject is considered to or is determined to exhibit sustained fever if he or she exhibits a fever of at least at or about 38 or 39 degrees Celsius, which does not fluctuate in temperature by more than at or about 0.5° C., 0.4° C., 0.3° C., or 0.2° C., over a period of 6 hours, over a period of 8 hours, or over a period of 12 hours, or over a period of 24 hours.

In some embodiments, the subject has, and/or is determined to or considered to have, a sustained fever if he or she exhibits a fever at or above the relevant threshold temperature, and where the fever or body temperature of the subject is not reduced, or is not reduced by or by more than a specified amount (e.g., by more than 1° C., and generally does not fluctuate by about, or by more than about, 0.5° C., 0.4° C., 0.3° C., or 0.2° C.), following a specified treatment, such as a treatment designed to reduce fever such as an antipyretic. An antipyretic may include any agent, e.g., compound, composition, or ingredient, that reduces fever, such as one of any number of agents known to have antipyretic effects, such as NSAIDs (such as ibuprofen, naproxen, ketoprofen, and nimesulide), salicylates, such as aspirin, choline salicylate, magnesium salicylate, and sodium salicylate, paracetamol, acetaminophen, Metamizole, Nabumetone, Phenaxone, antipyrine, febrifuges. In some embodiments, the antipyretic is acetaminophen. In some embodiments, it is or comprises ibuprophen or aspirin. For example, a subject is considered to have a sustained fever if he or she exhibits or is determined to exhibit a fever of at least at or about 38 or 39 degrees Celsius, which is not reduced by or is not reduced by more than at or about 0.5° C., 0.4° C., 0.3° C., or 0.2° C., or by at or about 1%, 2%, 3%, 4%, or 5%, over a period of 6 hours, over a period of 8 hours, or over a period of 12 hours, or over a period of 24 hours, even following treatment with the antipyretic such as tylenol. In some embodiments, the dosage of the antipyretic is a dosage ordinarily effective in such as subject to reduce fever or fever of a particular type such as fever associated with a bacterial or viral infection, e.g., a localized or systemic infection.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

In some aspects, the toxic outcome of a therapy, such as a cell therapy, is or is associated with or indicative of neurotoxicity or severe neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute-Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to, or secondary to, administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 2. In some embodiments, a severe neurotoxicity is deemed to be a prolonged grade 3 if symptoms or grade 3 neurotoxicity last for 10 days or longer.

TABLE 2

Exemplary Grading Criteria for neurotoxicity

| Grade | Description of Symptoms |
|---|---|
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the provided embodiments, including methods of treatment, lead to reduced symptoms associated with neurotoxicity following cell therapy compared to other methods. For example, subjects treated according to the provided methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the provided methods may have reduced symptoms associated with peripheral motor neuropathy, peripheral sensory neuropathy, dysesthesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

A. Agents for Ameliorating or Treating Toxicity

In some embodiments, the provided methods and articles of manufacture can be used in connection with, or involve or include, one or more agents or treatments for treating, preventing, delaying, or attenuating the development of a toxicity. In some examples, the agent or other treatment capable of treating, preventing, delaying, or attenuating the development of a toxicity is administered prior to and/or concurrently with administration of a therapeutic cell composition comprising the genetically engineered cells.

In some embodiments, the agent, e.g., a toxicity-targeting agent, or treatment capable of treating, preventing, delaying, or attenuating the development of a toxicity is a steroid, is an antagonist or inhibitor of a cytokine receptor, such as IL-6 receptor, CD122 receptor (IL-2Rbeta receptor), or CCR2, or is an inhibitor of a cytokine, such as IL-6, MCP-1, IL-10, IFN-γ, IL-8, or IL-18. In some embodiments, the agent is an agonist of a cytokine receptor and/or cytokine, such as TGF-β. In some embodiments, the agent, e.g., agonist, antagonist or inhibitor, is an antibody or antigen-binding fragment, a small molecule, a protein or peptide, or a nucleic acid.

In some embodiments, a fluid bolus can be employed as an intervention, such as to treat hypotension associated with CRS. In some embodiments, the target hematocrit levels are >24%. In some embodiments, the intervention includes the use of absorbent resin technology with blood or plasma filtration. In some cases, the intervention includes dialysis, plasmapheresis, or similar technologies. In some embodiments, vassopressors or acetaminophen can be employed.

In some embodiments, the agent can be administered sequentially, intermittently, or at the same time as or in the same composition as the therapy, such as cells for adoptive cell therapy. For example, the agent can be administered before, during, simultaneously with, or after administration of the immunotherapy and/or cell therapy.

In some embodiments, the agent is administered at a time as described herein and in accord with the provided methods, and/or with the provided articles of manufacture or compositions. In some embodiments, the toxicity-targeting agent is administered at a time that is within, such as less than or no more than, 3, 4, 5, 6, 7, 8, 9 or 10 days after initiation of the immunotherapy and/or cell therapy. In some embodiments, the toxicity-targeting agent is administered within or within about 1 day, 2 days or 3 days after initiation of administration of the immunotherapy and/or cell therapy.

In some embodiments, the agent, e.g., toxicity-targeting agent, is administered to a subject after initiation of administration of the immunotherapy and/or cell therapy at a time at which the subject does not exhibit grade 2 or higher CRS or grade 2 or higher neurotoxicity. In some aspects, the toxicity-targeting agent is administered after initiation of administration of the immunotherapy and/or cell therapy at a time at which the subject does not exhibit severe CRS or severe neurotoxicity. Thus, between initiation of administration of the immunotherapy and/or cell therapy and the toxicity-targeting agent, the subject is one that does not exhibit grade 2 or higher CRS, such as severe CRS, and/or does not exhibit grade 2 or higher neurotoxicity, such as severe neurotoxicity.

Non-limiting examples of interventions for treating or ameliorating a toxicity, such as severe CRS (sCRS), are described in Table 3. In some embodiments, the intervention includes tocilizumab or other toxicity-targeting agent as described, which can be at a time in which there is a sustained or persistent fever of greater than or about 38° C. or greater than or greater than about 39° C. in the subject. In some embodiments, the fever is sustained in the subject for more than 10 hours, more than 12 hours, more than 16 hours, or more than 24 hours before intervention.

TABLE 3

| Symptoms related to CRS | Suggested Intervention |
| --- | --- |
| Fever of ≥38.3° C. | Acetaminophen (12.5 mg/kg) PO/IV up to every four hours |
| Persistent fever of ≥39° C. for 10 hours that is unresponsive to acetaminophen | Tocilizumab (8-12 mg/kg) IV |
| Persistent fever of ≥39° C. after tocilizumab | Dexamethasone 5-10 mg IV/PO up to every 6-12 hours with continued fevers |
| Recurrence of symptoms 48 hours after initial dose of tocilizumab | Tocilizumab (8-12 mg/kg) IV |
| Hypotension | Fluid bolus, target hematocrit >24% |
| Persistent/recurrent hypotension after initial fluid bolus (within 6 hours) | Tocilizumab (8-12 mg/kg) IV |
| Use of low dose pressors for hypotension for longer than 12 hours | Dexamethasone 5-10 mg IV/PO up to every 6 hours with continued use of pressors |
| Initiation of higher dose pressors or addition of a second pressor for hypotension | Dexamethasone 5-10 mg IV/PO up to every 6 hours with continued use of pressors |
| Initiation of oxygen supplementation | Tocilizumab (8-12 mg/kg) IV |
| Increasing respiratory support with concern for impending intubation | Dexamethasone 5-10 mg IV/PO up to every 6 hours with continued use of pressors |
| Recurrence/Persistence of symptoms for which tocilizumab was given ≥48 hours after initial dose was administered | Tocilizumab (8-12 mg/kg) IV |

In some cases, the agent or therapy or intervention, e.g., toxicity-targeting agent, is administered alone or is administered as part of a composition or formulation, such as a pharmaceutical composition or formulation, as described herein. Thus, the agent alone or as part of a pharmaceutical composition can be administered intravenously or orally, or by any other acceptable known route of administration or as described herein.

In some embodiments, the dosage of agent or the frequency of administration of the agent in a dosage regimen is reduced compared to the dosage of the agent or its frequency in a method in which a subject is treated with the agent after grade 2 or higher CRS or neurotoxicity, such as after severe, e.g., grade 3 or higher, CRS or after severe, e.g., grade 3 or higher neurotoxicity, has developed or been diagnosed (e.g. after physical signs or symptoms of grade 3 or higher CRS or neurotoxicity has manifested). In some embodiments, the dosage of agent or the frequency of administration of the agent in a dosage regimen is reduced compared to the dosage of the agent or its frequency in a method in which a subject is treated for CRS or neurotoxicity greater than 3 days, 4 days, 5 days, 6 days, 1 week, 2 weeks, three weeks, or more after administration of the immunotherapy and/or cell therapy. In some embodiments, the dosage is reduced by greater than or greater than about 1.2-fold, 1.5-fold, 2-fold, 3-fold, 4-fold, 5-fold, 6-fold, 7-fold, 8-fold, 9-fold, 10-fold or more. In some embodiments, the dosage is reduced by greater than or about 10%, 20%, 30%, 40%, 50%, 60%, 70%, 80%, 90%, or more. In some embodiments, the frequency of dosing is reduced, such as the number of daily doses is reduced or the number of days of dosing is reduced.

1. Steroid

In some embodiments, the agent, e.g., toxicity-targeting agent, that treats and/or that prevents, delays, or attenuates the development of or risk for developing a toxicity to an immunotherapy and/or a cell therapy, is a steroid, e.g., corticosteroid. Corticosteroids typically include glucocorticoids and mineralocorticoids.

Any corticosteroid, e.g., glucocorticoid, can be used in the methods provided herein. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemisuccinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980).

In some examples, the glucocorticoid is selected from among cortisones, dexamethasones, hydrocortisones, methylprednisolones, prednisolones and prednisones. In a particular example, the glucocorticoid is dexamethasone.

In some embodiments, the agent is a corticosteroid and is administered in an amount that is therapeutically effective to treat, ameliorate or reduce one or more symptoms of a toxicity to an immunotherapy and/or a cell therapy, such as CRS or neurotoxicity. In some embodiments, indicators of improvement or successful treatment include determination of the failure to manifest a relevant score on toxicity grading scale (e.g. CRS or neurotoxicity grading scale), such as a score of less than 3, or a change in grading or severity on the grading scale as discussed herein, such as a change from a score of 4 to a score of 3, or a change from a score of 4 to a score of 2, 1 or 0.

In some aspects, the corticosteroid is provided in a therapeutically effective dose. Therapeutically effective concentration can be determined empirically by testing in known in vitro or in vivo (e.g. animal model) systems. For example, the amount of a selected corticosteroid to be administered to ameliorate symptoms or adverse effects of a toxicity to an immunotherapy and/or a cell therapy, such as CRS or neurotoxicity, can be determined by standard clinical techniques. In addition, animal models can be employed to help identify optimal dosage ranges. The precise dosage, which can be determined empirically, can depend on the particular therapeutic preparation, the regime and dosing schedule, the route of administration and the seriousness of the disease.

The corticosteroid can be administered in any amount that is effective to ameliorate one or more symptoms associated with the toxicity, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid can be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

The corticosteroid, or glucocorticoid, for example dexamethasone, can be administered orally (tablets, liquid or liquid concentrate), PO, intravenously (IV), intramuscularly or by any other known route or route described herein (e.g., with respect to pharmaceutical formulations). In some aspects, the corticosteroid is administered as a bolus, and in other aspects it may be administered over a period of time.

In some aspects, the glucocorticoid can be administered over a period of more than one day, such as over two days, over 3 days, or over 4 or more days. In some embodiments, the corticosteroid can be administered one per day, twice per day, or three times or more per day. For example, the corticosteroid, e.g., dexamethasone, may in some examples be administered at 10 mg (or equivalent) IV twice a day for three days.

In some embodiments, the dosage of corticosteroid, e.g., glucocorticoid, is administered in successively lower dosages per treatment. Hence, in some such treatment regimes, the dose of corticosteroid is tapered. For example, the corticosteroid may be administered at an initial dose (or equivalent dose, such as with reference to dexamethasone) of 4 mg, and upon each successive administration the dose may be lowered, such that the dose is 3 mg for the next administration, 2 mg for the next administration, and 1 mg for the next administration Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Table 4 shows equivalence in terms of potency for various glucocorticoids and routes of administration. Equivalent potency in clinical dosing is well known. Information relating to equivalent steroid dosing (in a non-chronotherapeutic manner) may be found in the British National Formulary (BNF) 37, March 1999.

TABLE 4

Glucocorticoid administration

| Glucocorticoid (Route) | Equivalency Potency |
|---|---|
| Hydrocortisone (IV or PO) | 20 |
| Prednisone | 5 |
| Prednisolone (IV or PO) | 5 |
| Methylprednisolone sodium succinate (IV) | 4 |
| Dexamethasone (IV or PO) | 0.5-0.75 |

Thus, in some embodiments, the steroid is administered in an equivalent dosage amount of from or from about 1.0 mg to 20 mg dexamethasone per day, such as 1.0 mg to 15 mg dexamethasone per day, 1.0 mg to 10 mg dexamethasone per day, 2.0 mg to 8 mg dexamethasone per day, or 2.0 mg to 6.0 mg dexamethasone per day, each inclusive. In some cases, the steroid is administered in an equivalent dose of at or about 4 mg or at or about 8 mg dexamethasone per day.

In some embodiments, the steroid is administered if fever persists after treatment with tocilizumab. For example, in some embodiments, dexamethasone is administered orally or intravenously at a dosage of 5-10 mg up to every 6-12 hours with continued fevers. In some embodiments, tocilizumab is administered concurrently with or subsequent to oxygen supplementation.

2. Microglial Cell Inhibitor

In some embodiments, the inhibitor in the combination therapy is an inhibitor of a microglial cell activity. In some embodiments, the administration of the inhibitor modulates the activity of microglia. In some embodiments, the inhibitor is an antagonist that inhibits the activity of a signaling pathway in microglia. In some embodiments, the microglia inhibitor affects microglial homeostasis, survival, and/or proliferation. In some embodiments, the inhibitor targets the CSF1R signaling pathway. In some embodiments, the inhibitor is an inhibitor of CSF1R. In some embodiments, the inhibitor is a small molecule. In some cases, the inhibitor is an antibody.

In some aspects, administration of the inhibitor results in one or more effects selected from an alteration in microglial homeostasis and viability, a decrease or blockade of microglial cell proliferation, a reduction or elimination of microglial cells, a reduction in microglial activation, a reduction in nitric oxide production from microglia, a reduction in nitric oxide synthase activity in microglia, or protection of motor neurons affected by microglial activation. In some embodiments, the agent alters the level of a serum or blood biomarker of CSF1R inhibition, or a decrease in the level of urinary collagen type 1 cross-linked N-telopeptide (NTX) compared to at a time just prior to initiation of the administration of the inhibitor. In some embodiments, the administration of the agent transiently inhibits the activity of microglia activity and/or wherein the inhibition of microglia activity is not permanent. In some embodiments, the administration of the agent transiently inhibits the activity of CSF1R and/or wherein the inhibition of CSF1R activity is not permanent.

In some embodiments, the agent that reduces microglial cell activity is a small molecule, peptide, protein, antibody or antigen-binding fragment thereof, an antibody mimetic, an aptamer, or a nucleic acid molecule. In some embodiments, the method involves administration of an inhibitor of microglia activity. In some embodiments, the agent is an antagonist that inhibits the activity of a signaling pathway in microglia. In some embodiments, the agent that reduces microglial cell activity affects microglial homeostasis, survival, and/or proliferation.

In some embodiments, the agent that reduces microglial cell activation is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155), upregulates microRNA-124 (miR-124), inhibits nitric oxide production in microglia, inhibits nitric oxide synthase, or activates the transcription factor NRF2 (also called nuclear factor (erythroid-derived 2)-like 2, or NFE2L2).

In some embodiments, the agent that reduces microglial cell activity targets CSF1 (also called macrophage colony-stimulating factor MCSF). In some embodiments, the agent that reduces microglial cell activity affects MCSF-stimulated phosphorylation of the M-CSF receptor (Pryer et al. Proc Am Assoc Cancer Res, AACR Abstract nr DDT02-2 (2009)). In some cases, the agent that reduces microglial cell activity is MCS110 (international patent application publication number WO2014001802; Clinical Trial Study Record Nos.: A1 NCT00757757; NCT02807844; NCT02435680; NCTO1643850).

In some embodiments, the agent that reduces microglial cell activity is a small molecule that targets the CSF1 pathway. In some embodiments, the agent is a small molecule that binds CSF1R. In some embodiments, the agent is a small molecule which inhibits CSF1R kinase activity by competing with ATP binding to CSF1R kinase. In some embodiments, the agent is a small molecule which inhibits the activation of the CFS1R receptor. In some cases, the binding of the CSF-1 ligand to the CSF1R is inhibited. In some embodiments, the agent that reduces microglial cell activity is any of the inhibitors described in US Patent Application Publication Number US20160032248.

In some embodiments, the agent is a small molecule inhibitor selected from PLX-3397, PLX7486, JNJ-40346527, JNJ28312141, ARRY-382, PLX73086 (AC-708), DCC-3014, AZD6495, GW2580, Ki20227, BLZ945, PLX647, PLX5622. In some embodiments, the agent is any of the inhibitors described in Conway et al., Proc Natl Acad Sci USA, 102(44):16078-83 (2005); Dagher et al., Journal of Neuroinflammation, 12:139 (2015); Ohno et al., Mol Cancer Ther. 5(11):2634-43 (2006); von Tresckow et al., Clin Cancer Res., 21(8) (2015); Manthey et al. Mol Cancer Ther. (8(11):3151-61 (2009); Pyonteck et al., Nat Med. 19(10): 1264-1272 (2013); Haegel et al., Cancer Res AACR Abstract nr 288 (2015); Smith et al., Cancer Res AACR Abstract nr 4889 (2016); Clinical Trial Study Record Nos.: NCT01525602; NCT02734433; NCT02777710; NCT01804530; NCT01597739; NCT01572519; NCT01054014; NCT01316822; NCT02880371; NCT02673736; international patent application publication numbers WO2008063888A2, WO2006009755A2, US patent application publication numbers US20110044998, US 2014/0065141, and US 2015/0119267.

In some embodiments, the agent that reduces microglial cell activity is 4-((2-(((1R,2R)-2-hydroxycyclohexyl)amino)benzo[d]thiazol-6-yl)oxy)-N-methylpicolinamide (BLZ945) or a pharmaceutically acceptable salt thereof or derivatives thereof. In some embodiments, the agent is the following compound:

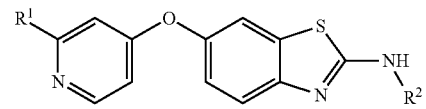

wherein R1 is an alkyl pyrazole or an alkyl carboxamide, and R2 is a hydroxycycloalkyl or a pharmaceutically acceptable salt thereof.

In some embodiments, the agent that reduces microglial cell activity is 5-((5-chloro-1H-pyrrolo[2,3-b]pyridin-3-yl)methyl)-N-((6-(trifluoromethyl)pyridin-3-yl)methyl)pyridin-2-amine, N-[5-[(5-Chloro-1H-pyrrolo[2,3-b]pyridin-3-yl)methyl]-2-pyridinyl]-6-(trifluoromethyl)-3-pyridinemethanamine) (PLX 3397) or a pharmaceutically acceptable salt thereof or derivatives thereof. In some embodiments, the agent is 5-(1H-Pyrrolo[2,3-b]pyridin-3-ylmethyl)-N-[[4-(trifluoromethyl)phenyl]methyl]-2-pyridinamine dihydrochloride (PLX647) or a pharmaceutically acceptable salt thereof or derivatives thereof. In some embodiments, the agent that reduces microglial cell activity is the following compound:

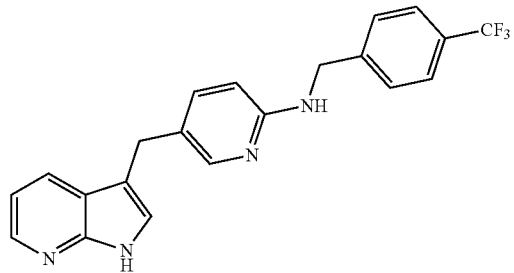 [SMILES: FC(F)(F)c1ccc(CNc2ccc(Cc3c[nH]c4ncccc34)cn2)cc1]

or a pharmaceutically acceptable salt thereof. In some embodiments, the agent that reduces microglial cell activity is the following compound:

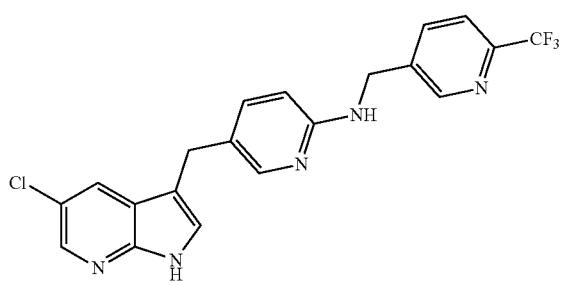 [SMILES: FC(F)(F)c1ccc(CNc2ccc(Cc3c[nH]c4ncc(Cl)cc34)cn2)cn1]

or a pharmaceutically acceptable salt thereof. In some embodiments, the agent is any of the inhibitors described in U.S. Pat. No. 7,893,075.

In some embodiments, the agent that reduces microglial cell activity is 4-cyano-N-[2-(1-cyclohexen-1-yl)-4-[1-[(dimethylamino)acetyl]-4-piperidinyl]phenyl]-1H-imidazole-2-carboxamide monohydrochloride (JNJ28312141) or a pharmaceutically acceptable salt thereof or derivatives thereof. In some embodiments, the agent is the following compound:

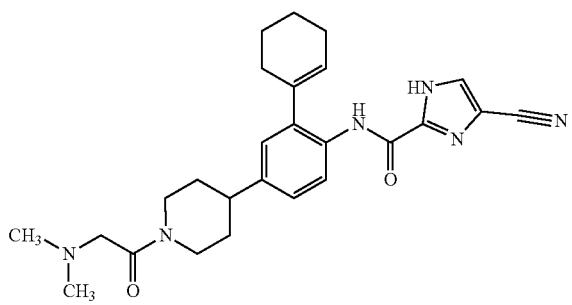 [SMILES: CN(C)CC(=O)N1CCC(c2ccc(NC(=O)c3nc(C#N)c[nH]3)c(C3=CCCCC3)c2)CC1]

or a pharmaceutically acceptable salt thereof. In some embodiments, the agent is any of the inhibitors described in U.S. Pat. No. 7,645,755.

In some embodiments, the agent that reduces microglial cell activity is 1H-Imidazole-2-carboxamide, 5-cyano-N-(2-(4,4-dimethyl-1-cyclohexen-1-yl)-6-(tetrahydro-2,2,6,6-tetramethyl-2H-pyran-4-yl)-3-pyridinyl)-, 4-Cyano-1H-imidazole-2-carboxylic acid N-(2-(4,4-dimethylcyclohex-1-enyl)-6-(2,2,6,6-tetramethyltetrahydropyran-4-yl)pyridin-3-yl)amide, 4-Cyano-N-(2-(4,4-dimethylcyclohex-1-en-1-yl)-6-(2,2,6,6-tetramethyl-tetrahydro-2H-pyran-4-yl)pyridin-3-yl)-1H-imidazole-2-carboxamide (JNJ-40346527) or a pharmaceutically acceptable salt thereof or derivatives thereof. In some embodiments, the agent is the following compound:

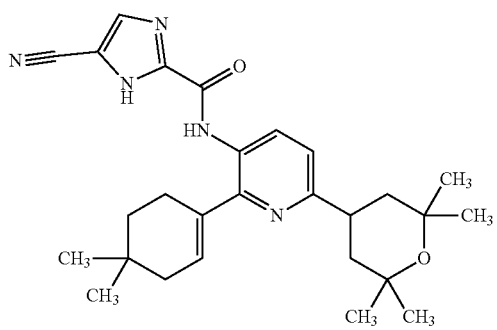 [SMILES: CC1(C)CC=C(c2nc(C3CC(C)(C)OC(C)(C)C3)ccc2NC(=O)c2ncc(C#N)[nH]2)CC1]

or a pharmaceutically acceptable salt thereof.

In another embodiment, the agent that reduces microglial cell activity is 5-(3-Methoxy-4-((4-methoxybenzyl)oxy)benzyl)pyrimidine-2,4-diamine (GW2580) or a pharmaceutically acceptable salt thereof or derivatives thereof. In some embodiments, the agent is the following compound:

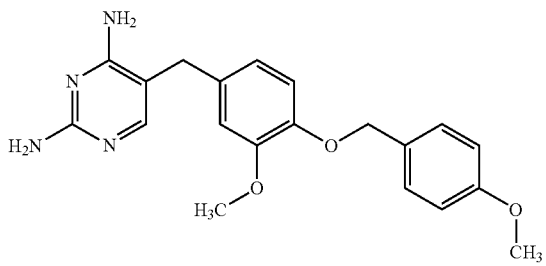 [SMILES: COc1ccc(COc2ccc(Cc3cnc(N)nc3N)cc2OC)cc1]

or a pharmaceutically acceptable salt thereof (international patent application publication number WO2009099553).

In some embodiments, the agent that reduces microglial cell activity is 4-(2,4-difluoroanilino)-7-ethoxy-6-(4-methylpiperazin-1-yl)quinoline-3-carboxamide (AZD6495) or a pharmaceutically acceptable salt thereof or derivatives thereof. In some embodiments, the agent is the following compound:

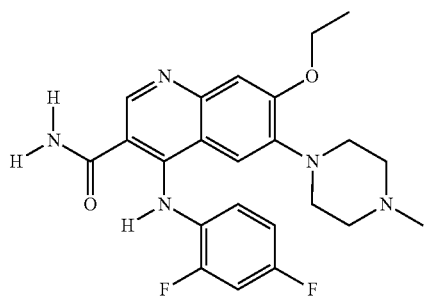 [SMILES: CCOc1cc2ncc(C(N)=O)c(Nc3ccc(F)cc3F)c2cc1N1CCN(C)CC1]

or a pharmaceutically acceptable salt thereof.

In some embodiments, the agent that reduces microglial cell activity is N-{4-[(6,7-dimethoxy-4-quinolyl)oxy]-2-methoxyphenyl}-NO-[1-(1,3-thiazole-2-yl)ethyl]urea (Ki20227) or a pharmaceutically acceptable salt thereof or derivatives thereof. In some embodiments, the agent is the following compound:

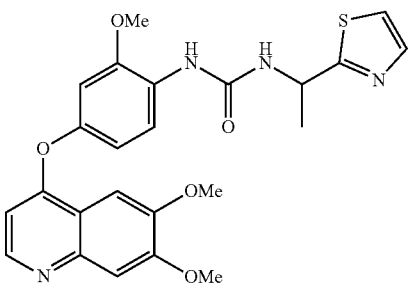 [SMILES: COc1cc(Oc2ccnc3cc(OC)c(OC)cc23)ccc1NC(=O)NC(C)c1nccs1]

or a pharmaceutically acceptable salt thereof.

In some embodiments, the agent that reduces microglial cell activation is an antibody that targets the CSF1 pathway. In some embodiments, the agent is an antibody that binds CSF1R. In some embodiments, the anti-CSF1R antibody blocks CSF1R dimerization. In some embodiments, the anti-CSF1R antibody blocks the CSF1R dimerization interface that is formed by domains D4 and D5 (Ries et al. Cancer Cell 25(6):846-59 (2014)). In some cases, the agent is selected from emactuzumab (RG7155; R05509554), Cabiralizumab (FPA-008), LY-3022855 (IMC-CS4), AMG-820, TG-3003, MCS110, H27K15, 12-2D6, 2-4A5 (Rovida and Sbarba, J Clin Cell Immunol. 6:6 (2015); Clinical Trial Study Record Nos.: NCT02760797; NCT01494688; NCT02323191; NCT01962337; NCT02471716; NCT02526017; NCTO1346358; NCT02265536; NCTO1444404; NCT02713529, NCT00757757; NCT02807844; NCT02435680; NCTO1643850).

In some embodiments, the agent that reduces microglial cell activation is a tetracycline antibiotic. For example, the agent affects IL-1b, IL-6, TNF-α, or iNOS concentration in microglia cells (Yrjanheikki et al. PNAS 95(26): 15769-15774 (1998); Clinical Trial Study Record No: NCT01120899). In some embodiments, the agent is an opioid antagonist (Younger et al. Pain Med. 10(4):663-672 (2009.) In some embodiments, the agent reduces glutamatergic neurotransmission (U.S. Pat. No. 5,527,814). In some embodiments, the agent modulates NFkB signaling (Valera et al J. Neuroinflammation 12:93 (2015); Clinical Trial Study Record No: NCT00231140). In some embodiments, the agent targets cannabinoid receptors (Ramirez et al. J. Neurosci 25(8):1904-13(2005)). In some embodiments, the agent is selected from minocycline, naloxone, riluzole, lenalidomide, and a cannabinoid (optionally WIN55 or 212-2).

Nitric oxide production from microglia is believed, in some cases, to result in or increase neurotoxicity. In some embodiments, the agent modulates or inhibits nitric oxide production from microglia. In some embodiments, the agent inhibits nitric oxide synthase (NOS). In some embodiments, the NOS inhibitor is Ronopterin (VAS-203), also known as 4-amino-tetrahydrobiopterin (4-ABH4). In some embodiments, the NOS inhibitor is cindunistat, A-84643, ONO-1714, L-NOARG, NCX-456, VAS-2381, GW-273629, NXN-462, CKD-712, KD-7040, or guanidinoethyldisulfide. In some embodiments, the agent is any of the inhibitors described in Höing et al., Cell Stem Cell. 2012 Nov. 2; 11(5):620-32.

In some embodiments, the agent blocks T cell trafficking, such as to the central nervous system. In some embodiments, blocking T cell trafficking can reduce or prevent immune cells from crossing blood vessel walls into the central nervous system, including crossing the blood-brain barrier. In some cases, activated antigen-specific T cells produce proinflammatory cytokines, including IFN-γ and TNF, upon reactivation in the CNS, leading to activation of resident cells such as microglia and astrocytes. See Kivisäkk et al., Neurology. 2009 Jun. 2; 72(22): 1922-1930. Thus, in some embodiments, sequestering activated T cells from microglial cells, such as by blocking trafficking and/or inhibiting the ability of such cells to cross the blood-brain barrier, can reduce or eliminate microglial activation. In some embodiments, the agent inhibits adhesion molecules on immune cells, including T cells. In some embodiments, the agent inhibits an integrin. In some embodiments, the integrin is alpha-4 integrin. In some embodiments, the agent is natalizumab (Tysabri®). In some embodiments, the agent modulates a cell surface receptor. In some embodiments, the agent modulates the sphingosine-1-phosphate (S1P) receptor, such as S1PR1 or S1PR5. In some embodiments, the agent causes the internalization of a cellular receptor, such as a sphingosine-1-phosphate (SIP) receptor, such as S1PR1 or S1PR5. In some embodiments, the agent is fingolimod (Gilenya®) or ozanimod (RPC-1063).

The transcription factor NRF2 is believed to regulate the anti-oxidant response, for example, by turning on genes that contain a cis-acting element in their promoter region. An example of such an element includes an antioxidant response element (ARE). In some embodiments, the agent activates NRF2. In some embodiments, activating NRF2 in microglial cells reduces the microglial cells' responsiveness to IFN and LPS. In some embodiments, activating NRF2 inhibits, slows, or reduces demyelination, axonal loss, neuronal death, and/or oligodendrocyte death. In some embodiments, the agent upregulates the cellular cytoprotective pathway regulated by NRF2. In some embodiments, the agent that activates NRF2 is dimethyl fumarate (Tecfidera®). In some embodiments, the agent is any of the inhibitors described in U.S. Pat. No. 8,399,514. In some embodiments, the agent is any of the inhibitors described in Höing et al., Cell Stem Cell. 2012 Nov. 2; 11(5):620-32.

In some embodiments, the agent that reduces microglial cell activation is (4S,4aS,5aR,12aS)-4,7-bis(dimethylamino)-3,10,12,12a-tetrahydroxy-1,11-dioxo-1,4,4a,5,5a,6,11,12a-octahydrotetracene-2-carboxamide (Minocycline) or a pharmaceutically acceptable salt thereof or derivatives thereof. In some embodiments, the agent is any of the compounds described in US patent application publication number US20100190755. In some embodiments, the agent is the following compound:

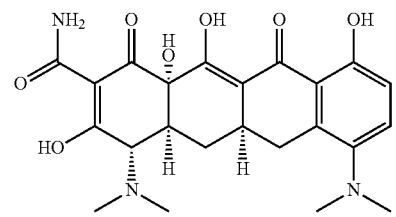 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

In some embodiments, the agent that reduces microglial cell activation is 3-(7-amino-3-oxo-1H-isoindol-2-yl)piperidine-2,6-dione (lenalidomide) or a pharmaceutically acceptable salt thereof or derivatives thereof. In some embodiments, the agent is the following compound:

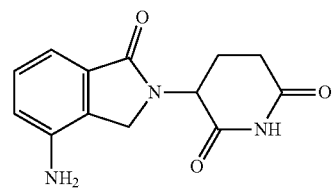 [SMILES: Nc1cccc2c1CN(C1CCC(=O)NC1=O)C2=O]

or a pharmaceutically acceptable salt thereof.

In some embodiments, the agent that reduces microglial cell activation is 4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one (naloxone) or a pharmaceutically acceptable salt thereof or derivatives thereof. In some embodiments, the agent is any of the compounds described in U.S. Pat. No. 8,247,425. In some embodiments, the agent is the following compound:

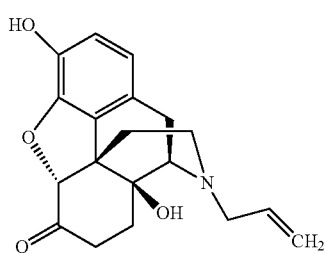 [SMILES: C=CCN1CC[C@]23c4c5ccc(O)c4O[C@H]2C(=O)CC[C@@]3(O)[C@H]1C5]

or a pharmaceutically acceptable salt thereof.

In some embodiments, the agent that reduces microglial cell activation is 2-amino-6-(trifluoromethoxy)benzothiazole, 6-(trifluoromethoxy)benzo[d]thiazol-2-amine, or 6-(trifluoromethoxy)-1,3-benzothiazol-2-amine (riluzole) or a pharmaceutically acceptable salt thereof or derivatives thereof as described in U.S. Pat. No. 5,527,814. In some embodiments, the agent is the following compound:

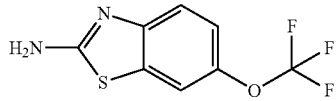

or a pharmaceutically acceptable salt thereof.

In some embodiments, the agent that reduces microglial cell activation is a modulator of a signaling pathway in microglia. In some cases, the agent reduces microglia singling. In some embodiments, the agent is a GM-CSF (CSF2) inhibitor. In other embodiments, the agent that reduces microglial cell activation is an ion channel blocker. In some specific embodiments, the agent is a calcium channel blocker. For example, in some specific examples, the agent is a dihydropyridine calcium channel blocker. In some embodiments, the agent is a microRNA inhibitor. For example, the agent targets miR-155. In some embodiments, the agent that reduces microglial cell activation is selected from MOR103, Nimodipine, IVIg, and LNA-anti-miR-155 (Butoxsky et al. *Ann Neurol.*, 77(1):75-99 (2015) and Sanz et al., *Br J Pharmacol.* 167(8): 1702-1711 (2012); Winter et al., *Ann Clin and Transl Neurol.* 2328-9503 (2016); Clinical Trial Study Record Nos.: NCT01517282, NCT00750867).

In some embodiments, the agent that reduces microglial cell activation is 3-(2-methoxyethyl) 5-propan-2-yl 2,6-dimethyl-4-(3-nitrophenyl)-1,4-dihydropyridine-3,5-dicarboxylate (nimodipine) or a pharmaceutically acceptable salt thereof or derivatives thereof. In some embodiments, the agent is any of the inhibitors described in U.S. Pat. No. 3,799,934. In some embodiments, the agent is the following compound:

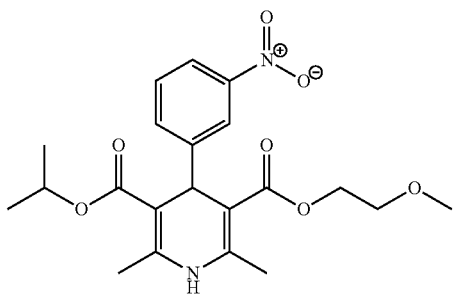 [SMILES: COCCOC(=O)C1=C(C)NC(C)=C(C(=O)OC(C)C)C1c1cccc([N+](=O)[O-])c1]

or a pharmaceutically acceptable salt thereof.

In some cases, the agent that reduces microglial cell activation is administered in a form that only affects to central nervous system and/or does not affect tumor-associated macrophages. In some embodiments, the agent promotes microglia quiescence but does not eliminate or reduce the number of microglia. In some embodiments, the method involves inhibiting microglia activity specifically in the brain such as described in Ponomarev et al., *Nature Medicine*, (1):64-70 (2011)

Exemplary agents that reduce microglial cell activation, and exemplary dosing regimens for administering such agents, are set forth in Table 5 below.

TABLE 5

Exemplary microglia inhibitors and dosage regimens

| Exemplary Inhibitor | Type of Molecule | Molecular Target(s) | Exemplary Dosing Regimen(s) |
|---|---|---|---|
| Pexidartinib (PLX3397) | small molecule | CSF1R; c-Kit; FLT3 | 200 mg tablets, twice daily for 28 days; Administer daily as split dose regimen, five dose-levels possible in dose escalation part: 400 mg 5 days on 2 days off (intermittent schedule), 400 mg, 600 mg, 800 mg or 1000 mg; 1000 mg/day for 2 weeks then 800 mg/day for 22 weeks |
| Emactuzumab (RG1755; RO5509554) | monoclonal antibody | CSF1R | 100-3000 mg once every 2 weeks |
| Cabiralizumab (FPA-008) | antibody | CSF1R | Intravenous infusion over 30 minutes every 2 weeks |
| LY-3022855 (IMC-CS4) | monoclonal antibody | CSF1R | 1.25 mg/kg intravenous delivery every 2 weeks for 6 weeks |
| JNJ-40346527 | small molecule | CSF1R | 100 mg twice daily for 12 weeks; 100-1000 mg capsule daily |
| MCS110 | antibody | MCSF (CSF1) | Up to 4 doses of 10 mg/kg MCS110 administered intravenously once every 4 weeks starting at Day 1 |
| MOR103 | antibody | GM-CSF | 6 doses of 0.5-2.0 mg/kg over 70 days |
| IVIg | immunoglobulin | Unknown | Intravenous infusion of 0.4 g/kg each month for 6 months |

TABLE 5-continued

Exemplary microglia inhibitors and dosage regimens

| Exemplary Inhibitor | Type of Molecule | Molecular Target(s) | Exemplary Dosing Regimen(s) |
|---|---|---|---|
| Minocyline | small molecule | broad spectrum antibiotic: IL-1b; IL-6, TNF-a; iNOS | Oral dose of 100 mg of minocycline twice daily for 24 months |
| Naloxone | small molecule | Opioid receptors | 4.5 mg naltrexone hydrochloride capsules once/day for 8 weeks |
| Lenalidomide/ thalidomide | small molecule | NFkB signaling | 100-400 mg daily |
| Riluzole | small molecule | Glutamate release by microglia | 50 mg twice daily |
| Cannabinoids/ cannabidiol (e.g. WIN55, 212-2) | small molecule | cannabinoid receptors | Orally 10 mg/kg/day for 6 weeks (average of 700 mg/day) |
| Dimethyl fumarate (Tecfidera ®). | small molecule | Nrf2 signaling | Starting dose of 120 mg taken orally twice/day for 7 days. Dose increased to 240 mg taken orally twice/day thereafter |
| natalizumab (Tysabri ®) | antibody | alpha-4 integrin | 300 mg infused intravenously over one hour, every four weeks |
| fingolimod (Gilenya ®) | small molecule | S1P receptors, including S1PR1 | 0.5 mg orally once-daily |
| ozanimod (RPC-1063) | small molecule | S1PR1 and S1PR5 | 0.25 mg, 0.5 mg, or 1 mg once daily |

3. Other Agents (e.g. Cytokine Targeting Agents)

In some embodiments, the agent, e.g. toxicity-targeting agent, that treats or ameliorates symptoms of a toxicity of immunotherapy and/or a cell therapy, such as CRS or neurotoxicity, is one that targets a cytokine, e.g., is an antagonist or inhibitor of a cytokine, such as transforming growth factor beta (TGF-beta), interleukin 6 (IL-6), interleukin 10 (IL-10), IL-2, MIP1β (CCL4), TNF alpha, IL-1, interferon gamma (IFN-gamma), or monocyte chemoattractant protein-1 (MCP-1). In some embodiments, the agent that treats or ameliorates symptoms of a toxicity of an immunotherapy and/or a cell therapy, such as CRS or neurotoxicity, is one that targets (e.g. inhibits or is an antagonist of) a cytokine receptor, such as IL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1β receptor (e.g., CCR5), TNF alpha receptor (e.g., TNFR1), IL-1 receptor (ILI-Rα/IL-1Rβ), or IL-10 receptor (IL-10β).

The amount of a selected agent that treats or ameliorates symptoms of a toxicity of an immunotherapy and/or a cell therapy, such as CRS or neurotoxicity to be administered to ameliorate symptoms or adverse effects of a toxicity to an immunotherapy and/or a cell therapy, such as CRS or neurotoxicity, can be determined by standard clinical techniques. Exemplary adverse events include, but are not limited to, an increase in alanine aminotransferase, an increase in aspartate aminotransferase, chills, febrile neutropenia, headache, hypotension, left ventricular dysfunction, encephalopathy, hydrocephalus, seizure, and/or tremor.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg.

In some embodiments, the agent is administered from or from about 0.5 mg/kg to 100 mg/kg, such as from or from about 1 mg/kg to 50 mg/kg, 1 mg/kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive. In some aspects, the agent is administered in a dosage amount of at least or at least about or about 1 mg/kg, 2 mg/kg, 4 mg/kg, 6 mg/kg, 8 mg/kg, 10 mg/kg or more. In some embodiments, the agent is administered at a dose of 4 mg/kg or 8 mg/kg.

In some embodiments, the agent is administered by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the amount of the agent is administered about or approximately twice daily, daily, every other day, three times a week, weekly, every other week or once a month.

In some embodiments, the agent is administered as part of a composition or formulation, such as a pharmaceutical composition or formulation as described below. Thus, in some cases, the composition comprising the agent is administered as described below. In other aspects, the agent is administered alone and may be administered by any known acceptable route of administration or by one described herein, such as with respect to compositions and pharmaceutical formulations.

In some embodiments, the agent that treats or ameliorates symptoms of a toxicity of the immunotherapy and/or cell therapy, such as CRS or neurotoxicity, is an antibody or antigen binding fragment. In some embodiments, the agent is tocilizumab, siltuximab, sarilumab, olokizumab (CDP6038), elsilimomab, ALD518/BMS-945429, sirukumab (CNTO 136), CPSI-2634, ARGX-109, FE301, or FM101.

In some embodiments, the agent is an antagonist or inhibitor of IL-6 or the IL-6 receptor (IL-6R). In some aspects, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-IL-6 antibody, such as siltuximab, elsilimomab, ALD518/BMS-945429, sirukumab (CNTO 136), CPSI-2634, ARGX-109, FE301, FM101, or olokizumab (CDP6038). In some aspects, the agent may neutralize IL-6 activity by inhibiting the ligand-receptor interactions. The feasibility of this general type of approach has been demonstrated with a natural occurring receptor antagonist for interleukin-1. See Harmurn, C. H. et al., Nature (1990) 343:336-340. In some aspects, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, the agent is tocilizumab. In some embodiments, tocilizumab is administered as an early intervention in accord with the provided methods, and/or with the provided articles of manufacture or compositions, at a dosage of from or from about 1 mg/kg to 12 mg/kg, such as at or about 4 mg/kg, 8 mg/kg, or 10 mg/kg. In some embodiments, tocilizumab is administered by intravenous infusion. In some embodiments, tocilizumab is administered for a persistent fever of greater than 39° C. lasting 10 hours that is unresponsive to acetaminophen. In some embodiments, a second administration of tocilizumab is provided if symptoms recur after 48 hours of the initial dose.

In some embodiments, the agent is an agonist or stimulator of TGF-β or a TGF-β receptor (e.g., TGF-β receptor I, II, or III). In some aspects, the agent is an antibody that increases TGF-β activity, such as an antibody or antigen-binding fragment that binds to TGF-β or one of its receptors. In some embodiments, the agent that is an agonist or stimulator of TGF-β and/or its receptor is a small molecule, a protein or peptide, or a nucleic acid.

In some embodiments, the agent is an antagonist or inhibitor of MCP-1 (CCL2) or a MCP-1 receptor (e.g., MCP-1 receptor CCR2 or CCR4). In some aspects, the agent is an antibody that neutralizes MCP-1 activity, such as an antibody or antigen-binding fragment that binds to MCP-1 or one of its receptors (CCR2 or CCR4). In some embodiments, the MCP-1 antagonist or inhibitor is any described in Gong et al. J Exp Med. 1997 Jul. 7; 186(1): 131-137 or Shahrara et al. J Immunol 2008; 180:3447-3456. In some embodiments, the agent that is an antagonist or inhibitor of MCP-1 and/or its receptor (CCR2 or CCR4) is a small molecule, a protein or peptide, or a nucleic acid.

In some embodiments, the agent is an antagonist or inhibitor of IFN-γ or an IFN-γ receptor (IFNGR). In some aspects, the agent is an antibody that neutralizes IFN-γ activity, such as an antibody or antigen-binding fragment that binds to IFN-γ or its receptor (IFNGR). In some aspects, the IFN-gamma neutralizing antibody is any described in Dobber et al. Cell Immunol. 1995 February;160(2):185-92 or Ozmen et al. J Immunol. 1993 Apr. 1; 150(7):2698-705. In some embodiments, the agent that is an antagonist or inhibitor of IFN-γ/IFNGR is a small molecule, a protein or peptide, or a nucleic acid.

In some embodiments, the agent is an antagonist or inhibitor of IL-10 or the IL-10 receptor (IL-10R). In some aspects, the agent is an antibody that neutralizes IL-10 activity, such as an antibody or antigen-binding fragment that binds to IL-10 or IL-10R. In some aspects, the IL-10 neutralizing antibody is any described in Dobber et al. Cell Immunol. 1995 February;160(2):185-92 or Hunter et al. J Immunol. 2005 Jun. 1; 174(11):7368-75. In some embodiments, the agent that is an antagonist or inhibitor of IL-10/IL-10R is a small molecule, a protein or peptide, or a nucleic acid.

In some embodiments, the agent is an antagonist or inhibitor of IL-1 or the IL-1 receptor (IL-1R). In some aspects, the agent is an IL-1 receptor antagonist, which is a modified form of IL-1R, such as anakinra (see, e.g., Fleischmann et al., (2006) Annals of the rheumatic diseases. 65(8):1006-12). In some aspects, the agent is an antibody that neutralizes IL-1 activity, such as an antibody or antigen-binding fragment that binds to IL-1 or IL-1R, such as canakinumab (see also EP 2277543). In some embodiments, the agent that is an antagonist or inhibitor of IL-1/IL-1R is a small molecule, a protein or peptide, or a nucleic acid.

In some embodiments, the agent is an antagonist or inhibitor of a tumor necrosis factor (TNF) or a tumor necrosis factor receptor (TNFR). In some aspects, the agent is an antibody that blocks TNF activity, such as an antibody or antigen-binding fragment that binds to a TNF, such as TNFα, or its receptor (TNFR, e.g., TNFRp55 or TNFRp75). In some aspects, the agent is selected from among infliximab, adalimumab, certolizumab pegol, golimumab and etanercept. In some embodiments, the agent that is an antagonist or inhibitor of TNF/TNFR is a small molecule, a protein or peptide, or a nucleic acid. In some embodiments, the agent is a small molecule that affects TNF, such as lenalidomide (see, e.g., Muller et al. (1999) Bioorganic & Medicinal Chemistry Letters. 9 (11):1625).

In some embodiments, the agent is an antagonist or inhibitor of signaling through the Janus kinase (JAK) and two Signal Transducer and Activator of Transcription (STAT) signaling cascade. JAK/STAT proteins are common components of cytokine and cytokine receptor signaling. In some embodiments, the agent that is an antagonist or inhibitor of JAK/STAT, such as ruxolitinib (see, e.g., Mesa et al. (2012) Nature Reviews Drug Discovery. 11(2):103-104), tofacitinib (also known as Xeljanz, Jakvinus tasocitinib and CP-690550), Baricitinib (also known as LY-3009104, INCB-28050), Filgotinib (G-146034, GLPG-0634), Gandotinib (LY-2784544), Lestaurtinib (CEP-701), Momelotinib (GS-0387, CYT-387), Pacritinib (SB1518), and Upadacitinib (ABT-494). In some embodiments, the agent is a small molecule, a protein or peptide, or a nucleic acid.

In some embodiments, the agent is a kinase inhibitor. In some embodiments, the agent is an inhibitor of Bruton's tyrosine kinase (BTK). In some embodiments, the inhibitor is or comprises ibrutinib or acalabrutinib (see, e.g., Barrett et al., ASH 58th Annual Meeting San Diego, CA Dec. 3-6, 2016, Abstract 654; Ruella et al., ASH 58th Annual Meeting San Diego, CA Dec. 3-6, 2016, Abstract 2159). In some embodiments, the agent is an inhibitor as described in U.S. Pat. Nos. 7,514,444; 8,008,309; 8,476,284; 8,497,277; 8,697,711; 8,703,780; 8,735,403; 8,754,090; 8,754,091; 8.957,079; 8,999,999; 9,125,889; 9,181,257; or 9,296,753.

In some embodiments, a device, such as absorbent resin technology with blood or plasma filtration, can be used to reduce cytokine levels. In some embodiments, the device used to reduce cytokine levels is a physical cytokine absorber, such as an extracorporeal cytokine absorber. In some embodiments, a physical cytokine absorber can be used to eliminate cytokines from the bloodstream in an ex vivo, extracorporeal manner. In some embodiments, the agent is a porous polymer. In some embodiments, the agent is CytoSorb (see, e.g., Basu et al. Indian J Crit Care Med. (2014) 18(12): 822-824).

IV. Compositions and Formulations

In some embodiments, the dose of cells comprising cells engineered to express a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

V. Kits and Articles of Manufacture

Also provided are articles of manufacture and kits containing engineered cells expressing a recombinant receptor or compositions thereof, and optionally instructions for use, for example, instructions for administering, according to the provided methods. In some embodiments, the instructions include methods for predicting and treating a toxicity. In some aspects, the methods can be used to determine if the subject is at risk or likely at risk for developing a toxicity following administration of a cell therapy.

Also provided is a kit containing a cell therapy, said cell therapy comprising cells genetically engineered to express a recombinant receptor; and instructions for administering the cell therapy to a subject having or suspected of having a tumor, wherein the instructions specify: (1) assessing, at two different time points, one or more factors indicative of disease burden in a subject that is a candidate for treatment with the cell therapy, wherein, at each of the two time points, the subject has not yet been administered the cell therapy and the factors indicative of disease burden comprises a volumetric measure of the tumor or a level or amount of an inflammatory marker in a sample from the subject, wherein the fold change in the factor assessed at the two different time points indicates the degree of risk or likely risk of the subject developing toxicity following administration of the cell therapy to the subject; and (2) (i) if the fold change is at or below a threshold value, administering the cell therapy to the subject, or (ii) administering the cell therapy to the subject, or (iii) administering the cell therapy to the subject at an amount, dose, setting, time or frequency that is based on the fold change. In some embodiments, the kit further comprises instructions for assessing the presence, level or amount of at least one of the inflammatory marker in two or more samples obtained at two or more time points from a subject that is a candidate for treatment with the cell therapy and determining a fold-change in the level or amount of the marker assessed at two of the two or more time points, wherein the fold change indicates the degree of risk or likely risk of the subject developing toxicity following administration of the cell therapy to the subject.

In some embodiments, the kit further comprises instructions for (i) administering a therapeutic regimen comprising the cell therapy to the subject if the fold change is at or below a threshold value, (ii) administering the cell therapy to the subject, or (iii) administering the therapeutic regimen to the subject at an amount, dose, setting, time or frequency based on the fold change of the at least one inflammatory marker.

In some embodiments, provided are articles of manufacture and/or kits that include a composition comprising a therapeutically effective amount of any of the engineered cells described herein, and instructions for administering, to a subject for treating a disease or condition. In some embodiments, the instructions can specify some or all of the elements of the methods provided herein. In some embodiments, the instructions specify particular instructions for administration of the cells for cell therapy, e.g., doses, timing, selection and/or identification of subjects for administration and conditions for administration. In some embodiments, the articles of manufacture and/or kits further comprise an agent for lymphodepleting therapy, and optionally further includes instructions for administering the lymphodepleting therapy. In some embodiments, the instructions can be included as a label or package insert accompanying the compositions for administration.

In some embodiments, the instructions specify the criteria for selection or identification of subjects for therapy. In some embodiments, such criteria include subjects having NHL or sub-type thereof and/or a high-risk NHL. In some embodiments, the instructions specify that the subjects to be treated include subjects having a disease or condition characterized or determined to be aggressive NHL, diffuse large B cell lymphoma (DLBCL), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL). In particular embodiments, the subject to be treated include subjects with aggressive NHL, in particular, with diffuse large B-cell lymphoma (DLBCL), not otherwise specified (NOS) and in some aspects including de novo and transformed from indolent). In some aspects, the subject or population to be treated may include and/or further include subjects with primary mediastinal B-cell lymphoma (PMBCL) or follicular lymphoma grade 3B (FL3B). In some embodiments, the subject or population to be treated include those subjects having poor performance status. In some aspects, the population to be treated includes, e.g., subjects having an Eastern Cooperative Oncology Group Performance Status (ECOG) that is anywhere from 0-2. In other aspects of any of the embodiments, the subjects to be treated include ECOG 0-1 or do not include ECOG2 subjects. In some embodiments, of any of the embodiments, the subjects to be treated have failed two or more prior therapies. In some embodiments, the subject does not have DLBCL transformed from marginal zone lymphoma (MZL) and chronic lymphocytic leukemia (CLL; Richter's) and/or has a DLBCL characterized as de novo or transformed from an indolent disease. In some embodiments, the subject has mantle cell lymphoma (MCL). In some embodiments, the instructions specify the administration of the cell therapy is for a subject that is or has been identified as having a double/triple hit lymphoma, has been identified as having a chemorefractory lymphoma, (e.g., chemorefractory DLBCL) and/or that has not achieved complete remission (CR) in response to a prior therapy.

In some embodiments, the instructions specify the dose of cells to be administered. For example, in some embodiments, the dose specified in the instructions include a total recombinant receptor (e.g., CAR)-expressing cells between about $1\times10^6$ and $3\times10^8$, e.g., in the range of about $1\times10^7$ to $2\times10^8$ such cells, such as $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values.

In some embodiments, the article of manufacture or kit comprises a container, optionally a vial comprising a plurality of CD4+ T cells expressing a recombinant receptor, and a container, optionally a vial comprising a plurality of CD8+ T cells expressing a recombinant receptor. In some embodiments, the article of manufacture or kit comprises a container, optionally a vial comprising a plurality of CD4+ T cells expressing a recombinant receptor, and further comprises, in the same container, a plurality of CD8+ T cells expressing a recombinant receptor. In some embodiments, a cryoprotectant is included with the cells. In some aspects the container is a bag.

In some embodiments, the container such as the vial comprises greater than or greater than about $10\times10^6$ T cells or recombinant receptor-expressing T cells, greater than or greater than about $15\times10^6$ T cells or recombinant receptor-expressing T cells, greater than or greater than about $25\times10^6$ T cells or recombinant receptor-expressing T cell. In some aspects, the vial comprises between about 10 million cells per ml and about 70 million cells per ml, between about 10 million cells per ml and about 50 million cells per ml, between about 10 million cells per ml and about 25 million cells per ml, between about 10 million cells per ml and about 15 million cells per ml, 15 million cells per ml and about 70 million cells per ml, between about 15 million cells per ml and about 50 million cells per ml, between about 15 million cells per ml and about 25 million cells per ml, between about 25 million cells per ml and about 70 million cells per ml, between about 25 million cells per ml and about 50 million cells per ml, and between about 50 million cells per ml and about 70 million cells per ml.

In some embodiments, the plurality of vials or plurality of cells or unit dose of cells specified for administration, collectively, comprises a dose of cells comprising from or from about $1\times10^5$ to $5\times10^8$ total recombinant receptor-expressing T cells or total T cells, $1\times10^5$ to $1\times10^8$ total recombinant receptor-expressing T cells or total T cells, from or from about $5\times10^5$ to $1\times10^7$ total recombinant receptor-expressing T cells or total T cells, or from or from about $1\times10^6$ to $1\times10^7$ total recombinant receptor-expressing T cells or total T cells, each inclusive. In some aspects, the article comprises one or more unit dose of the CD4+ and CD8+ cells or of the CD4+ receptor+ cells and CD8+ receptor+ cells, wherein the unit dose comprises between at or about $1\times10^7$ and at or about $2\times10^8$ recombinant receptor-expressing T cells, between at or about $5\times10^7$ and at or about $1.5\times10^8$ recombinant receptor-expressing T cells, at or about $5\times10^7$ recombinant receptor-expressing T cells, at or about $1\times10^8$ recombinant receptor-expressing T cells, or at or about $1.5\times10^8$ recombinant receptor-expressing T cells, optionally wherein the information in the article specifies administration of one or of a plurality of unit doses and/or a volume corresponding to such one or plurality of unit doses. In some cases, the article comprises one or more unit doses of the CD8+ cells, wherein the dose comprises between at or about $5\times10^6$ and at or about $1\times10^8$ recombinant receptor-expressing $CD8^+$ T cells, the dose comprises between at or about $1\times10^7$ and at or about $0.75\times10^8$ recombinant receptor-expressing CD8+ T cells, the dose comprises at or about $2.5\times10^7$ recombinant receptor-expressing CD8+ T cells, or the dose comprises at or about $5\times10^7$ recombinant receptor-expressing CD8+ T cells, or the dose comprises at or about $0.75\times10^8$ recombinant receptor-expressing CD8+ T cells, optionally wherein the information in the article specifies administration of one or of a plurality of unit doses and/or a volume corresponding to such one or plurality of unit doses. In some embodiments, the cells in the article, collectively, comprise a dose of cells comprising no more than $1\times10^8$ total recombinant receptor-expressing T cells or total T cells, no more than $1\times10^7$ total recombinant receptor-expressing T cells or total T cells, no more than $0.5\times10^7$ total recombinant receptor-expressing T cells or total T cells, no more than $1\times10^6$ total recombinant receptor-expressing T cells or total T cells, no more than $0.5\times10^6$ total recombinant receptor-expressing T cells or total T cells.

In some embodiments, the instructions can specify dosage regimen and timing of the administration. For example, in some embodiments, the instructions can specify administering to the subject multiple doses, e.g., two or more doses, of the cells. In some embodiments, the instructions specify the timing of the multiple doses, e.g., the second dose being administered approximately 4, 5, 6, 7, 8, 9, 10, 11, 12, 13, 14, 15, 16, 17, 18, 19, 20 or 21 days after the first dose; and/or the dosage amount in each dose.

In some embodiments, the article of manufacture or kit comprises a plurality of CD4+ T cells expressing a recombinant receptor, and instructions for administering, to a subject having a disease or condition, all or a portion of the plurality of CD4+ T cells and further administering CD8+ T cells expressing a recombinant receptor. In some embodiments, the instructions specify administering the CD4+ T cells prior to administering the CD8+ cells. In some cases, the instructions specify administering the CD8+ T cells prior to administering the CD4+ cells. In some embodiments, the article of manufacture or kit comprises a plurality of CD8+ T cells expressing a recombinant receptor, and instructions for administering, to a subject having a disease or condition, all or a portion of the plurality of CD8+ T cells and CD4+ T cells expressing a recombinant receptor. In some embodiments, the instructions specify dosage regimen and timing of the administration of the cells.

In some aspects, the instructions specify administering all or a portion of the CD4+ T cells and the all or a portion of the CD8+ T cells 0 to 12 hours apart, 0 to 6 hours apart or 0 to 2 hours apart. In some cases, the instructions specify administering the CD4+ T cells and the CD8+ T cells no more than 2 hours, no more than 1 hour, no more than 30 minutes, no more than 15 minutes, no more than 10 minutes or no more than 5 minutes apart.

In some embodiments, the instructions specify the dose or number of cells or cell type(s) and/or a ratio of cell types, e.g., individual populations or sub-types, such as the CD4+ to CD8+ ratio. In some embodiments, the populations or sub-types of cells, such as $CD8^+$ and $CD4^+$ T cells. For example, in some embodiments, the instructions specify that the cells are administered at or within a tolerated range of an output ratio of multiple cell populations or sub-types, such as CD4+ and CD8+ cells or sub-types, of between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9, 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, the articles of manufacture and/or kits further include one or more additional agents for therapy, e.g., lymphodepleting therapy and/or combination therapy, as described herein, and optionally instructions for administering the additional agents. In some examples, the articles of manufacture may further contain one or more therapeutic agents. In some embodiments, the therapeutic agent is an immunomodulatory agent, a cytotoxic agent, an anti-cancer agent or a radiotherapeutic.

In some embodiments, the articles of manufacture and/or kits further include one or more agents or treatments for treating, preventing, delaying, reducing or attenuating the development or risk of development of a toxicity and/or instructions for the administration of one or more agents or treatments for treating, preventing, delaying, reducing or attenuating the development or risk of development of a toxicity in the subject. In some embodiments, the agent is or comprises an anti-IL-6 antibody or anti-IL-6 receptor antibody. For example, in some embodiments, the agent or treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101. For example, in some embodiments, the agent or treatment is or comprises one or more of a steroid; an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta; or an agent capable of preventing, blocking or reducing microglial cell activity or function.

In some embodiments, the agent capable of preventing, blocking or reducing microglial cell activity or function is selected from an anti-inflammatory agent, an inhibitor of NADPH oxidase (NOX2), a calcium channel blocker, a sodium channel blocker, inhibits GM-CSF, inhibits CSF1R, specifically binds CSF-1, specifically binds IL-34, inhibits the activation of nuclear factor kappa B (NF-κB), activates a $CB_2$ receptor and/or is a $CB_2$ agonist, a phosphodiesterase inhibitor, inhibits microRNA-155 (miR-155) or upregulates microRNA-124 (miR-124). In some cases, the agent is selected from minocycline, naloxone, nimodipine, Riluzole, MOR103, lenalidomide, a cannabinoid (optionally WIN55 or 212-2), intravenous immunoglobulin (IVIg), ibudilast, anti-miR-155 locked nucleic acid (LNA), MCSI 10, PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945, emactuzumab, IMC-CS4, FPA008, LY-3022855, AMG-820 and TG-3003. In some embodiments, the agent is an inhibitor of colony stimulating factor 1 receptor (CSF1R). For example, the agent PLX-3397, PLX647, PLX108-D1, PLX7486, JNJ-40346527, JNJ28312141, ARRY-382, AC-708, DCC-3014, 5-(3-methoxy-4-((4-methoxybenzyl)oxy)benzyl)pyrimidine-2,4-diamine (GW2580), AZD6495, Ki20227, BLZ945 or a pharmaceutical salt or prodrug thereof; emactuzumab, IMC-CS4, FPA008, LY-3022855, AMG-820 and TG-3003 or is an antigen-binding fragment thereof, or a combination of any of the foregoing.

In some embodiments, the articles of manufacture and/or kits further include one or more reagents for assaying biological samples, e.g., biological samples from subjects who are candidates for administration or who have been administered the therapy, and optionally instructions for use of the reagents or assays. In some embodiments, the biological sample is or is obtained from a blood, plasma or serum sample. In some embodiments, the reagents can be used prior to the administration of the cell therapy or after the administration of cell therapy, for diagnostic purposes, to identify subjects and/or to assess treatment outcomes and/or toxicities. For example, in some embodiments, the article of manufacture and/or kits further contain reagents for measuring the level of particular biomarkers, e.g., inflammatory markers, that are associated with toxicity, and instructions for measuring. In some embodiments, the reagents include components for performing an in vitro assay to measure the inflammatory markers, such as an immunoassay, an aptamer-based assay, a histological or cytological assay, or an mRNA expression level assay. In some embodiments, the in vitro assay is selected from among an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay. In some aspects, the reagent is a binding reagent that specifically binds the inflammatory markers. In some cases, the binding reagent is an antibody or antigen-binding fragment thereof, an aptamer or a nucleic acid probe.

In some embodiments, the articles of manufacture and/or kits comprise one or more reagent capable of detecting one or more inflammatory markers and instructions for using the reagent to assay a biological sample from a subject that is a candidate for treatment, wherein the one or more inflammatory marker is selected from C-reactive protein (CRP), erythrocyte sedimentation rate (ESR), albumin, ferritin, β2 microglobulin (β2-M), or lactate dehydrogenase (LDH). In some embodiments, instructions for assaying presence or absence, level, amount, or concentration of an inflammatory marker in the subject at two time points and determining a fold change in the inflammatory marker between the two time points. In some cases, the instructions specify that the fold change in inflammatory marker is compared to a threshold fold change of the inflammatory marker.

In some embodiments, the articles of manufacture and/or kits comprise instructions for measuring a volumetric measure of tumor burden. In some cases, the instructions specify measuring a volumetric measure of tumor(s) such as a sum of the products of diameters (SPD), longest tumor diameters (LD), sum of longest tumor diameters (SLD), tumor volume, necrosis volume, necrosis-tumor ratio (NTR), peritumoral edema (PTE), and edema-tumor ratio (ETR) at two time points prior to administration of the cell therapy. In some embodiments, instructions are provided for using imaging techniques to assess tumor burden in the subject at two time points and determining a fold change in the volumetric measurement of tumor the two time points. In some cases, the instructions specify that the fold change in volumetric measurement of tumor is compared to a threshold fold change of the volumetric measurement.

In some embodiments, the instructions are included which specify, if the fold change in the level, amount or concentration of the inflammatory marker in the sample is at or above a threshold fold change level for the inflammatory marker, administering to the subject an agent or other treatment capable of treating, preventing, delaying, reducing or attenuating the development or risk of development of a toxicity (i) prior to, (ii) within one, two, or three days of, (iii) concurrently with and/or (iv) at first fever following, the initiation of administration of the cell therapy to the subject. In some cases, the instructions specify that if the level, amount or concentration of the inflammatory marker in the sample is at or above a threshold level for the inflammatory marker, the cell therapy is administered to the subject at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy. In some cases, the instructions specify that if the level, amount or concentration of the inflammatory marker in the sample is at or above a threshold level for the inflammatory marker, the cell therapy is administered in an in-patient setting and/or with admission to the hospital for one or more days, optionally wherein the cell therapy is otherwise to be administered to subjects on an outpatient basis or without admission to the hospital for one or more days.

In some embodiments, the instructions for administering the cell therapy specify, if the level, amount or concentration of the inflammatory marker in the sample, is below a threshold level, administering to the subject the cell therapy, optionally at a non-reduced dose, optionally on an outpatient basis or without admission to the hospital for one or more days. In some embodiments, the instructions for administering the cell therapy specify, if the level, amount or concentration of the inflammatory marker in the sample, is below a threshold level, prior to or concurrently with administering the cell therapy and/or prior to the development of a sign or symptom of a toxicity other than fever, an agent or treatment capable of treating, preventing, delaying, or attenuating the development of the toxicity is not administered to the subject. In some aspects, the instructions for administering the cell therapy specify that if the level, amount or concentration of the inflammatory marker in the sample, is below a threshold level, the administration of the cell therapy is to be or may be administered to the subject on an outpatient setting and/or without admission of the subject to the hospital overnight or for one or more consecutive days and/or is without admission of the subject to the hospital for one or more days.

The articles of manufacture and/or kits may further include a cell therapy and/or further include instructions for use with, prior to and/or in connection with treatment with the cell therapy. In some embodiments, the instructions are included for administering the agent and the instructions specify if the fold change in level, amount or concentration of the inflammatory marker in the sample, is at or above a threshold level administering to the subject the agent. In some aspects, the instructions further specify administering a cell therapy to the subject, wherein administration of the agent is to be carried out (i) prior to, (ii) within one, two, or three days of, (iii) concurrently with and/or (iv) at first fever following, the initiation of administration of the cell therapy to the subject.

The articles of manufacture or kits include one or more containers, typically a plurality of containers, packaging material, and a label or package insert on or associated with the container or containers and/or packaging, generally including instructions for administration of the cells to a subject. The articles of manufacture and/or kits may include a container and a label or package insert on or associated with the container.

In some embodiments, the containers contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more) the cells to be administered in the first or any one or more consecutive dose(s). It may be the lowest dose or lowest possible dose of the cells that would be administered to the subject in connection with the administration method. In some embodiments, the unit dose is the minimum number of cells or number of cells or the minimum number of reference units or the target reference units or reference units within a target range that would be administered in a single dose to any subject having a particular disease or condition or any subject, according to the methods herein.

Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may include (a) a first container with a composition contained therein, wherein the composition includes engineered cells expressing a recombinant receptor; and (b) a second container with a composition contained therein, wherein the composition includes the second agent. In some embodiments, the article of manufacture may include (a) a first container with a first composition contained therein, wherein the composition includes a subtype of engineered cells expressing a recombinant receptor; and (b) a second container with a composition contained therein, wherein the composition includes a different subtype of engineered cells expressing a recombinant receptor. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 mL capacity, such as between at or about 10 and at or about 100 or between at or about 10 and at or about 500 mL capacity, each inclusive. In some embodiments, the containers, e.g., bags, are and/or are made from material which is stable and/or provide stable storage and/or maintenance of cells at one or more of various temperatures, such as in cold temperatures, e.g. below at or about or at or about $-20°$ C., $-80°$ C., $-120°$ C., $135°$ C. and/or temperatures suitable for cryopreservation, and/or other temperatures, such as temperatures suitable for thawing the cells and body temperature such as at or about $37°$ C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more consecutive doses of the cells, e.g., according to any of the embodiments of the provided methods. In some embodiments, the instructions specify administration, in a first dose, of one unit dose, e.g., the contents of a single individual container in the article of manufacture, followed by one or more consecutive doses at a specified time point or within a specified time window and/or after the detection of the presence or absence or amount or degree of one or more factors or outcomes in the subject.

In some embodiments, the instructions specify administering one or more of the unit doses to the subject.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

VI. Definitions

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. In some embodiments, sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

VII. EXEMPLARY EMBODIMENTS

Among the provided embodiments are:
1. A method of assessing a risk of a toxicity or a toxicity-related outcome, following administration of a cell therapy, the method comprising:
   (1) assessing a factor indicative of disease burden at two time points prior to receiving a cell therapy from a subject that is a candidate for receiving a cell therapy for treatment of a disease or condition; and
   (2) determining a fold change in the factor indicative of disease burden between the two time points, wherein the fold change indicates the risk or likely risk of the subject developing a toxicity following administration of the therapy to the subject.
2. The method of embodiment 1, wherein the factor indicative of disease burden is a volumetric measure of a tumor or is an inflammatory marker in a sample from a subject.
3. The method of embodiment 2, wherein the factor indicative of disease burden is a volumetric measure and the volumetric measure is a sum of the products of diameters (SPD), longest tumor diameters (LD), sum of longest tumor diameters (SLD), tumor volume, necrosis volume, necrosis-tumor ratio (NTR), peritumoral edema (PTE), and edema-tumor ratio (ETR).
4. The method of embodiment 2 or embodiment 3, wherein the volumetric measure is measured using computed tomography (CT), positron emission tomography (PET), and/or magnetic resonance imaging (MRI) of the subject.
5. The method of embodiment 2, wherein the factor indicative of disease burden is an inflammatory marker and the inflammatory marker is C-reactive protein (CRP), erythrocyte sedimentation rate (ESR), albumin, ferritin, β2 microglobulin (β2-M), or lactate dehydrogenase (LDH).
6. The method of embodiment 2 or embodiment 5, wherein the sample is or comprises a blood sample, plasma sample, or serum sample.
7. The method of any of embodiments 2, 5 or 6, wherein the inflammatory marker is assessed using a colorimetric assay or an immunoassay.
8. The method of embodiment 7, wherein the inflammatory marker is assessed using an immunoassay and the immunoassay is selected from enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).
9. The method of any of embodiments 1-8, wherein the subject is a human.
10. The method of any of embodiments 1-9, wherein the two time points comprises a first time point and a second time point, and wherein the fold change is a ratio of the factor indicative of disease burden at the first time point and the second time point.
11. The method of any of embodiments 1-10, wherein the two time points are both no more than one month or two months prior to receiving the cell therapy.
12. The method of any of embodiments 1-11, wherein the two time points are not less than one week, two weeks, three weeks, four weeks, or five weeks apart.
13. The method of any of embodiments 1-12, wherein the two time points are not less than three weeks apart.
14. The method of any of embodiments 1-13, wherein the two time points are not more than four weeks apart, five weeks, or six weeks apart.
15. The method of any of embodiments 1-14, wherein the second time point is more than 1, 2, 3, 4, 5, 6, or 7 days before administration of the cell therapy.
16. The method of any of embodiments 1-13, wherein the cell therapy comprises cells engineered to express a recombinant receptor.
17. The method of any of embodiments 1-16, wherein the toxicity is neurotoxicity and/or cytokine release syndrome (CRS).
18. The method of any of embodiments 1-17, wherein the toxicity is early toxicity that develops within 7 days of administration of the cell therapy.
19. The method of any of embodiments 1-18, wherein the toxicity develops within 3, 4, 5, 6, or 7 days of administration of the cell therapy.
20. The method of any of embodiments 1-19, wherein the toxicity is a first sign of a fever or is a sustained fever following administration of the cell therapy.
21. The method of any of embodiments 1-20, wherein:
   the subject is or is likely at risk of developing toxicity if the fold change is at or above a threshold value; or
   the subject is not or is likely not at risk of developing toxicity if the fold change is below a threshold value.
22. The method of embodiment 21, wherein the threshold value is a value that:
   i) is within 25%, within 20%, within 15%, within 10%, or within 5% above the average fold change of the factor indicative of disease burden and/or is within a standard deviation above the average fold change of the factor indicative of disease burden in a plurality of control subjects;
   ii) is above the highest fold change of the factor indicative of disease burden, optionally within 50%, within 25%, within 20%, within 15%, within 10%, or within 5% above such highest fold change, measured in at least one subject from among a plurality of control subjects; and/or
   iii) is above the highest fold change as measured among more than 75%, 80%, 85%, 90%, or 95%, or 98% of subjects from a plurality of control subjects.
23. The method of embodiment 22, wherein the plurality of control subjects are a group of subjects prior to receiving a cell therapy for treating a disease or condition, said cell therapy containing cells genetically engineered with a recombinant receptor, wherein each of the subjects of the group went on to develop toxicity, optionally early toxicity, optionally a fever or a sustained fever, within 7 days after receiving the cell therapy for treating the same disease or condition.
24. The method of any of embodiment 1-21, wherein if the subject is indicated as likely to develop toxicity, selecting the subject for administration of a therapeutic regimen, the therapeutic regimen comprising administering to the subject:
   i. an agent or other treatment capable of treating, preventing, delaying, reducing or attenuating the development or risk of development of a toxicity and the cell therapy, wherein administration of the agent is to be administered (i) prior to, (ii) within one, two, or three days of, (iii) concurrently with and/or (iv) at first fever following, the initiation of administration of the cell therapy to the subject;

ii. the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or iii. the cell therapy in an in-patient setting and/or with admission to the hospital for one or more days, optionally wherein the cell therapy is otherwise to be administered to subjects on an outpatient basis or without admission to the hospital for one or more days; or iv. an alternative therapeutic treatment other than the cell therapy.

25. The method of any of embodiments 1-21, wherein if subject is indicated as likely not at risk of developing toxicity, selecting the subject for administration of a therapeutic regimen, the therapeutic regimen comprising administering to the subject:

i. the cell therapy, optionally at a non-reduced dose, optionally on an outpatient basis or without admission to the hospital for one or more days;

ii. the cell therapy, wherein administration of the cell therapy does not comprise administering, prior to or concurrently with administering the cell therapy and/or prior to the development of a sign or symptom of toxicity other than fever, an agent or treatment capable of treating, preventing, delaying, or attenuating the development of the toxicity; or iii. the cell therapy in an outpatient setting and/or without admission of the subject to the hospital overnight or for one or more consecutive days and/or is without admission of the subject to the hospital for one or more days.

26. The method of any of embodiments 1-21, wherein if the subject is indicated as likely to develop toxicity following administration of the cell therapy, the cell therapy is not administered to the subject.

27. The method of embodiment 24 or embodiment 25, further comprising administering the therapeutic regimen to the selected subject.

28. A method of treatment, the method comprising administering a therapeutic regimen to a subject that is a candidate for receiving a cell therapy for treatment of a disease or condition, wherein the administration is carried out following or based on the results of assessing the subject for a fold change in a factor indicative of disease burden between two time points prior to receiving a cell therapy.

29. The method of embodiment 28, wherein the factor indicative of disease burden is a volumetric measure of a tumor or is an inflammatory marker in a sample from a subject.

30. The method of embodiment 29, wherein the factor indicative of disease burden is a volumetric measure and the volumetric measure is a sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR).

31. The method of embodiment 29 or embodiment 30, wherein the volumetric measure is measured using computed tomography (CT), positron emission tomography (PET), and/or magnetic resonance imaging (MRI) of the subject.

32. The method of embodiment 29, wherein the factor indicative of disease burden is an inflammatory marker and the inflammatory marker is C-reactive protein (CRP), erythrocyte sedimentation rate (ESR), albumin, ferritin, β2 microglobulin (β2-M), or lactate dehydrogenase (LDH).

33. The method of embodiment 29 or embodiment 32, wherein the sample is or comprises a blood sample, plasma sample, or serum sample.

34. The method of any of embodiments 29, 32 or 33, wherein the inflammatory marker is assessed using a colorimetric assay or an immunoassay.

35. The method of embodiment 34, wherein the inflammatory marker is assessed using an immunoassay and the immunoassay is selected from enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

36. The method of any of embodiments 28-34, wherein the subject is a human.

37. The method of any of embodiments 28-36, wherein the two time points comprises a first time point and a second time point, and wherein the fold change is a ratio of the factor indicative of disease burden at the first time point and the second time point.

38. The method of any of embodiments 28-37, wherein the two time points are both no more than one month or two months prior to receiving the cell therapy.

39 The method of any of embodiments 28-38, wherein the two time points are not less than one week, two weeks, three weeks, four weeks, or five weeks apart.

40. The method of any of embodiments 28-39, wherein the two time points are not less than three weeks apart.

41. The method of any of embodiments 28-40 wherein the two time points are not more than four weeks apart, five weeks, or six weeks apart.

42. The method of any of embodiments 28-41, wherein the second time point is more than 1, 2, 3, 4, 5, 6, or 7 days before administration of the cell therapy.

43. The method of any of embodiments 28-42, wherein the cell therapy comprises cells engineered to express a recombinant receptor.

44. The method of any of embodiments 28-43, wherein the fold change in the factor indicative of disease burden is associated with a risk of developing toxicity following administration of the cell therapy.

45. The method of any of embodiments 28-44, wherein the toxicity is neurotoxicity and/or cytokine release syndrome (CRS).

46. The method of any of embodiments 28-45, wherein the toxicity is early toxicity that develops within 7 days of administration of the cell therapy.

47. The method of any of embodiments 28-46, wherein the toxicity develops within 3, 4, 5, 6, or 7 days of administration of the cell therapy.

48. The method of any of embodiments 28-47, wherein the toxicity is a first sign of a fever or is a sustained fever following administration of the cell therapy.

49. The method of any of embodiments 29-48, wherein the assessing of the fold change in a factor indicative of disease burden between two time points comprises a comparison to a threshold value, wherein the comparison indicates the risk or likely risk of the subject developing toxicity following administration of the cell therapy to the subject.

50. The method of any of embodiments 28-49, wherein the fold change in the factor indicative of disease burden correlates to a risk that the subject is or is likely to develop toxicity following administration of the cell therapy when it is administered.

51. The method of any of embodiments 28-50, wherein:
the subject is or is likely at risk of developing toxicity if the fold change is at or above a threshold value; or
the subject is not or is likely not at risk of developing toxicity if the fold change is below a threshold value.

52. The method of embodiment 51, wherein the threshold value is a value that:
  i) is within 25%, within 20%, within 15%, within 10%, or within 5% above the average fold change of the factor indicative of disease burden and/or is within a standard deviation above the average fold change of the factor indicative of disease burden in a plurality of control subjects;
  ii) is above the highest fold change of the factor indicative of disease burden, optionally within 50%, within 25%, within 20%, within 15%, within 10%, or within 5% above such highest fold change, measured in at least one subject from among a plurality of control subjects; and/or
  iii) is above the highest fold change as measured among more than 75%, 80%, 85%, 90%, or 95%, or 98% of subjects from a plurality of control subjects.

53. The method of embodiment 52, wherein the plurality of control subjects are a group of subjects prior to receiving a cell therapy for treating a disease or condition, said cell therapy containing cells genetically engineered with a recombinant receptor, wherein each of the subjects of the group went on to develop toxicity, optionally early toxicity, optionally a fever or a sustained fever, within 7 days after receiving the cell therapy for treating the same disease or condition.

54. The method of any of embodiments 28-53, wherein if the assessing indicates the subject is or is likely to develop toxicity following administration of the cell therapy, the therapeutic regimen comprises administering to the subject:
  i. an agent or other treatment capable of treating, preventing, delaying, reducing or attenuating the development or risk of development of a toxicity and the cell therapy, wherein administration of the agent is to be administered (i) prior to, (ii) within one, two, or three days of, (iii) concurrently with and/or (iv) at first fever following, the initiation of administration of the cell therapy to the subject;
  ii. the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or
  iii. the cell therapy in an in-patient setting and/or with admission to the hospital for one or more days, optionally wherein the cell therapy is otherwise to be administered to subjects on an outpatient basis or without admission to the hospital for one or more days; or
  iv. an alternative therapeutic treatment other than the cell therapy.

55. The method of any of embodiments 28-50, wherein if the assessing indicates the subject is not or is likely not to develop toxicity following administration of the cell therapy, the therapeutic regimen comprises administering to the subject:
  i. the cell therapy, optionally at a non-reduced dose, optionally on an outpatient basis or without admission to the hospital for one or more days;
  ii. the cell therapy, wherein administration of the cell therapy does not comprise administering, prior to or concurrently with administering the cell therapy and/or prior to the development of a sign or symptom of toxicity other than fever, an agent or treatment capable of treating, preventing, delaying, or attenuating the development of the toxicity; or
  iii. the cell therapy in an outpatient setting and/or without admission of the subject to the hospital overnight or for one or more consecutive days and/or is without admission of the subject to the hospital for one or more days.

56. The method of any of embodiments 28-50 wherein if the assessing indicates the subject is or is likely to develop toxicity following administration of the cell therapy, the cell therapy is not administered to the subject.

57. The method of any of embodiments 1-56, wherein the disease or condition is a cancer.

58. The method of embodiment 57, wherein the cancer is a myeloma, lymphoma or leukemia.

59. The method of any of embodiments 1-58, wherein the disease or condition is a B cell malignancy.

60. The method of embodiment 59, wherein the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

61. The method of any of embodiments 27-60, wherein:
greater than or greater than about 30%, 35%, 40%, or 50% of the subjects treated according to the method do not exhibit any grade of cytokine release syndrome (CRS) or neurotoxicity; and/or
at least at or about 45, 50, 60, 65, 70, 75, 80, 85, 90, 95% or about 100% of subjects treated according to the method do not exhibit severe CRS, optionally grade 3 or higher, prolonged grade 3 or higher or grade 4 or 5 CRS; and/or
at least at or about 45, 50, 60, 65, 70, 75, 80, 85, 90, 95% or about 100% of subjects treated according to the method do not exhibit severe neurotoxicity, optionally grade 3 or higher, prolonged grade 3 or higher or grade 4 or 5 neurotoxicity; and/or
at least at or about 45, 50, 60, 65, 70, 75, 80, 85, 90, 95% or about 100% of subjects treated according to the method do not exhibit cerebral edema.

62. The method of any of embodiments 27-61, wherein:
prior to initiation of administration of the dose of cells, the subject has not been administered an agent or treatment capable of treating, preventing, delaying, reducing or attenuating the development or risk of development of a toxicity; and/or
the subject is not administered an agent or treatment for the treatment or prevention or reduction or attenuation of a neurotoxicity and/or a cytokine release syndrome or risk thereof, within a period of time following administration of the dose, which period of time is optionally at or about 1, 2, 3, 4, 5 days or is optionally at or about 6, 7, 8, 9, 10, 11 days or is optionally 1 or 2 or 3 or 4 weeks; and/or
the subject is not administered an agent or treatment for the treatment or prevention or reduction or attenuation of a neurotoxicity and/or a cytokine release syndrome or risk thereof, following administration of the dose, prior to or unless the subject exhibits a sign or symptom of the toxicity and/or prior to or unless the subject exhibits a sign or symptom of the toxicity other than a fever, optionally wherein the fever is not a sustained fever or the fever is or has been reduced or reduced by more than 1° C. after treatment with an antipyretic; and/or the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

63. The method of any of embodiments 27-62, wherein:
prior to initiation of administration of the dose of cells, the subject has not been administered an anti-IL-6 or anti-IL-6R antibody, optionally tocilizumab or siltuximab, and/or has not been administered a steroid, optionally dexamethasone the subject is not administered an anti-IL-6 or anti-IL-6R antibody, optionally tocilizumab or siltuximab, and/or has not been administered a steroid, optionally dexamethasone, within a period of time following administration of the dose, which period of time is optionally at or about 1, 2, 3, 4, 5 days or is optionally at or about 6, 7, 8, 9, 10, 11 days or is optionally 1 or 2 or 3 or 4 weeks; and/or the subject is not administered an anti-IL-6 or anti-IL-6R antibody, optionally tocilizumab or siltuximab, and/or has not been administered a steroid, optionally dexamethasone, following administration of the cell dose, prior to, or unless, the subject exhibits a sign or symptom of a toxicity, optionally a neurotoxicity or CRS, and/or prior to, or unless, the subject exhibits a sign or symptom of a toxicity, optionally a neurotoxicity or CRS, other than a fever, optionally wherein the fever is not a sustained fever or the fever is or has been reduced or reduced by more than 1° C. after treatment with an antipyretic; and/or the administration and any follow-up is carried out on an outpatient basis and/or without admitting the subject to a hospital and/or without an overnight stay at a hospital and/or without requiring admission to or an overnight stay at a hospital, optionally unless or until the subject exhibits a sustained fever or a fever that is or has not been reduced or not reduced by more than 1° C. after treatment with an antipyretic.

64. The method of any of embodiments 27-63, wherein:
the administration is carried out on an outpatient basis and/or without requiring admission to or an overnight stay at a hospital; and if the subject exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

65. The method of any of embodiments 1-64, wherein the cell therapy is or comprises tumor infiltrating lymphocytic (TIL) therapy.

66. The method of any of embodiments 1-64, wherein the cell therapy comprises cells engineered to express a recombinant receptor that specifically binds to an antigen associated with a disease or condition and/or expressed in cells associated with the disease or condition.

67. The method of any of embodiments 1-66, wherein the cell therapy is an adoptive cell therapy.

68. The method of embodiment 66 or embodiment 67, wherein the cells comprise immune cells.

69. The method of embodiment 68, wherein the immune cells are or comprise T cells or NK cells.

70. The method of embodiment 69, wherein the immune cells are or comprise T cells and the T cells comprise CD4+ and/or CD8+ T cells.

71. The method of any of embodiments 1-70, wherein the cell therapy is a T cell therapy comprising genetically engineered cells expressing a recombinant receptor.

72. The method of embodiment 71, wherein the recombinant receptor is a T cell receptor or a functional non-T cell receptor.

73. The method of embodiment 71 or embodiment 72, wherein the recombinant receptor specifically binds to an antigen associated with a disease or condition and/or expressed in cells associated with the disease or condition.

74. The method of embodiment 73, wherein the antigen is selected from among Trophoblast glycoprotein (TPBG also known as 5T4), 8H9, αvβ6 integrin (avb6 integrin), B7-H3, B7-H6, B cell maturation antigen (BCMA), carbonic anhydrase 9 (CA9, also known as CAIX or G250), a cancer-testes antigen, carbonic anhydrase 9 (CAIX), C—C Motif Chemokine Ligand 1 (CCL-1), CD19, CD20, CD22, hepatitis B surface antigen, CD23, CD24, CD30, CD33, CD38, CD44, CD44v6, CD44v7/8, CD123, CD133, CD138, CD171, carcinoembryonic antigen (CEA), a cyclin, cyclin A2, c-Met, dual antigen, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), ephrinB2, type III epidermal growth factor receptor mutation (EGFR vIII), estrogen receptor, folate receptor alpha, folate binding protein (FBP), Fc receptor like 5 (FCRL5; also known as Fc receptor homolog 5 or FCRH5), fetal acetylcholine receptor (Fetal AchR), G250/CAIX, ganglioside GD2, ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), Human leukocyte antigen A1 (HLA-A1), Human leukocyte antigen A2 (HLA-A2), IL-22 receptor alpha (IL-22R-alpha), IL-13 receptor alpha 2 (IL-13Ra2), kinase insert domain receptor (kdr), kappa light chain, Leucine Rich Repeat Containing 8 Family Member A (LRRC8A), Lewis Y, L1-cell adhesion molecule (L1-CAM), CE7 epitope of L1-CAM, Melanoma-associated antigen (MAGE)-A1, MAGE-A3, MAGE-A6, MAGE-A10, melan A (MART-1), mesothelin (MSLN), murine cytomegalovirus (CMV), mucin 1 (MUC1), MUC16, neural cell adhesion molecule (NCAM), natural killer group 2 member D (NKG2D), NKG2D ligands, cancer/testis antigen 1B (CTAG, also known as NY-ESO-1 and LAGE-2), 0-acetylated GD2 (OGD2), oncofetal antigen, Preferentially expressed antigen of melanoma (PRAME), a prostate specific antigen, prostate stem cell antigen (PSCA), progesterone receptor, survivin, prostate specific membrane antigen (PSMA), Receptor Tyrosine Kinase Like Orphan Receptor 1 (ROR1), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGF receptors; VEGFR), vascular endothelial growth factor receptor 2 (VEGF-R2), Wilms Tumor 1 (WT-1), a pathogen-specific antigen.

75. The method of embodiment 73 or embodiment 74, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

76. The method of any of embodiments 71-75, wherein the genetically engineered cells comprise T cells or NK cells.

77. The method of any of embodiments 71-76, wherein the genetically engineered cells comprise T cells, and the T cells comprise CD4+ and/or CD8+ T cells.

78. The method of embodiment 77, wherein the T cells are primary T cells obtained from a subject.

79. The method of any of embodiments 1-78, wherein the cells of the cell therapy are autologous to the subject or the cells are allogeneic to the subject.

80. The method of any of embodiments 21, 22, 49, 51, or 52, wherein the threshold fold change for SPD is about 5 fold, 6 fold, 7 fold, 8 fold, or 9 fold.

81. The method of any of embodiments 1-80, wherein the cell therapy comprises the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive.

82. The method of any of embodiments 1-81, wherein the cell therapy comprises the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

83. A kit, comprising (a) a cell therapy, said cell therapy comprising cells genetically engineered with a recombinant receptor; and (b) instructions for administering the cell therapy to a subject, wherein the instructions specify:
(1) assessing one or more factors indicative of tumor burden in a subject that is a candidate for treatment with the cell therapy, wherein the assessing is performed at two time points prior to the subject receiving the cell therapy, and the factor indicative of tumor burden is a volumetric measure of the tumor or is an inflammatory marker in a sample from a subject; and
(2) administering the cell therapy to the subject based on the fold change in the factor indicative of disease burden between the two time points, wherein the fold change indicates the risk or likely risk of the subject developing toxicity following administration of the cell therapy to the subject.

84. A kit, comprising (a) a cell therapy, said cell therapy comprising cells genetically engineered with a recombinant receptor; and (b) one or more reagents for assaying one or more factor indicative of disease burden, wherein the factor indicative of disease burden is an inflammatory marker selected from C-reactive protein (CRP), erythrocyte sedimentation rate (ESR), albumin, ferritin, β2 microglobulin (β2-M), or lactate dehydrogenase (LDH).

85. The kit of embodiment 84, wherein the kit further comprises instructions for assessing the presence, level or amount at least one of the inflammatory marker in two or more samples obtained at two time points from a subject that is a candidate for treatment with the cell therapy and determining the fold-change in the factor between the two time points, wherein the fold change indicates the risk or likely risk of the subject developing toxicity following administration of the cell therapy to the subject.

86. The kit of embodiment 85, wherein the kit further comprises instructions for administering a therapeutic regimen comprising the cell therapy to the subject following or based on the fold change of the at least one inflammatory marker.

87. A kit, comprising (a) a cell therapy, said cell therapy comprising cells genetically engineered with a recombinant receptor; and (b) instructions for administering a therapeutic regimen comprising the cell therapy following or based on the results of assessing the subject for a fold change in a factor indicative of disease burden between two time points prior to receiving a cell therapy, wherein the subject is a candidate for treatment with the cell therapy.

88. The kit of embodiment 87, wherein the factor indicative of disease burden is a volumetric measure of a tumor or is an inflammatory marker in a sample from a subject.

89. The kit of any of embodiments 83, 87, or 88, wherein the factor indicative of disease burden is a volumetric measure and the volumetric measure is a sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR).

90. The kit of any of embodiments 83, or 87-89, wherein the volumetric measure is measured using computed tomography (CT), positron emission tomography (PET), and/or magnetic resonance imaging (MRI) of the subject.

91. The kit of any of embodiments 83-88, wherein the kit comprises reagents for detecting C-reactive protein (CRP), erythrocyte sedimentation rate (ESR), albumin, ferritin, β2 microglobulin (β2-M), or lactate dehydrogenase (LDH).

92. The kit of any of embodiments 83-88 or 91, wherein the inflammatory marker is assessed using a colorimetric assay or an immunoassay.

93. The kit of any of embodiments 83-88 or 91-92, wherein the inflammatory marker is assessed using an immunoassay and the immunoassay is selected from enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

94. The kit of any of embodiments 83-88 or 91-93, wherein the sample is or comprises a blood sample, plasma sample, or serum sample.

95. The kit of any of embodiments 83-94, wherein the subject is a human.

96. The kit of any of embodiments 83-95, wherein the two time points comprises a first time point and a second time point, and wherein the fold change is a ratio of the factor indicative of disease burden at the a first time point and a second time point.

97. The kit of any of embodiments 83-96, wherein the two time points are both no more than one month or two months prior to receiving the cell therapy.

98. The kit of any of embodiments 83-97 wherein the two time points are not less than one week, two weeks, three weeks, four weeks, or five weeks apart.

99. The kit of any of embodiments 83-98, wherein the two time points are not less than three weeks apart.

100. The kit of any of embodiments 83-99 wherein the two time points are not more than four weeks apart, five weeks, or six weeks apart.

101. The kit of any of embodiments 83-100, wherein the second time point is more than 1, 2, 3, 4, 5, 6, or 7 days before administration of the cell therapy.

102. The kit of any of embodiments 83-101, wherein:
the instructions specify that the fold change in the factor indicative of disease burden indicates the subject is or is likely at risk of developing toxicity if the fold change is at or above a threshold value; or
the instructions specify that the fold change in the factor indicative of disease burden indicates the subject is not or is likely not at risk of developing toxicity if the fold change is below a threshold value.

103. The kit of embodiment 102, wherein the threshold value is a value that:
i) is within 25%, within 20%, within 15%, within 10%, or within 5% above the average fold change of the factor indicative of disease burden and/or is within a standard deviation above the average fold change of the factor indicative of disease burden in a plurality of control subjects;
ii) is above the highest fold change of the factor indicative of disease burden, optionally within 50%, within 25%, within 20%, within 15%, within 10%, or within 5% above such highest fold change, measured in at least one subject from among a plurality of control subjects; and/or
iii) is above the highest fold change as measured among more than 75%, 80%, 85%, 90%, or 95%, or 98% of subjects from a plurality of control subjects.

104. The kit of embodiment 103, wherein the plurality of control subjects are a group of subjects prior to receiving a cell therapy for treating a disease or condition, said cell therapy containing cells genetically engineered with a recombinant receptor, wherein each of the subjects of the group went on to develop toxicity, optionally early toxicity, optionally a fever or a sustained fever, within 7 days after receiving the cell therapy for treating the same disease or condition.

105. The kit of any of embodiments 87-104, wherein the instructions specify if the fold change indicates the subject is or is likely to develop toxicity, selecting the subject for administration of a therapeutic regimen, the therapeutic regimen comprising administering to the subject:
i. an agent or other treatment capable of treating, preventing, delaying, reducing or attenuating the development or risk of development of a toxicity and the cell therapy, wherein administration of the agent is to be administered (i) prior to, (ii) within one, two, or three days of, (iii) concurrently with and/or (iv) at first fever following, the initiation of administration of the cell therapy to the subject;
ii. the cell therapy at a reduced dose or at a dose that is not associated with risk of developing toxicity or severe toxicity, or is not associated with a risk of developing a toxicity or severe toxicity in a majority of subjects, and/or a majority of subjects having a disease or condition that the subject has or is suspected of having, following administration of the cell therapy; and/or
iii. the cell therapy in an in-patient setting and/or with admission to the hospital for one or more days, optionally wherein the cell therapy is otherwise to be administered to subjects on an outpatient basis or without admission to the hospital for one or more days; or
iv. an alternative therapeutic treatment other than the cell therapy.

106. The kit of any of embodiments 87-104, wherein the instructions specify if the fold change indicates the subject is not or is likely not at risk of developing toxicity, selecting the subject for administration of a therapeutic regimen, the therapeutic regimen comprising administering to the subject:
i. the cell therapy, optionally at a non-reduced dose, optionally on an outpatient basis or without admission to the hospital for one or more days;
ii. the cell therapy, wherein administration of the cell therapy does not comprise administering, prior to or concurrently with administering the cell therapy and/or prior to the development of a sign or symptom of toxicity other than fever, an agent or treatment capable of treating, preventing, delaying, or attenuating the development of the toxicity; or
iii. the cell therapy in an outpatient setting and/or without admission of the subject to the hospital overnight or for one or more consecutive days and/or is without admission of the subject to the hospital for one or more days.

107. The kit of any of embodiments 87-104, wherein the instructions specify if the fold change indicates the subject is or is likely to develop toxicity, the therapeutic regimen is not administered to the subject.

108. The kit of embodiment 106, wherein the instructions specify:
the administration is carried out on an outpatient basis and/or without requiring admission to or an overnight stay at a hospital; and
if the subject exhibits a sustained fever or a fever that is or has not been reduced or not reduced by more than 1° C. after treatment with an antipyretic, the subject is admitted to the hospital or to an overnight stay at a hospital and/or is administered an agent or treatment for the treatment or prevention or reduction or attenuation of a neurotoxicity and/or a cytokine release syndrome or risk thereof.

109. The kit of any of embodiments 83-108, wherein the toxicity is neurotoxicity and/or cytokine release syndrome (CRS).

110. The kit of any of embodiments 87-109, wherein the toxicity is early toxicity that develops within 7 days of administration of the cell therapy.

111. The kit of any of embodiments 87-110, wherein the toxicity develops within 3, 4, 5, 6, or 7 days of administration of the cell therapy.

112. The kit of any of embodiments 87-111, wherein the toxicity is a first sign of a fever or is a sustained fever following administration of the cell therapy.

113. The kit of any of embodiments 83-112, wherein the cell therapy is or comprises tumor infiltrating lymphocytic (TIL) therapy.

114. The kit of any of embodiments 83-113, wherein the cell therapy comprises cells engineered to express a recombinant receptor that specifically binds to an antigen associated with a disease or condition and/or expressed in cells associated with the disease or condition.

115. The kit of any of embodiments 83-114, wherein the cell therapy is an adoptive cell therapy.

116. The kit of embodiment 114 or embodiment 115, wherein the cells comprise immune cells.

117. The kit of embodiment 116, wherein the immune cells are or comprise T cells or NK cells.

118. The kit of embodiment 117, wherein the immune cells are or comprise T cells and the T cells comprise CD4+ and/or CD8+ T cells.

119. The kit of any of embodiments 83-118, wherein the cell therapy is a T cell therapy comprising genetically engineered cells expressing a recombinant receptor.

120. The kit of embodiment 104, wherein the disease or condition is a cancer.

121. The kit of embodiment 104 or embodiment 120, wherein the cancer is a myeloma, leukemia or lymphoma.

122. The kit of embodiment 104, wherein the disease or condition is a B cell malignancy.

123. The kit of embodiment 122, wherein the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

124. The kit of any of embodiments 114-123, wherein the antigen is selected from among Trophoblast glycoprotein (TPBG also known as 5T4), 8H9, $\alpha v \beta 6$ integrin (avb6 integrin), B7-H3, B7-H6, B cell maturation antigen (BCMA), carbonic anhydrase 9 (CA9, also known as CAIX or G250), a cancer-testes antigen, carbonic anhydrase 9 (CAIX), C—C Motif Chemokine Ligand 1 (CCL-1), CD19, CD20, CD22, hepatitis B surface antigen, CD23, CD24, CD30, CD33, CD38, CD44, CD44v6, CD44v7/8, CD123, CD133, CD138, CD171, carcinoembryonic antigen (CEA), a cyclin, cyclin A2, c-Met, dual antigen, chondroitin sulfate proteoglycan 4 (CSPG4), epidermal growth factor protein (EGFR), epithelial glycoprotein 2 (EPG-2), epithelial glycoprotein 40 (EPG-40), ephrinB2, ephrin receptor A2 (EPHa2), ephrinB2, type III epidermal growth factor receptor mutation (EGFR vIII), estrogen receptor, folate receptor alpha, folate binding protein (FBP), Fc receptor like 5 (FCRL5; also known as Fc receptor homolog 5 or FCRH5), fetal acetylcholine receptor (Fetal AchR), G250/CAIX, ganglioside GD2, ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), Human leukocyte antigen A1 (HLA-A1), Human leukocyte antigen A2 (HLA-A2), IL-22 receptor alpha (IL-22R-alpha), IL-13 receptor alpha 2 (IL-13Ra2), kinase insert domain receptor (kdr), kappa light chain, Leucine Rich Repeat Containing 8 Family Member A (LRRC8A), Lewis Y, L1-cell adhesion molecule (L1-CAM), CE7 epitope of L1-CAM, Melanoma-associated antigen (MAGE)-A1, MAGE-A3, MAGE-A6, MAGE-A10, melan A (MART-1), mesothelin (MSLN), murine cytomegalovirus (CMV), mucin 1 (MUC1), MUC16, neural cell adhesion molecule (NCAM), natural killer group 2 member D (NKG2D), NKG2D ligands, cancer/testis antigen 1B (CTAG, also known as NY-ESO-1 and LAGE-2), O-acetylated GD2 (OGD2), oncofetal antigen, Preferentially expressed antigen of melanoma (PRAME), a prostate specific antigen, prostate stem cell antigen (PSCA), progesterone receptor, survivin, prostate specific membrane antigen (PSMA), Receptor Tyrosine Kinase Like Orphan Receptor 1 (ROR1), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGF receptors; VEGFR), vascular endothelial growth factor receptor 2 (VEGF-R2), Wilms Tumor 1 (WT-1), a pathogen-specific antigen.

125. The kit of any of embodiments 104-124, wherein the recombinant receptor is a T cell receptor or a functional non-T cell receptor.

126. The kit of any of embodiments 104-125, wherein the recombinant receptor is a chimeric antigen receptor (CAR).

127. The kit of embodiment 126, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

128. The kit of any of embodiments 83-127, further comprising an agent or other treatment capable of treating, preventing, delaying, reducing or attenuating the development or risk of development of a toxicity.

129. The kit of embodiment 128, wherein the agent or other treatment is or comprises one or more of a steroid; an antagonist or inhibitor of a cytokine receptor or cytokine selected from among IL-10, IL-10R, IL-6, IL-6 receptor, IFN$\gamma$, IFNGR, IL-2, IL-2R/CD25, MCP-1, CCR2, CCR4, MIP1$\beta$, CCR5, TNFalpha, TNFR1, IL-1, and IL-1Ralpha/IL-1beta; or an agent capable of preventing, blocking or reducing microglial cell activity or function.

130. The kit of embodiment 129, wherein the antagonist or inhibitor is or comprises an agent selected from among an antibody or antigen-binding fragment, a small molecule, a protein or peptide and a nucleic acid.

131. The kit of any of embodiments 128-130, wherein the agent or other treatment is an anti-IL-6 antibody or an anti-IL6 receptor antibody.

132. The kit of any of embodiments 128-131, wherein the agent or other treatment is or comprises an agent selected from among tocilizumab, siltuximab, clazakizumab, sarilumab, olokizumab (CDP6038), elsilimomab, ALD518/BMS-945429, sirukumab (CNTO 136), CPSI-2634, ARGX-109, FE301 and FM101.

133. The kit of any of embodiments 128-132, wherein the agent or other treatment is or comprises tocilizumab.

134. The kit of any of embodiments 128-133, wherein the agent or other treatment is or comprises siltuximab.

135. The kit of any of embodiments 129-134, wherein the steroid is or comprises dexamethasone.

136. The kit of any of embodiments 104-135, wherein the genetically engineered cells comprise T cells, and the T cells comprise CD4+ and/or CD8+ T cells.

137. The kit of embodiment 136, wherein the T cells are primary T cells obtained from a subject.

138. The kit of any of embodiments 83-137, wherein the cells of the cell therapy are autologous to the subject.

139. The kit of any of embodiments 83-138, wherein the cells are allogeneic to the subject.

140. The kit of embodiment 102 or embodiment 103, wherein the threshold value for SPD is about 5 fold, 6 fold, 7 fold, 8 fold, or 9 fold.

VIII. EXAMPLES

The following examples are included for illustrative purposes only and are not intended to limit the scope of the invention.

Example 1: Administration of an Anti-CD19 CAR-Expressing Cells and Assessment of Tumor Burden and Toxicity in Subjects with Relapsed and Refractory Non-Hodgkin's Lymphoma Therapeutic CAR+ T cell compositions containing autologous T cells expressing a chimeric antigen-receptor (CAR) specific for CD19 were administered to adult human subjects with relapsed or refractory (R/R) aggressive non-Hodgkin's lymphoma (NHL) after failure of at least 2 lines of therapy. The therapeutic T cell compositions administered had been generated by a process including immunoaffinity-based enrichment of CD4+ and CD8+ cells from leukapheresis samples from the individual subjects to be treated. Isolated CD4+ and CD8+ T cells were activated and transduced with a viral vector encoding an anti-CD19 CAR, followed by expansion and cryopreservation of the engineered cell populations. The CAR contained an anti-CD19 scFv derived from a murine antibody, an immunoglobulin-derived spacer, a transmembrane domain derived from CD28, a costimulatory region derived from 4-1BB, and a CD3-zeta intracellular signaling domain.

The cryopreserved cell compositions were thawed prior to intravenous administration. The therapeutic T cell dose was administered as a defined cell composition by administering a formulated CD4+CAR+ cell population and a formulated CD8+CAR+ population administered at a target ratio of approximately 1:1. Subjects were administered a single dose containing $5 \times 10^7$ total CAR-expressing T cells (via separate infusions of CD4+CAR-expressing T cells and CD8+CAR-expressing T cells). Beginning at three (3) days prior to CAR+ T cell infusion, subjects received a lymphodepleting chemotherapy.

To obtain a volumetric measure of tumor burden, PET scans were obtained at two time points including at screening and prior to administration of lymphodepletion treatment to confirm PET-avid disease. The sums of the perpendicular diameters (SPDs) was determined for measurable lesions on PET scan. The SPD at screening scan and SPD measured immediately prior to administration of the lymphodepletion treatment (pre-lymphodepleting treatment SPD) was compared, and the fold change in SPD over the period between these two timepoints determined for a number of the subjects. Ferritin levels in serum were similarly obtained just prior to administration of the lymphodepleting chemotherapy (Pre-lymphodepleting treatment Ferritin). Subjects were monitored and assessed for various outcomes, including the presence or absence of symptoms of outcomes including outcomes indicative of toxicity (such as CRS or neurotoxicity (NT).

Table E1 summarizes results for a study comparing levels of the measure of tumor burden (SPD) at the two time points and incidence of early CRS. Among ten of the subjects treated as described above for which SPD measurements and fold change had been determined, early toxicity (CRS), within the first 7 days following initiation of administration of the cell therapy was observed in three subjects (3/10) and no signs of CRS or neurotoxicity was observed within the first 3 weeks after administration of the cell therapy in seven subjects (7/10). A correlation between the relative change in SPD and early toxicity was observed.

| Subject # | Screening SPD | Pre-lymphodepleting treatment SPD | Fold change | Pre-lymphodepleting treatment Ferritin (ng/mL) | Median Ferritin Among Group of Subjects |
|---|---|---|---|---|---|
| Group of Subjects Exhibiting Early Toxicity ||||||
| 1 | 19.6 | 268 | 13.7 | 4399 | 1224 |
| 2 | 4.2 | 79 | 18.8 | 172 | |
| 3 | 19 | 245 | 12.9 | 1224 | |
| Group of Subjects Not Exhibiting Early Toxicity ||||||
| 4 | 8 | 12 | 1.5 | 514 | 395 |
| 5 | 6 | 7 | 1.2 | 395 | |
| 6 | 9.7 | 95 | 9.8 | 1166 | |
| 7 | 4.2 | 16 | 3.8 | 236 | |
| 9 | 4.8 | 15 | 3.1 | 960 | |
| 10 | 8.3 | 6.9 | 0.83 | 262 | |
| 11 | 6.1 | 7 | 1.1 | 20 | |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) homo sapiens |
| 3 | ESKYGPPCPPCPGQPREPQVYTLPPSQEEMTKNQVSLTCLVKGF YPSDIAVEWESNGQPENNYKTTPPVLDSDGSFFLYSRLTVDKSR WQEGNVFSCSVMHEALHNHYTQKSLSLSLGK | Hinge-CH3 spacer Homo sapiens |

-continued

| SEQ ID NO. | SEQUENCE | DESCRIPTION |
|---|---|---|
| 4 | ESKYGPPCPPCPAPEFLGGPSVFLFPPKPKDTLMISRTPEVTCVV VDVSQEDPEVQFNWYVDGVEVHNAKTKPREEQFNSTYRVVSV LTVLHQDWLNGKEYKCKVSNKGLPSSIEKTISKAKGQPREPQV YTLPPSQEEMTKNQVSLTCLVKGFYPSDIAVEWESNGQPENNY KTTPPVLDSDGSFFLYSRLTVDKSRWQEGNVFSCSVMHEALHN HYTQKSLSLSLGK | Hinge-CH2-CH3 spacer *Homo sapiens* |
| 5 | RWPESPKAQASSVPTAQPQAEGSLAKATTAPATTRNTGRGGEE KKKEKEKEEQEERETKTPECPSHTQPLGVYLLTPAVQDLWLRD KATFTCFVVGSDLKDAHLTWEVAGKVPTGGVEEGLLERHSNG SQSQHSRLTLPRSLWNAGTSVTCTLNHPSLPPQRLMALREPAA QAPVKLSLNLLASSDPPEAASWLLCEVSGFSPPNILLMWLEDQR EVNTSGFAPARPPPQPGSTTFWAWSVLRVPAPPSPQPATYTCVV SHEDSRTLLNASRSLEVSYVTDH | IgD-hinge-Fc *Homo sapiens* |
| 6 | LEGGGEGRGSLLTCGDVEENPGPR | T2A artificial |
| 7 | MLLLVTSLLLCELPHPAFLLIPRKVCNGIGIGEFKDSLSINATNIK HFKNCTSISGDLHILPVAFRGDSFTHTPPLDPQELDILKTVKEITG FLLIQAWPENRTDLHAFENLEIIRGRTKQHGQFSLAVVSLNITSL GLRSLKEISDGDVIISGNKNLCYANTINWKKLFGTSGQKTKIISN RGENSCKATGQVCHALCSPEGCWGPEPRDCVSCRNVSRGREC VDKCNLLEGEPREFVENSECIQCHPECLPQAMNITCTGRGPDNC IQCAHYIDGPHCVKTCPAGVMGENNTLVWKYADAGHVCHLC HPNCTYGCTGPGLEGCPTNGPKIPSIATGMVGALLLLLVVALGI GLFM | tEGFR artificial |
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKPFWVLV VVGGVLACYSLLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR | CD3 zeta *Homo sapiens* |
| 14 | RVKFSRSAEPPAYQQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR | CD3 zeta *Homo sapiens* |
| 15 | RVKFSRSADAPAYKQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR | CD3 zeta *Homo sapiens* |
| 16 | RKVCNGIGIGEFKDSLSINATNIKHFKNCTSISGDLHILPVAFRGD SFTHTPPLDPQELDILKTVKEITGFLLIQAWPENRTDLHAFENLEI IRGRTKQHGQFSLAVVSLNITSLGLRSLKEISDGDVIISGNKNLC YANTINWKKLFGTSGQKTKIISNRGENSCKATGQVCHALCSPEG CWGPEPRDCVSCRNVSRGRECVDKCNLLEGEPREFVENSECIQ CHPECLPQAMNITCTGRGPDNCIQCAHYIDGPHCVKTCPAGVM | tEGFR artificial |

-continued

| SEQ ID NO. | SEQUENCE | DESCRIPTION |
|---|---|---|
|  | GENNTLVWKYADAGHVCHLCHPNCTYGCTGPGLEGCPTNGPK IPSIATGMVGALLLLLVVALGIGLFM |  |
| 17 | EGRGSLLTCGDVEENPGP | T2A artificial |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | PGGG-(SGGGG)5-P- wherein P is proline, G is glycine and S is serine | Linker |
| 23 | GSADDAKKDAAKKDGKS | Linker |
| 24 | MALPVTALLLPLALLLHA | CD8 alpha signal peptide |
| 25 | atgcttctcctggtgacaagccttctgctctgtgagttaccacacccagcattcctcctgatccca | GMCSFR alpha chain signal sequence |
| 26 | MLLLVTSLLLCELPHPAFLLIP | GMCSFR alpha chain signal sequence |
| 27 | Glu Arg Lys Cys Cys Val Glu Cys Pro Pro Cys Pro | Hinge |
| 28 | ELKTPLGDTHTCPRCPEPKSCDTPPPCPRCPEPKSCDTPPPCPRCP EPKSCDTPPPCPRCP | Hinge |
| 29 | Glu Ser Lys Tyr Gly Pro Pro Cys Pro Ser Cys Pro | Hinge |
| 30 | Glu Ser Lys Tyr Gly Pro Pro Cys Pro Pro Cys Pro | Hinge |
| 31 | Tyr Gly Pro Pro Cys Pro Pro Cys Pro | Hinge |
| 32 | Lys Tyr Gly Pro Pro Cys Pro Pro Cys Pro | Hinge |
| 33 | Glu Val Val Val Lys Tyr Gly Pro Pro Cys Pro Pro Cys Pro | Hinge |
| 34 | QQGNTLPYT | LC-CDR3 |
| 35 | RASQDISKYLN | CDR L1 |
| 36 | SRLHSGV | CDR L2 |
| 37 | GNTLPYTFG | CDR L3 |
| 38 | DYGVS | CDR H1 |
| 39 | VIWGSETTYYNSALKS | CDR H2 |
| 40 | YAMDYWG | CDR H3 |
| 41 | EVKLQESGPGLVAPSQSLSVTCTVSGVSLPDYGVSWIRQPPRKGLEWL GVIWGSETTYYNSALKSRLTIIKDNSKSQVFLKMNSLQTDDTAIYYCA KHYYYGGSYAMDYWGQGTSVTVSS | VH |
| 42 | DIQMTQTTSSLSASLGDRVTISCRASQDISKYLNWYQQKPDGTVKLLI YHTSRLHSGVPSRFSGSGSGTDYSLTISNLEQEDIATYFCQQGNTLPYT FGGGTKLEIT | VL |
| 43 | DIQMTQTTSSLSASLGDRVTISCRASQDISKYLNWYQQKPDGTVKLLI YHTSRLHSGVPSRFSGSGSGTDYSLTISNLEQEDIATYFCQQGNTLPYT FGGGTKLEITGSTSGSGKPGSGEGSTKGEVKLQESGPGLVAPSQSLSVT CTVSGVSLPDYGVSWIRQPPRKGLEWLGVIWGSETTYYNSALKSRLTII KDNSKSQVFLKMNSLQTDDTAIYYCAKHYYYGGSYAMDYWGQGTS VTVSS | scFv |
| 44 | KASQNVGTNVA | CDR L1 |

| SEQ ID NO. | SEQUENCE | DESCRIPTION |
|---|---|---|
| 45 | SATYRNS | CDR L2 |
| 46 | QQYNRYPYT | CDR L3 |
| 47 | SYWMN | CDR H1 |
| 48 | QIYPGDGDTNYNGKFKG | CDR H2 |
| 49 | KTISSVVDFYFDY | CDR H3 |
| 50 | EVKLQQSGAELVRPGSSVKISCKASGYAFSSYWMNWVKQRPGQGLE WIGQIYPGDGDTNYNGKFKGQATLTADKSSSTAYMQLSGLTSEDSAV YFCARKTISSVVDFYFDYWGQGTTVTVSS | VH |
| 51 | DIELTQSPKFMSTSVGDRVSVTCKASQNVGTNVAWYQQKPGQSPKPLI YSATYRNSGVPDRFTGSGSGTDFTLTITNVQSKDLADYFCQQYNRYPY TSGGGTKLEIKR | VL |
| 52 | GGGGSGGGGSGGGGS | Linker |
| 53 | EVKLQQSGAELVRPGSSVKISCKASGYAFSSYWMNWVKQRPGQGLE WIGQIYPGDGDTNYNGKFKGQATLTADKSSSTAYMQLSGLTSEDSAV YFCARKTISSVVDFYFDYWGQGTTVTVSSGGGGSGGGGSGGGGSDIE LTQSPKFMSTSVGDRVSVTCKASQNVGTNVAWYQQKPGQSPKPLIYS ATYRNSGVPDRFTGSGSGTDFTLTITNVQSKDLADYFCQQYNRYPYTS GGGTKLEIKR | scFv |
| 54 | HYYYGGSYAMDY | HC-CDR3 |
| 55 | HTSRLHS | LC-CDR2 |
| 56 | GSTSGSGKPGSGEGSTKG | Linker |
| 57 | gacatccagatgacccagaccacctccagcctgagcgccagcctgggcgaccgggtgaccatcagctgccg ggccagccaggacatcagcaagtacctgaactggtatcagcagaagcccgacggcaccgtcaagctgctgat ctaccacaccagccggctgcacagcggcgtgcccagccgtttagcggcagcggctccggcaccgactaca gcctgaccatctccaacctggaacaggaagatatcgccacctactttttgccagcagggcaacacactgccct acacctttggcggcggaacaaagctggaaatcaccggcagcacctccggcagcggcaagcctggcagcggcg agggcagcaccaagggcgaggtgaagctgcaggaaagcggccctggcctggtggcccccagccagagcct gagcgtgacctgcaccgtgagcggcgtgagcctgcccgactacggcgtgagctggatccggcagcccccca ggaagggcctggaatggctgggcgtgatctggggcagcgagaccacctactacaacagcgccctgaagagc cggctgaccatcatcaaggacaacagcaagagccaggtgttcctgaagatgaacagcctgcagaccgacgac accgccatctactactgcgccaagcactactactacggcggcagctacgccatggactactggggccagggc accagcgtgaccgtgagcagc | Sequence encoding scFv |
| 58 | X1PPX2P<br>X1 is glycine, cysteine or arginine<br>X2 is cysteine or threonine | Hinge |
| 59 | Glu Pro Lys Ser Cys Asp Lys Thr His Thr Cys Pro Pro Cys Pro | Hinge |
| 60 | MPLLLLLPLLWAGALA | CD33 signal peptide |

---

What is claimed:

1. A method of reducing the risk of development of a toxicity in a subject, the method comprising:
   (a) measuring a sum of products of diameters (SPD) of a tumor of a subject having a cancer at a first time point and a second time point that are each measured prior to administration of a T cell therapy for treatment of a cancer, wherein the subject is a candidate for receiving the T cell therapy, and wherein the fold change of the SPD of the tumor between the first time point and the second time point is about 5 or greater; and
   (b) administering to the subject: (i) the T cell therapy, and (ii) an agent capable of reducing the risk of development of a toxicity, wherein the toxicity is cytokine release syndrome (CRS) or neurotoxicity.

2. The method of claim 1, wherein the subject is administered a lymphodepleting therapy prior to administering the T cell therapy.

3. The method of claim 2, wherein the first time point is at or about at a time of screening the subject as a candidate for treatment with the T cell therapy, and the second time point is at or immediately prior to the subject receiving the lymphodepleting therapy.

4. The method of claim 2, wherein the lymphodepleting therapy is administered at least 2 days prior to and no more than 7 days prior to initiation of administration of the T cell therapy.

5. The method of claim 4, wherein the second time point is at or immediately prior to administering the lymphodepleting therapy.

6. The method of claim 2, wherein the second time point is at or immediately prior to the administration of the lymphodepleting therapy.

7. The method of claim 6, wherein the first time point and the second time point are not more than six weeks apart.

8. The method of claim 1, wherein the first time point and the second time point are both no more two months prior to administration of the T cell therapy.

9. The method of claim 1, wherein the two time points are not more than six weeks apart.

10. The method of claim 1, wherein the second time point is 2-7 days before administration of the T cell therapy.

11. The method of claim 1, wherein the agent capable of reducing the risk of development of a toxicity is administered before any symptom of the toxicity is present.

12. The method of claim 1, wherein the agent capable of reducing the risk of development of a toxicity is administered prior to a first fever following the initiation of administration of the T cell therapy to the subject.

13. The method of claim 1, wherein the agent capable of reducing the risk of development of a toxicity is administered within one, two, or three days of a first fever following the initiation of administration of the T cell therapy to the subject.

14. The method of claim 1, wherein the agent capable of reducing the risk of development of toxicity is administered prior to the T cell therapy.

15. The method of claim 1, wherein the agent capable of reducing the risk of development of a toxicity is administered subsequent to the T cell therapy and before any symptom of a toxicity is present.

16. The method of claim 1, wherein the cancer is a B cell malignancy.

17. The method of claim 16, wherein the B cell malignancy is selected from acute lymphoblastic leukemia (ALL), chronic lymphocytic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

18. The method of claim 1, wherein:
   greater than or greater than about 30% of the subjects administered the agent do not exhibit any grade of cytokine release syndrome (CRS) or neurotoxicity; and/or
   at least at or about 45% of subjects administered the agent do not exhibit severe CRS; and/or
   at least at or about 45% of subjects administered the agent do not exhibit severe neurotoxicity; and/or
   at least at or about 45% of subjects administered the agent do not exhibit cerebral edema.

19. The method of claim 1, wherein the cell therapy comprises genetically engineered T cells expressing a recombinant receptor that specifically binds to an antigen associated with cancer and/or expressed in cells associated with the cancer.

20. The method of claim 19, wherein the recombinant receptor is a T cell receptor or a functional non-T cell receptor.

21. The method of claim 19, wherein the recombinant receptor is a chimeric antigen receptor (CAR).

22. The method of claim 1, wherein the T cell therapy comprises the administration of from or from about $1 \times 10^5$ to $1 \times 10^8$ total recombinant receptor-expressing cells, total T cells, or total peripheral blood mononuclear cells (PBMCs); from or from about $5 \times 10^5$ to $1 \times 10^7$ total recombinant receptor-expressing cells, total T cells, or total peripheral blood mononuclear cells (PBMCs); or from or from about $1 \times 10^6$ to $1 \times 10^7$ total recombinant receptor-expressing cells, total T cells, or total peripheral blood mononuclear cells (PBMCs), each inclusive.

23. The method of claim 22, wherein the T cell therapy comprises the administration of from about $5 \times 10^7$ to about $1 \times 10^8$ total recombinant receptor-expressing cells, total T cells, or total peripheral blood mononuclear cells (PBMCs).

24. The method of claim 1, wherein the fold change is about 9 or greater.

25. The method of claim 1, wherein the agent capable of reducing the risk of development of a toxicity is a steroid, an antagonist or inhibitor of a cytokine receptor, or an antagonist or inhibitor of a cytokine.

26. The method of claim 1, wherein the agent capable of reducing the risk of development of a toxicity is a steroid and the steroid is a glucocorticoid.

27. The method of claim 26, wherein the glucocorticoid is dexamethasone.

28. The method of claim 1, wherein the agent capable of reducing the risk of development of a toxicity is an anti-IL-6R antibody or antigen-binding fragment thereof or is an antagonist or inhibitor of IL-6.

29. The method of claim 28, wherein the anti-IL-6R antibody or antigen-binding fragment thereof is tocilizumab or sarilumab.

30. A method of reducing the risk of development of a toxicity in a subject, comprising administering an agent capable of reducing the risk of development of a toxicity to the subject, wherein the toxicity is cytokine release syndrome (CRS) or neurotoxicity,
wherein the subject has cancer and has been administered a T cell therapy for treating the cancer, and the subject has been measured for a sum of the products of diameters (SPD) of a tumor of the subject at a first time point and a second time point that are each measured prior to administration of the T cell therapy, wherein the first and second time point are no more than six weeks apart, wherein the fold change of the SPD of the tumor between the first time point and the second time point is about 5 or greater.

31. The method of claim 30, wherein the subject has been administered a lymphodepleting therapy prior to administering the T cell therapy and the first and second time point is before administering the lymphodepleting therapy.

32. The method of claim 30, wherein the agent capable of reducing the risk of development of a toxicity is administered before any symptom of the toxicity is present.

33. The method of claim 30, wherein the agent capable of reducing the risk of development of a toxicity is administered prior to a first fever following the initiation of administration of the T cell therapy to the subject.

34. The method of claim 30, wherein the agent capable of reducing the risk of development of a toxicity is a steroid, an antagonist or inhibitor of a cytokine receptor, or an antagonist or inhibitor of a cytokine.

35. The method of claim 30, wherein the agent capable of reducing the risk of development of a toxicity is an anti-IL-6R antibody or antigen-binding fragment thereof or an antagonist or inhibitor IL-6.

36. The method of claim 30, wherein the agent capable of reducing the risk of development of a toxicity is tocilizumab or sarilumab.

37. The method of claim 30, wherein the agent capable of reducing the risk of development of a toxicity is dexamethasone.

* * * * *

SEQUENCE LISTING

```
Sequence total quantity: 60
SEQ ID NO: 1           moltype = AA  length = 12
FEATURE                Location/Qualifiers
REGION                 1..12
                       note = Spacer (IgG4hinge)
source                 1..12
                       mol_type = protein
                       organism = Homo sapiens
SEQUENCE: 1
ESKYGPPCPP CP                                                         12

SEQ ID NO: 2           moltype = DNA  length = 36
```

```
FEATURE                 Location/Qualifiers
misc_feature            1..36
                        note = Spacer (IgG4hinge)
source                  1..36
                        mol_type = unassigned DNA
                        organism = Homo sapiens
SEQUENCE: 2
gaatctaagt acggaccgcc ctgcccccct tgccct                                  36

SEQ ID NO: 3            moltype = AA  length = 119
FEATURE                 Location/Qualifiers
REGION                  1..119
                        note = Hinge-CH3 spacer
source                  1..119
                        mol_type = protein
                        organism = Homo sapiens
SEQUENCE: 3
ESKYGPPCPP CPGQPREPQV YTLPPSQEEM TKNQVSLTCL VKGFYPSDIA VEWESNGQPE         60
NNYKTTPPVL DSDGSFFLYS RLTVDKSRWQ EGNVFSCSVM HEALHNHYTQ KSLSLSLGK         119

SEQ ID NO: 4            moltype = AA  length = 229
FEATURE                 Location/Qualifiers
REGION                  1..229
                        note = Hinge-CH2-CH3 spacer
source                  1..229
                        mol_type = protein
                        organism = Homo sapiens
SEQUENCE: 4
ESKYGPPCPP CPAPEFLGGP SVFLFPPKPK DTLMISRTPE VTCVVVDVSQ EDPEVQFNWY         60
VDGVEVHNAK TKPREEQFNS TYRVVSVLTV LHQDWLNGKE YKCKVSNKGL PSSIEKTISK        120
AKGQPREPQV YTLPPSQEEM TKNQVSLTCL VKGFYPSDIA VEWESNGQPE NNYKTTPPVL        180
DSDGSFFLYS RLTVDKSRWQ EGNVFSCSVM HEALHNHYTQ KSLSLSLGK                   229

SEQ ID NO: 5            moltype = AA  length = 282
FEATURE                 Location/Qualifiers
REGION                  1..282
                        note = IgD-hinge-Fc
source                  1..282
                        mol_type = protein
                        organism = Homo sapiens
SEQUENCE: 5
RWPESPKAQA SSVPTAQPQA EGSLAKATTA PATTRNTGRG GEEKKKEKEK EEQEERETKT         60
PECPSHTQPL GVYLLTPAVQ DLWLRDKATF TCFVVGSDLK DAHLTWEVAG KVPTGGVEEG        120
LLERHSNGSQ SQHSRLTPRS SLWNAGTSVT CTLNHPSLPP QRLMALREPA AQAPVKLSLN        180
LLASSDPPEA ASWLLCEVSG FSPPNILLMW LEDQREVNTS GFAPARPPPQ PGSTTFWAWS        240
VLRVPAPPSP QPATYTCVVS HEDSRTLLNA SRSLEVSYVT DH                          282

SEQ ID NO: 6            moltype = AA  length = 24
FEATURE                 Location/Qualifiers
REGION                  1..24
                        note = T2A
source                  1..24
                        mol_type = protein
                        organism = synthetic construct
SEQUENCE: 6
LEGGGEGRGS LLTCGDVEEN PGPR                                               24

SEQ ID NO: 7            moltype = AA  length = 357
FEATURE                 Location/Qualifiers
REGION                  1..357
                        note = tEGFR
source                  1..357
                        mol_type = protein
                        organism = synthetic construct
SEQUENCE: 7
MLLLVTSLLL CELPHPAFLL IPRKVCNGIG IGEFKDSLSI NATNIKHFKN CTSISGDLHI         60
LPVAFRGDSF THTPPLDPQE LDILKTVKEI TGFLLIQAWP ENRTDLHAFE NLEIIRGRTK        120
QHGQFSLAVV SLNITSLGLR SLKEISDGDV IISGNKNLCY ANTINWKKLF GTSGQKTKII        180
SNRGENSCKA TGQVCHALCS PEGCWGPEPR DCVSCRNVSR GRECVDKCNL LEGEPREFVE        240
NSECIQCHPE CLPQAMNITC TGRGPDNCIQ CAHYIDGPHC VKTCPAGVMG ENNTLVWKYA        300
DAGHVCHLCH PNCTYGCTGP GLEGCPTNGP KIPSIATGMV GALLLLLVVA LGIGLFM          357

SEQ ID NO: 8            moltype = AA  length = 27
FEATURE                 Location/Qualifiers
REGION                  1..27
                        note = CD28
source                  1..27
                        mol_type = protein
                        organism = Homo sapiens
```

```
SEQUENCE: 8
FWVLVVVGGV LACYSLLVTV AFIIFWV                                            27

SEQ ID NO: 9           moltype = AA  length = 66
FEATURE                Location/Qualifiers
REGION                 1..66
                       note = CD28
source                 1..66
                       mol_type = protein
                       organism = Homo sapiens
SEQUENCE: 9
IEVMYPPPYL DNEKSNGTII HVKGKHLCPS PLFPGPSKPF WVLVVVGGVL ACYSLLVTVA        60
FIIFWV                                                                   66

SEQ ID NO: 10          moltype = AA  length = 41
FEATURE                Location/Qualifiers
REGION                 1..41
                       note = CD28
source                 1..41
                       mol_type = protein
                       organism = Homo sapiens
SEQUENCE: 10
RSKRSRLLHS DYMNMTPRRP GPTRKHYQPY APPRDFAAYR S                            41

SEQ ID NO: 11          moltype = AA  length = 41
FEATURE                Location/Qualifiers
REGION                 1..41
                       note = CD28
source                 1..41
                       mol_type = protein
                       organism = Homo sapiens
SEQUENCE: 11
RSKRSRGGHS DYMNMTPRRP GPTRKHYQPY APPRDFAAYR S                            41

SEQ ID NO: 12          moltype = AA  length = 42
FEATURE                Location/Qualifiers
REGION                 1..42
                       note = 4-1BB
source                 1..42
                       mol_type = protein
                       organism = Homo sapiens
SEQUENCE: 12
KRGRKKLLYI FKQPFMRPVQ TTQEEDGCSC RFPEEEEGGC EL                           42

SEQ ID NO: 13          moltype = AA  length = 112
FEATURE                Location/Qualifiers
REGION                 1..112
                       note = CD3 zeta
source                 1..112
                       mol_type = protein
                       organism = Homo sapiens
SEQUENCE: 13
RVKFSRSADA PAYQQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR                112

SEQ ID NO: 14          moltype = AA  length = 112
FEATURE                Location/Qualifiers
REGION                 1..112
                       note = CD3 zeta
source                 1..112
                       mol_type = protein
                       organism = Homo sapiens
SEQUENCE: 14
RVKFSRSAEP PAYQQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR                112

SEQ ID NO: 15          moltype = AA  length = 112
FEATURE                Location/Qualifiers
REGION                 1..112
                       note = CD3 zeta
source                 1..112
                       mol_type = protein
                       organism = Homo sapiens
SEQUENCE: 15
RVKFSRSADA PAYKQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR                112

SEQ ID NO: 16          moltype = AA  length = 335
FEATURE                Location/Qualifiers
```

```
REGION                  1..335
                        note = tEGFR
source                  1..335
                        mol_type = protein
                        organism = synthetic construct
SEQUENCE: 16
RKVCNGIGIG EFKDSLSINA TNIKHFKNCT SISGDLHILP VAFRGDSFTH TPPLDPQELD    60
ILKTVKEITG FLLIQAWPEN RTDLHAFENL EIIRGRTKQH GQFSLAVVSL NITSLGLRSL   120
KEISDGDVII SGNKNLCYAN TINWKKLFGT SGQKTKIISN RGENSCKATG QVCHALCSPE   180
GCWGPEPRDC VSCRNVSRGR ECVDKCNLLE GEPREFVENS ECIQCHPECL PQAMNITCTG   240
RGPDNCIQCA HYIDGPHCVK TCPAGVMGEN NTLVWKYADA GHVCHLCHPN CTYGCTGPGL   300
EGCPTNGPKI PSIATGMVGA LLLLLVVALG IGLFM                              335

SEQ ID NO: 17           moltype = AA   length = 18
FEATURE                 Location/Qualifiers
REGION                  1..18
                        note = T2A
source                  1..18
                        mol_type = protein
                        organism = synthetic construct
SEQUENCE: 17
EGRGSLLTCG DVEENPGP                                                  18

SEQ ID NO: 18           moltype = AA   length = 22
FEATURE                 Location/Qualifiers
REGION                  1..22
                        note = P2A
source                  1..22
                        mol_type = protein
                        organism = synthetic construct
SEQUENCE: 18
GSGATNFSLL KQAGDVEENP GP                                             22

SEQ ID NO: 19           moltype = AA   length = 19
FEATURE                 Location/Qualifiers
REGION                  1..19
                        note = P2A
source                  1..19
                        mol_type = protein
                        organism = synthetic construct
SEQUENCE: 19
ATNFSLLKQA GDVEENPGP                                                 19

SEQ ID NO: 20           moltype = AA   length = 20
FEATURE                 Location/Qualifiers
REGION                  1..20
                        note = E2A
source                  1..20
                        mol_type = protein
                        organism = synthetic construct
SEQUENCE: 20
QCTNYALLKL AGDVESNPGP                                                20

SEQ ID NO: 21           moltype = AA   length = 22
FEATURE                 Location/Qualifiers
REGION                  1..22
                        note = F2A
source                  1..22
                        mol_type = protein
                        organism = synthetic construct
SEQUENCE: 21
VKQTLNFDLL KLAGDVESNP GP                                             22

SEQ ID NO: 22           moltype = AA   length = 10
FEATURE                 Location/Qualifiers
REGION                  1..10
                        note = Linker
REPEAT                  5..9
                        note = SGGGG is repeated 5 times
source                  1..10
                        mol_type = protein
                        organism = synthetic construct
SEQUENCE: 22
PGGGSGGGGP                                                           10

SEQ ID NO: 23           moltype = AA   length = 17
FEATURE                 Location/Qualifiers
REGION                  1..17
                        note = Linker
```

```
source                  1..17
                        mol_type = protein
                        organism = synthetic construct
SEQUENCE: 23
GSADDAKKDA AKKDGKS                                               17

SEQ ID NO: 24           moltype = AA  length = 18
FEATURE                 Location/Qualifiers
REGION                  1..18
                        note = CD8 alpha signal peptide
source                  1..18
                        mol_type = protein
                        organism = synthetic construct
SEQUENCE: 24
MALPVTALLL PLALLLHA                                              18

SEQ ID NO: 25           moltype = DNA  length = 66
FEATURE                 Location/Qualifiers
misc_feature            1..66
                        note = GMCSFR alpha chain signal sequence
source                  1..66
                        mol_type = other DNA
                        organism = synthetic construct
SEQUENCE: 25
atgcttctcc tggtgacaag ccttctgctc tgtgagttac cacacccagc attcctcctg   60
atccca                                                             66

SEQ ID NO: 26           moltype = AA  length = 22
FEATURE                 Location/Qualifiers
REGION                  1..22
                        note = GMCSFR alpha chain signal sequence
source                  1..22
                        mol_type = protein
                        organism = synthetic construct
SEQUENCE: 26
MLLLVTSLLL CELPHPAFLL IP                                         22

SEQ ID NO: 27           moltype = AA  length = 12
FEATURE                 Location/Qualifiers
REGION                  1..12
                        note = Hinge
source                  1..12
                        mol_type = protein
                        organism = synthetic construct
SEQUENCE: 27
ERKCCVECPP CP                                                    12

SEQ ID NO: 28           moltype = AA  length = 61
FEATURE                 Location/Qualifiers
REGION                  1..61
                        note = Hinge
source                  1..61
                        mol_type = protein
                        organism = synthetic construct
SEQUENCE: 28
ELKTPLGDTH TCPRCPEPKS CDTPPPCPRC PEPKSCDTPP PCPRCPEPKS CDTPPPCPRC   60
P                                                                  61

SEQ ID NO: 29           moltype = AA  length = 12
FEATURE                 Location/Qualifiers
REGION                  1..12
                        note = Hinge
source                  1..12
                        mol_type = protein
                        organism = synthetic construct
SEQUENCE: 29
ESKYGPPCPS CP                                                    12

SEQ ID NO: 30           moltype = AA  length = 12
FEATURE                 Location/Qualifiers
REGION                  1..12
                        note = Hinge
source                  1..12
                        mol_type = protein
                        organism = synthetic construct
SEQUENCE: 30
ESKYGPPCPP CP                                                    12

SEQ ID NO: 31           moltype = AA  length = 9
```

```
FEATURE                 Location/Qualifiers
REGION                  1..9
                        note = Hinge
source                  1..9
                        mol_type = protein
                        organism = synthetic construct SEQUENCE: 31
YGPPCPPCP                                                                         9

SEQ ID NO: 32           moltype = AA  length = 10
FEATURE                 Location/Qualifiers
REGION                  1..10
                        note = Hinge
source                  1..10
                        mol_type = protein
                        organism = synthetic construct SEQUENCE: 32
KYGPPCPPCP                                                                       10

SEQ ID NO: 33           moltype = AA  length = 14
FEATURE                 Location/Qualifiers
REGION                  1..14
                        note = Hinge
source                  1..14
                        mol_type = protein
                        organism = synthetic construct SEQUENCE: 33
EVVVKYGPPC PPCP                                                                  14

SEQ ID NO: 34           moltype = AA  length = 9
FEATURE                 Location/Qualifiers
REGION                  1..9
                        note = LC-CDR3
source                  1..9
                        mol_type = protein
                        organism = synthetic construct SEQUENCE: 34
QQGNTLPYT                                                                         9

SEQ ID NO: 35           moltype = AA  length = 11
FEATURE                 Location/Qualifiers
REGION                  1..11
                        note = CDR L1
source                  1..11
                        mol_type = protein
                        organism = synthetic construct SEQUENCE: 35
RASQDISKYL N                                                                     11

SEQ ID NO: 36           moltype = AA  length = 7
FEATURE                 Location/Qualifiers
REGION                  1..7
                        note = CDR L2
source                  1..7
                        mol_type = protein
                        organism = synthetic construct SEQUENCE: 36
SRLHSGV                                                                           7

SEQ ID NO: 37           moltype = AA  length = 9
FEATURE                 Location/Qualifiers
REGION                  1..9
                        note = CDR L3
source                  1..9
                        mol_type = protein
                        organism = synthetic construct SEQUENCE: 37
GNTLPYTFG                                                                         9

SEQ ID NO: 38           moltype = AA  length = 5
FEATURE                 Location/Qualifiers
REGION                  1..5
                        note = CDR H1
source                  1..5
                        mol_type = protein
                        organism = synthetic construct SEQUENCE: 38
DYGVS                                                                             5
```

```
SEQ ID NO: 39           moltype = AA   length = 16
FEATURE                 Location/Qualifiers
REGION                  1..16
                        note = CDR H2
source                  1..16
                        mol_type = protein
                        organism = synthetic construct
SEQUENCE: 39
VIWGSETTYY NSALKS                                                   16

SEQ ID NO: 40           moltype = AA   length = 7
FEATURE                 Location/Qualifiers
REGION                  1..7
                        note = CDR H3
source                  1..7
                        mol_type = protein
                        organism = synthetic construct
SEQUENCE: 40
YAMDYWG                                                              7

SEQ ID NO: 41           moltype = AA   length = 120
FEATURE                 Location/Qualifiers
REGION                  1..120
                        note = VH
source                  1..120
                        mol_type = protein
                        organism = synthetic construct
SEQUENCE: 41
EVKLQESGPG LVAPSQSLSV TCTVSGVSLP DYGVSWIRQP PRKGLEWLGV IWGSETTYYN   60
SALKSRLTII KDNSKSQVFL KMNSLQTDDT AIYYCAKHYY YGGSYAMDYW GQGTSVTVSS  120

SEQ ID NO: 42           moltype = AA   length = 107
FEATURE                 Location/Qualifiers
REGION                  1..107
                        note = VL
source                  1..107
                        mol_type = protein
                        organism = synthetic construct
SEQUENCE: 42
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEIT               107

SEQ ID NO: 43           moltype = AA   length = 245
FEATURE                 Location/Qualifiers
REGION                  1..245
                        note = scFv
source                  1..245
                        mol_type = protein
                        organism = synthetic construct
SEQUENCE: 43
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                              245

SEQ ID NO: 44           moltype = AA   length = 11
FEATURE                 Location/Qualifiers
REGION                  1..11
                        note = CDR L1
source                  1..11
                        mol_type = protein
                        organism = synthetic construct
SEQUENCE: 44
KASQNVGTNV A                                                        11

SEQ ID NO: 45           moltype = AA   length = 7
FEATURE                 Location/Qualifiers
REGION                  1..7
                        note = CDR L2
source                  1..7
                        mol_type = protein
                        organism = synthetic construct
SEQUENCE: 45
SATYRNS                                                              7

SEQ ID NO: 46           moltype = AA   length = 9
FEATURE                 Location/Qualifiers
REGION                  1..9
```

```
                    note = CDR L3
source              1..9
                    mol_type = protein
                    organism = synthetic construct
SEQUENCE: 46
QQYNRYPYT                                                                       9

SEQ ID NO: 47       moltype = AA   length = 5
FEATURE             Location/Qualifiers
REGION              1..5
                    note = CDR H1
source              1..5
                    mol_type = protein
                    organism = synthetic construct
SEQUENCE: 47
SYWMN                                                                           5

SEQ ID NO: 48       moltype = AA   length = 17
FEATURE             Location/Qualifiers
REGION              1..17
                    note = CDR H2
source              1..17
                    mol_type = protein
                    organism = synthetic construct
SEQUENCE: 48
QIYPGDGDTN YNGKFKG                                                              17

SEQ ID NO: 49       moltype = AA   length = 13
FEATURE             Location/Qualifiers
REGION              1..13
                    note = CDR H3
source              1..13
                    mol_type = protein
                    organism = synthetic construct
SEQUENCE: 49
KTISSVVDFY FDY                                                                  13

SEQ ID NO: 50       moltype = AA   length = 122
FEATURE             Location/Qualifiers
REGION              1..122
                    note = VH
source              1..122
                    mol_type = protein
                    organism = synthetic construct
SEQUENCE: 50
EVKLQQSGAE LVRPGSSVKI SCKASGYAFS SYWMNWVKQR PGQGLEWIGQ IYPGDGDTNY               60
NGKFKGQATL TADKSSSTAY MQLSGLTSED SAVYFCARKT ISSVVDFYFD YWGQGTTVTV               120
SS                                                                              122

SEQ ID NO: 51       moltype = AA   length = 108
FEATURE             Location/Qualifiers
REGION              1..108
                    note = VL
source              1..108
                    mol_type = protein
                    organism = synthetic construct
SEQUENCE: 51
DIELTQSPKF MSTSVGDRVS VTCKASQNVG TNVAWYQQKP GQSPKPLIYS ATYRNSGVPD               60
RFTGSGSGTD FTLTITNVQS KDLADYFCQQ YNRYPYTSGG GTKLEIKR                            108

SEQ ID NO: 52       moltype = AA   length = 15
FEATURE             Location/Qualifiers
REGION              1..15
                    note = Linker
source              1..15
                    mol_type = protein
                    organism = synthetic construct
SEQUENCE: 52
GGGGSGGGGS GGGGS                                                                15

SEQ ID NO: 53       moltype = AA   length = 245
FEATURE             Location/Qualifiers
REGION              1..245
                    note = scFv
source              1..245
                    mol_type = protein
                    organism = synthetic construct
SEQUENCE: 53
EVKLQQSGAE LVRPGSSVKI SCKASGYAFS SYWMNWVKQR PGQGLEWIGQ IYPGDGDTNY               60
```

```
NGKFKGQATL TADKSSSTAY MQLSGLTSED SAVYFCARKT ISSVVDFYFD YWGQGTTVTV    120
SSGGGGSGGG GSGGGGSDIE LTQSPKFMST SVGDRVSVTC KASQNVGTNV AWYQQKPGQS    180
PKPLIYSATY RNSGVPDRFT GSGSGTDFTL TITNVQSKDL ADYFCQQYNR YPYTSGGGTK    240
LEIKR                                                               245

SEQ ID NO: 54           moltype = AA  length = 12
FEATURE                 Location/Qualifiers
REGION                  1..12
                        note = HC-CDR3
source                  1..12
                        mol_type = protein
                        organism = synthetic construct
SEQUENCE: 54
HYYYGGSYAM DY                                                       12

SEQ ID NO: 55           moltype = AA  length = 7
FEATURE                 Location/Qualifiers
REGION                  1..7
                        note = LC-CDR2
source                  1..7
                        mol_type = protein
                        organism = synthetic construct
SEQUENCE: 55
HTSRLHS                                                              7

SEQ ID NO: 56           moltype = AA  length = 18
FEATURE                 Location/Qualifiers
REGION                  1..18
                        note = Linker
source                  1..18
                        mol_type = protein
                        organism = synthetic construct
SEQUENCE: 56
GSTSGSGKPG SGEGSTKG                                                 18

SEQ ID NO: 57           moltype = DNA  length = 735
FEATURE                 Location/Qualifiers
misc_feature            1..735
                        note = Sequence encoding scFv
source                  1..735
                        mol_type = other DNA
                        organism = synthetic construct
SEQUENCE: 57
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctgaacag    240
gaagatatcg ccacctactt ttgccagcag ggcaacacac tgcccgtaca ctttggcgg    300
ggaacaaagc tggaaatcac cggcagcacc tccggcagcg gcaagcctgg cagcggcgag   360
ggcagcacca agggcgaggt gaagctgcag gaaagcggcc ctggcctggt gcccccagc    420
cagagcctga gcgtgacctg caccgtgagc ggcgtgagcc tgcccgacta cggcgtgagc   480
tggatccggc agcccccag gaagggcctg gaatggctgg gcgtgatctg ggcagcgag     540
accacctact acaacagcgc cctgaagagc cggctgacca tcatcaagga caacagcaag   600
agccaggtgt tcctgaagat gaacagcctg cagaccgacg acaccgccat ctactactgc   660
gccaagcact actactacgg cggcagctac gccatggact actggggcca gggcaccagc   720
gtgaccgtga gcagc                                                    735

SEQ ID NO: 58           moltype =     length =
SEQUENCE: 58
000

SEQ ID NO: 59           moltype = AA  length = 15
FEATURE                 Location/Qualifiers
REGION                  1..15
                        note = Hinge
source                  1..15
                        mol_type = protein
                        organism = synthetic construct
SEQUENCE: 59
EPKSCDKTHT CPPCP                                                    15
```

```
SEQ ID NO: 60        moltype = AA  length = 16
FEATURE              Location/Qualifiers
REGION               1..16
                     note = CD33 signal peptide
source               1..16
                     mol_type = protein
                     organism = Homo sapiens
SEQUENCE: 60
MPLLLLLPLL WAGALA                                                             16
```